(12) United States Patent
Zhao et al.

(10) Patent No.: US 11,149,021 B2
(45) Date of Patent: Oct. 19, 2021

(54) N-(AZAARYL)CYCLOLACTAM-1-CARBOXAMIDE DERIVATIVE, PREPARATION METHOD THEREFOR, AND USE THEREOF

(71) Applicant: Abbisko Therapeutics Co., Ltd., Shanghai (CN)

(72) Inventors: Baowei Zhao, Shanghai (CN); Mingming Zhang, Shanghai (CN); Hongping Yu, Shanghai (CN); Shuqun Yang, Shanghai (CN); Zhui Chen, Shanghai (CN); Yaochang Xu, Shanghai (CN)

(73) Assignee: ABBISKO THERAPEUTICS CO., LTD., Shanghai (CN)

( * ) Notice: Subject to any disclaimer, the term of this patent is extended or adjusted under 35 U.S.C. 154(b) by 25 days.

(21) Appl. No.: 16/610,970

(22) PCT Filed: May 22, 2018

(86) PCT No.: PCT/CN2018/087807
§ 371 (c)(1),
(2) Date: Nov. 5, 2019

(87) PCT Pub. No.: WO2018/214867
PCT Pub. Date: Nov. 29, 2018

(65) Prior Publication Data
US 2020/0071302 A1  Mar. 5, 2020

(30) Foreign Application Priority Data
May 24, 2017 (CN) .......................... 201710378071.9

(51) Int. Cl.
*C07D 401/14* (2006.01)
*A61P 35/00* (2006.01)
*C07D 413/14* (2006.01)

(52) U.S. Cl.
CPC ............ *C07D 401/14* (2013.01); *A61P 35/00* (2018.01); *C07D 413/14* (2013.01)

(58) Field of Classification Search
CPC ...... C07D 401/14; C07D 413/14; A61P 35/00
See application file for complete search history.

(56) References Cited

U.S. PATENT DOCUMENTS

| | | | | |
|---|---|---|---|---|
| 2010/0249149 A1* | 9/2010 | Allgeier | .................. | A61P 31/00 514/256 |
| 2014/0275016 A1* | 9/2014 | Flynn | .................... | C07D 401/14 514/210.18 |
| 2014/0275080 A1* | 9/2014 | Flynn | ...................... | A61P 13/12 514/235.5 |
| 2014/0296252 A1* | 10/2014 | Flynn | .................... | C07D 413/14 514/253.09 |
| 2014/0315917 A1* | 10/2014 | Flynn | .................... | C07D 401/14 514/253.09 |
| 2020/0140431 A1* | 5/2020 | Zhang | ..................... | A61P 35/00 |
| 2020/0165254 A1* | 5/2020 | Zhao | ..................... | C07D 401/14 |
| 2020/0399265 A1* | 12/2020 | Liu | ....................... | C07D 487/10 |

FOREIGN PATENT DOCUMENTS

| WO | 2006/067445 A2 | 6/2006 | | |
|---|---|---|---|---|
| WO | 2014/145015 A2 | 9/2014 | | |
| WO | 2014/145023 A1 | 9/2014 | | |
| WO | 2014/145028 A2 | 9/2014 | | |
| WO | WO-2018233526 A1 * | 12/2018 | ........... | C07D 487/04 |

OTHER PUBLICATIONS

Hume; Blood 119, 2012, 1810-1820. DOI: 10.1182/blood-2011-09-379214 (Year: 2012).*
Norman; J. Med. Chem. 2012, 55, 5, 1858-1867. DOI: 10.1021/jm201330u (Year: 2012).*
Peyraud; Curr Oncol Rep 19, 2017, 70. DOI: 10.1007/s11912-017-0634-1 (Year: 2017).*
International Preliminary Report on Patentability, International Application PCT/CN2018/087807, dated Nov. 26, 2019, English Translation, 9 pages. (Year: 2019).*
Burns et al, "c-FMS inhibitors: a patent review," Expert Opinion on Therapeutic Patents, vol. 21, No. 2, pp. 147-165 (Feb. 2011).
Ries et al, "CSF-1/CSF-1R targeting agents in clinical development for cancer therapy," Current Opinion in Pharmacology, vol. 23, pp. 45-51 (Aug. 2015).
Kumar et al, "Current Diagnosis and Management of Immune Related Adverse Events (irAEs) Induced by Immune Checkpoint Inhibitor Therapy," Frontiers in Pharmacology, vol. 8, No. 49, pp. 1-14 (Feb. 2017).

(Continued)

*Primary Examiner* — Daniel R Carcanague
(74) *Attorney, Agent, or Firm* — Panitch Schwarze Belisario & Nadel LLP; Lars H. Genieser

(57) ABSTRACT

An N-(azaaryl)cyclolactam-1-carboxamide derivative having a structure of formula (I), a preparation method therefor, and a use thereof are disclosed in the application. Each substituent are defined in the specification and claims. The series of compounds of the application can be widely applied in the preparation of drugs for treating cancer, tumor, autoimmune disease, metabolic disease or metastatic disease, particularly for treating ovarian cancer, pancreatic cancer, prostate cancer, breast cancer, cervical cancer, glioblastoma, multiple myeloma, metabolic disease, neurodegenerative disease, primary tumor site metastasis or osseous metastasis cancer, and are expected to be developed into a new generation of CSF-1R inhibitor drugs.

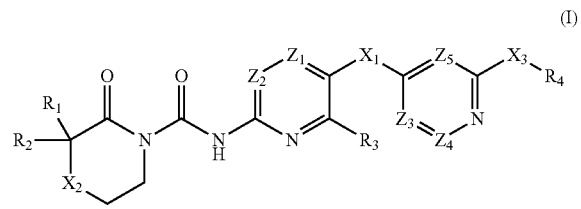

21 Claims, No Drawings

(56) References Cited

OTHER PUBLICATIONS

Adams et al, "Big opportunities for small molecules in immune-oncology," Nature Reviews Drug Discovery, vol. 14, No. 9, pp. 603-622 (Sep. 2015).

Blumenthal et al, "Approvals in 2016: the march of the checkpoint inhibitors," Nature Reviews Clinical Oncology, vol. 14, pp. 131-132 (2017).

Pyonteck et al, "CSF-1R inhibition alters macrophage polarization and blocks glioma progression," Nature Medicine, vol. 19, No. 10, pp. 1264-1272 (Oct. 2013).

Zhang et al, "Prognostic Significance of Tumor-Associated Macrophages in Solid Tumor: A Meta-Analysis of the Literature," Plos One, vol. 7, No. 12, p. e50946 (Dec. 2012).

Ries et al, "Targeting Tumor-Associated Macrophages with Anti-CSF-1R Antibody Reveals a Strategy for Cancer Therapy," Cancer Cell, vol. 25, No. 6, pp. 846-859 (Jun. 2014).

Int'l Search Report dated Aug. 20, 2018 in Int'l Application No. PCT/CN2018/087807.

Ciapetti et al., "Molecular Variations Based on Isosteric Replacements," The Practice of Medicinal Chemistry (Third Edition), pp. 290-342 (2008).

Extended European Search Report dated Jan. 22, 2021 in EP Application No. 18805288.0.

\* cited by examiner

N-(AZAARYL)CYCLOLACTAM-1-CARBOXAMIDE DERIVATIVE, PREPARATION METHOD THEREFOR, AND USE THEREOF

CROSS-REFERENCE TO RELATED APPLICATION

This application is a Section 371 of International Application No. PCT/CN2018/087807, filed May 22, 2018, which was published in the Chinese language on Nov. 29, 2018, under International Publication No. WO 2018/214867 A9, which claims priority under 35 U.S.C. § 119(b) to Chinese Patent Application No. 201710378071.9, filed on May 24, 2017, the disclosures of which are incorporated herein by reference in their entireties.

TECHNICAL FIELD

The present invention belongs to the field of pharmaceutical synthesis, and particularly relates to an N-(azaaryl) cyclolactam-1-carboxamide derivative, a preparation method therefor, and a use thereof.

BACKGROUND

CSF-1R (cFMS) stands for colony-stimulating factor 1 receptor. CSF-1R, as well as KIT, FLT3, and PDGFRA&B, belong to the type III growth hormone receptor family. This receptor is a membrane protein, and is expressed on the surface of macrophages and monocytes. The extracellular domain of this receptor is capable of binding to the macrophage colony-stimulating factor, and the intracellular domain tyrosine kinase can activate downstream cell growth and proliferation signal pathways for macrophages and monocytes, such as MAPK, PI3K, etc. Therefore, CSF-1R signal pathway is critical for the development and differentiation of macrophages and monocytes, and the physiological function of tumor-associated macrophages (TAMs) (Expert Opin Ther Pat. 2011 February; 21(2):147-65.; Curr Opin Pharmacol. 2015 August; 23:45-51.).

In recent years, immune checkpoint inhibitors have become popular in the field of cancer treatment. This type of drugs significantly inhibited the growth of tumors clinically, and some patients have complete regression after treatment. However, clinical data have shown that only about 30% of patients responded to immune checkpoint inhibitors, such as anti-PD-1/PD-L1 antibody. Due to the lack of related biomarkers, how to select patients who may respond remains an unsolved problem. Additionally, immune checkpoint inhibitors will cause immune-related side effects in clinical practice, and therefore, experienced clinicians and medical institutions are needed to conduct such treatment. Therefore, how to combine immune checkpoint inhibitors with small-molecule inhibitors to reduce side effects and increase the response rate of cancer patients is an urgent problem to be solved in the research and development of antineoplastic drugs (Front Pharmacol. 2017 Feb. 8; 8:49.; Nat Rev Drug Discov. 2015 September; 14(9):603-22.; Nature Reviews Clinical Oncology 14, 131-132 (2017)).

With the advancement in cancer immunotherapy in recent years, tumor-associated macrophages (TAMs) and myeloid-derived suppressor cells (MDSCs) are considered to contribute directly to the formation of an immunosuppressive tumor microenvironment and the angiogenesis process supporting tumor growth. Meanwhile, clinical studies have shown that the number of TAMs is negatively correlated with the prognosis of cancer patients. The result of an efficacy study in mice proved that inhibiting the CSF-1R signal pathway can remarkably decrease the number of immunosupppresive macrophages in tumors, and increase the content of CD8-positive T cells. These experiment results demonstrated that CSF-1R small-molecule inhibitors may reverse the immunosuppressive microenvironment in the tumor, promote the activation of the immune system, and prolong the lifespan of cancer patients (Nat Med. 2013 October; 19(10):1264-72; PLoS ONE 7(12): e50946,; Cancer Cell. 2014 Jun. 16; 25(6):846-59.).

The selectivity is a common problem for small-molecule kinase inhibitors, especially for the related members in the same kinase family. Because small-molecule drugs in the present patent may be used in combination with other immune checkpoint inhibitors in future clinical studies, the inventors attempted to improve the inhibitory effect on CSF-1R target and the selectivity of related kinase receptors, prolong the therapeutic window, and reduce the probability of clinical toxic and side effects by optimizing the molecular structure in the process of long-term research. Therefore, how to find CSF-1R small-molecule inhibitors with higher selectivity and meet the domestic demand on target and immune therapies for cancers, such as lung cancer, breast cancer, prostate cancer, ovarian cancer, cervical cancer, melanoma, pancreatic cancer, head and neck cancer, glioma, and giant cell tumor of tendon sheath, have become an important part of the current researches of scientists.

SUMMARY

The objective of the present invention is to provide a CSF-1R small-molecule inhibitor.

The first aspect of the present invention provides a compound of formula (I), a stereoisomer or pharmaceutically acceptable salt thereof:

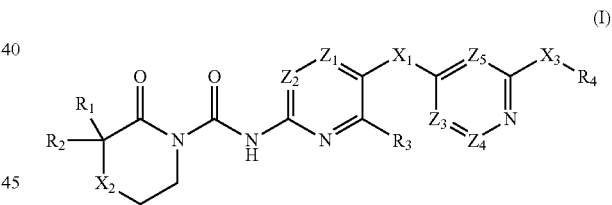

Wherein, $X_1$, $X_2$ and $X_3$ are each independently bond, —O—, —S—, —$(CR_5R_6)_m$—, —$N(R_7)$—, —$N(R_8)$—C(O)— and —C(O)—$N(R_8)$—;

$Z_1$, $Z_2$, $Z_3$, $Z_4$ and $Z_5$ are each independently $C(R_9)$ or N;

$R_1$ and $R_2$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=$NR_{10}$)$R_{11}$, —$C_{0-8}$—B(OR_{12})_2$, —$C_{0-8}$—P(O)($R_{13}$)$_2$, —$C_{0-8}$—S(O)$_r$$R_{11}$, —$C_{0-8}$—O—$R_{12}$, —$C_{0-8}$—C(O)O$R_{12}$, —$C_{0-8}$—C(O)$R_{13}$, —$C_{0-8}$—O—C(O)$R_{13}$, —$C_{0-8}$—$NR_{14}R_{15}$, —$C_{0-8}$—C(IO)$NR_{14}R_{15}$ and —$C_{0-8}N(R_{14})$—C(O)$R_{13}$, or, $R_1$ and $R_2$, together with the carbon atom directly attached thereto, form carbonyl, $C_{3-10}$ cycloalkyl or 3-10 membered heterocyclyl, above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—C(O)$_r$R$_{11}$, —$C_{0-8}$—C(O)R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)-C(O)R$_{13}$;

R$_3$ and R$_9$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=NR$_{10}$)R$_{11}$, —$C_{0-8}$—B(OR$_{12}$)$_2$, —$C_{0-8}$—P(O)(R$_{13}$)$_2$, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$, above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$;

R$_4$ is selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ to cycloalkyl, 3-10 membered heterocyclyl, $C_{5-10}$ aryl, 5-10 membered heteroaryl, —$C_{0-8}$—S(O)$_r$R$_{11}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$, above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{2-8}$ haloalkyl, $C_{3-10}$ cycloalkyl, 3-10 membered heterocyclyl, $C_{5-10}$ aryl, 5-10 membered heteroaryl, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$, above groups are optionally more further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)R$_{11}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$, wherein cycloalkyl, heterocyclyl, aryl and heteroaryl are optionally more further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—C(O)OR$_{12}$, —$C_{0-8}$—C(O)R$_{12}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$;

R$_5$ and R$_6$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl. $C_{5-10}$ aryl, 5-10 membered heteroaryl, —$C_{0-8}$—S(O)(=NR$_{10}$)R$_{11}$, —$C_{0-8}$—B(OR$_{12}$)$_2$, —$C_{0-8}$—P(O)(R$_{13}$)$_2$, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, -$C_{0-8}$—C(O)NR$_{14}$R$_{15}$ and —$C_{0-8}$—N(R$_{14}$)—C(O)R$_{13}$, or, R$_5$ and R$_6$, together with the carbon atom directly attached thereto, form carbonyl, $C_{3-10}$ cycloalkyl or 3-10 membered heterocyclyl, above groups are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—C(O)OR$_{12}$, —$C_{0-8}$—(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$;

R$_7$ and R$_8$ are each independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and -NR$_{14}$R$_{15}$, above groups are optionally further substituted by one or more substituents selected from the group consisting of deuterium, halogen, cyano, nitro, azido. $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and -$C_{0-8}$—N(R$_{14}$)—C(O)R$_{13}$;

each R$_{10}$ is independently selected from the group consisting of hydrogen, deuterium, $C_{1-8}$ alkyl, $C_{3-10}$ cycloalkyl $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$;

each R$_{11}$ is independently selected from the group consisting of hydrogen, deuterium, hydroxy, $C_{1-8}$ alkyl, $C_{1-8}$ alkoxy, $C_{2-8}$ alkenyl, $C_{3-10}$ cycloalkyl, $C_{3-10}$ cycloalkyloxy 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$, above groups are optionally further substituted by one or more substituents selected from the group consisting of deuterium, halogen, hydroxy, carbonyl, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heroalyl, 5-10 membered heteroaryloxy and —NR$_{14}$R$_{15}$;

each R$_{12}$ is independently selected from the group consisting of hydrogen, deuterium, $C_{1-8}$ alkyl, $C_{2-8}$ alkenyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, hydroxy, carbonyl, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$;

each R$_{13}$ is independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$, above groups are optionally further substituted by one or more substituents selected from the group consisting of deuterium halogen, hydroxy, cyano, $C_{1-8}$ alkyl. $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$;

each of R$_{14}$ and R$_{15}$ is independently selected from the group consisting of hydrogen, deuterium, hydroxy, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, sulfonyl, methanesulfonyl, isopropylsulfonyl, cyclopropylsulfonyl, p-toluenesulfonyl, amino, monoalkylamino, dialkylamino and $C_{1-8}$ alkanoyl, above groups are optionally further substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

or, $R_{14}$ and $R_{15}$, together with nitrogen atom directly attached thereto, form 5-10 membered heterocyclyl, above groups are optionally further substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

m is 0, 1, 2, 3, 4 or 5;

and r is 0, 1 or 2

As a preferred embodiment, in the compound of formula (I), the stereoisomer or pharmaceutically acceptable salt thereof, $R_3$ is selected from the group consisting of hydrogen, deuterium, fluorine, chlorine, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)(=$NR_{10}$)$R_{11}$, —$C_{0-4}$—B($OR_{12}$)$_2$, —$C_{0-4}$—P(O)($R_{13}$)$_2$, —$C_{0-4}$—S(O)$_r$$R_{11}$, —$C_{0-4}$—O—$R_{12}$, —$C_{0-4}$—C(O)$OR_{12}$, —$C_{0-4}$—O—C(O)$R_{13}$, —$C_{0-4}$—C(O)$R_{13}$, —$C_{0-4}$—$NR_{14}R_{15}$ and —$C_{0-4}$—N($R_{14}$)—C(O)$R_{13}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{11}$, —$C_{0-4}$—O—$R_{12}$, —$C_{0-4}$—C(O)$OR_{12}$, —$C_{0-4}$—C(O)$R_{13}$, —$C_{0-4}$—O—C(O)$R_{13}$, —$C_{0-4}$—$NR_{14}R_{15}$, —$C_{0-4}$—C(O)$NR_{14}R_{15}$ and —$C_{0-4}$—N($R_{14}$)—C(O)$R_{13}$, wherein $R_{10}$, $R_{11}$, $R_{12}$, $R_{13}$, $R_{14}$, $R_{15}$, and r are defined as above.

As a further preferred embodiment, in the compound of formula (1), the stereoisomer or pharmaceutically acceptable salt thereof, $R_3$ is selected from the group consisting of hydrogen, deuterium, fluorine, chlorine, cyano, nitro, azido, methyl, ethyl, isopropyl, allyl, ethynyl, cyclopropyl, cyclopropylmethyl, oxa-cyclobutyl, aza-cyclopentyl, aza-cyclohexyl, phenyl, diazole, triazole, methanesulfonyl, isopropylsulfonyl, aminosulfonyl, methoxy, ethoxy, isopropoxy, methoxyethyl, ethoxyethyl, hydroxymethyl, hydroxyethyl, cyanomethyl, trifluoromethyl trideuteriomethyl, difluoromethyl, dideuteriomethyl, methoxy carbonyl, ethoxycarbonyl, acetyl, acetoxy, acetoxymethyl, amino, dimethylamino, aminomethyl, aminocarbonyl, dimethylaminocarbonyl and acetylamino.

As a more further preferred embodiment, in the compound of formula (1), the stereoisomer or pharmaceutically acceptable salt thereof, $R_3$ is selected from the group consisting of hydrogen, deuterium, fluorine, chlorine, cyano, methyl, ethyl, isopropyl, cyclopropyl, cyclopropylmethyl, oxa-cyclobutyl, methoxy, ethoxy, isopropoxy, methoxyethyl, ethoxyethyl, hydroxymethyl, hydroxy ethyl, cyanomethyl, trifluoromethyl, trideuteriomethyl, difluoromethyl, dideuteriomethyl, amino and dimethylamino.

As a more further preferred embodiment, in the compound of formula (I), the stereoisomer or pharmaceutically acceptable salt thereof, $R_3$ is selected from the group consisting of hydrogen, deuterium, fluorine, chlorine, cyano, methyl, ethyl, cyclopropyl cyclopropylmethyl methoxy, ethoxy, trifluoromethyl, trideuteriomethyl, difluoromethyl, dideuteriomethyl, amino and dimethylamino.

As a preferred embodiment, in the compound of formula (I), the stereoisomer or pharmaceutically acceptable salt thereof, $R_1$ and $R_2$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)(=$NR_{10}$)$R_{11}$, —$C_{0-4}$—B($OR_{12}$)$_2$, —$C_{0-4}$—P(O)($R_{13}$)$_2$, —$C_{0-4}$—S(O)$_r$$R_{11}$, —$C_{0-4}$—O—$R_{12}$, —$C_{0-4}$—C(O)$R_{12}$, —$C_{0-4}$—C(O)$R_{13}$, —$C_{0-4}$—O—C(O)$R_{13}$, —$C_{0-4}$—$NR_{14}R_{15}$, —$C_{0-4}$—C(O)$NR_{14}R_{15}$ and —$C_{0-4}$—N($R_{14}$)—C(O)$R_{13}$, or, $R_1$ and $R_2$, together with the carbon atom directly attached thereto, form carbonyl, $C_{3-8}$ cycloalkyl or 3-8 membered heterocyclyl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—C(O)$_r$$R_{12}$, —$C_{0-4}$—C(O)$R_{13}$, —$C_{0-4}$—O—C(O)$R_{13}$, —$C_{0-4}$—$NR_{14}R_{15}$, —$C_{0-4}$—C(O)$NR_{14}R_{15}$ and —$C_{0-4}$—N($R_{14}$)—C(O)$R_{13}$;

wherein, $R_{10}$, $R_{11}$, $R_{12}$, $R_{13}$, $R_{14}$, $R_{15}$ and r are defined as above.

As a further preferred embodiment, in the compound of formula (I), the stereoisomer or pharmaceutically acceptable salt thereof, $R_1$ and $R_2$ are each independently selected from the group consisting of hydrogen, deuterium, hydroxy, methyl, ethyl, propyl, isopropyl, allyl, ethynyl, cyclopropyl, cyclopropyl methyl, oxa-cyclobutyl, aza-cyclopentyl, aza-cyclohexyl, phenyl, diazole, triazole, methoxy, ethoxy, isopropoxy, phenylmethoxy, methoxyethyl, ethoxyethyl, hydroxymethyl, hydroxyethyl, cyanomethyl, trifluoromethyl, trideuteriomethyl, difluoromethyl, dideuteriomethyl, methoxycarbonyl, ethoxycarbonyl, acetyl, acetoxy, acetoxy methyl, amino, dimethylamino, aminomethyl, aminocarbonyl, dimethylaminocarbonyl and acetylamino, or, $R_1$ and $R_2$, together with the carbon atom directly attached thereto, form carbonyl, $C_{3-6}$ cycloalkyl, or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, isopropyl, allyl, ethynyl, cyclopropyl, cyclopropylmethyl, oxa-cyclobutyl, aza-cyclopentyl, aza-cyclohexyl, phenyl, diazole, triazole, methoxy, ethoxy, isopropoxy, methoxyethyl, ethoxyethyl, hydroxymethyl, hydroxyethyl, cyanomethyl, trifluoromethyl, difluoromethyl, methoxycarbonyl, ethoxycarbonyl, acetyl, acetoxy, acetoxymethyl, amino, dimethylamino, aminomethyl, aminocarbonyl, dimethylaminocarbonyl and acetylamino.

As a more further preferred embodiment, in the compound of formula (I), the stereoisomer or pharmaceutically acceptable salt thereof, $R_1$ and $R_2$ are each independently selected from the group consisting of hydrogen, deuterium, hydroxy, methyl, ethyl, propyl, cyclopropyl, cyclopropylmethyl, methoxy, ethoxy, phenylmethoxy, methoxyethyl, hydroxymethyl, cyanomethyl, trifluoromethyl, trideuteriomethyl, difluoromethyl, dideuteriomethyl and aminomethyl, or, $R_1$ and $R_2$, together with the carbon atom directly attached thereto, form carbonyl, $C_{3-6}$ cycloalkyl, or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, cyclopropyl, cyclopropylmethyl, methoxy, ethoxy, methoxyethyl, hydroxymethyl, cyanomethyl, trifluoromethyl, difluoromethyl and aminomethyl.

As a further preferred embodiment, the compound of formula (I) is a compound with the structure shown as formula (IIa):

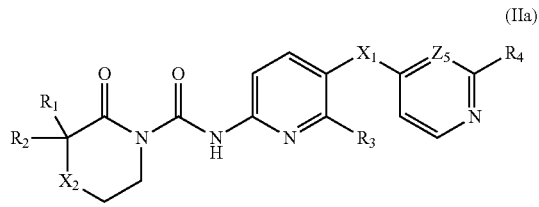

(IIa)

wherein, $X_1$ is —O— or —$(CR_5R_6)$—; $X_2$ is bond, —O—, —$(CR_5R_6)$— or —$N(R_7)$—;

$R_1$ and $R_2$ are each independently selected from the group consisting of hydrogen, deuterium, hydroxy, methyl, ethyl, propyl, cyclopropyl, cyclopropylmethyl, methoxy, ethoxy, phenylmethoxy, methoxyethyl, hydroxymethyl, cyanomethyl, trifluoromethyl, trideuteriomethyl, difluoromethyl, dideuteriomethyl and aminomethyl, or, $R_1$ and $R_2$, together with the carbon atom directly attached thereto, form carbonyl, $C_{3-6}$ cycloalkyl or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, cyclopropyl, cyclopropylmethyl, methoxy, ethoxy, methoxyethyl, hydroxymethyl, cyanomethyl, trifluoromethyl, difluoromethyl and aminomethyl;

$R_3$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_4$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)$_r$$R_{11}$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$ and —$C_{0-4}$—N$R_{14}R_{15}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{11}$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$, above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-3}$ aryl, 5-8 membered heteroaryl, —$C_{0-4}$—S(O)$_r$$R_{11}$, —$C_{0-4}$—O—$R_{12}$, —$C_{0-4}$—C(O)$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$, wherein cycloalkyl, heterocyclyl, aryl, and heteroaryl are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{11}$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$;

$R_5$ and $R_6$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-3}$ cycloalkyl, 3-8 membered heterocyclyl, $C_{5-3}$ aryl, 5-8 membered heteroaryl, —$C_{0-4}$—S(O)(=N$R_{10}$)$R_{11}$, —$C_{0-4}$—B(O$R_{12}$)$_2$, —$C_{0-4}$—P(O)($R_{13}$)$_2$, —$C_{0-4}$—S(O)$_r$$R_{11}$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$, or, $R_5$ and $R_6$, together with the carbon atom directly attached thereto, form carbonyl. $C_{3-8}$ cycloalkyl, or 3-8 membered heterocyclyl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{11}$, —$C_{0-4}$—O—$R_{12}$, —$C_{0-4}$—C(O)O$R_{12}$, —$_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$;

$R_7$ is selected from the group consisting of hydrogen, deuterium, $C_{1-4}$ alkyl, $C_{3-8}$ cycloalkyl. 3-8 membered heterocyclyl, $C_{5-8}$ aryl and 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$;

Wherein, $Z_5$, $R_{10}$, $R_{11}$, $R_{12}$, $R_{13}$, $R_{14}$, $R_{15}$, and r are defined as those in the compound of formula (1).

As a more further preferred embodiment, in the compound of formula (I), the stereoisomer or pharmaceutically acceptable salt thereof, $X_1$ is —O— or —$(CR_5R_6)$—; $X_2$ is bond, —O—, —$CH_2$— or —$N(R_7)$—;

$R_1$ and $R_2$ are each independently selected from the group consisting of hydrogen, deuterium, hydroxy, methyl, ethyl, propyl, cyclopropyl. cyclopropylmethyl, methoxy, ethoxy, phenylmethoxy, methoxyethyl, hydroxymethyl, cyanomethyl, trifluoromethyl, trideuteriomethyl, difluoromethyl, dideuteriomethyl and aminomethyl, or, $R_1$ and $R_2$, together with the carbon atom directly attached thereto, form carbonyl, $C_{3-6}$ cycloalkyl or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, cyclopropyl, cyclopropylmethyl, methoxy, ethoxy, methoxyethyl, hydroxymethyl, cyanomethyl, trifluoromethyl, difluoromethyl and aminomethyl;

$R_3$ is the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_4$ is $C_{5-8}$ aryl, 5-8 membered heteroaryl or —N$R_{14}R_{15}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$NR$_{14}$R$_{15}$, —$C_{0-4}$C(O)NR$_{14}$R$_{15}$ and —$C_{0-4}$—N(R$_{14}$)—C(O)R$_{13}$, above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—O—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and 13$C_{0-4}$—N(R$_{14}$)—C(O)R$_{13}$, wherein, the cycloalkyl, heterocyclyl, aryl, and heteroaryl are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$;

$R_5$ and $R_6$ are each independently selected from the group consisting of hydrogen, deuterium, fluorine, chlorine, methyl, trifluoromethyl, trideuteriomethyl, ethyl, isopropyl, cyclopropyl, cyclopropylmethyl, methoxy and methoxyethyl, or, $R_5$ and $R_6$, together with the carbon atom directly attached thereto, form carbonyl, cyclopropyl, cyclobutyl or oxa-cyclobutyl;

$R_7$ is selected from the group consisting of hydrogen, deuterium, methyl, ethyl, cyclopropyl, cyclopropylmethyl, trifluoromethyl and trideuteriomethyl;

$R_9$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

wherein, $R_{11}$, $R_{12}$, $R_{13}$, $R_{14}$, $R_{15}$, and r are defined as above.

As a more further preferred embodiment, in the compound of formula (I), the stereoisomer or pharmaceutically acceptable salt thereof, $X_1$ is —O— or —CH$_2$—; $X_2$ is bond, —O— or —CH$_2$—;

$R_1$ and $R_2$ are each independently selected from the group consisting of hydrogen, deuterium, hydroxy, methyl, ethyl, propyl, cyclopropyl, cyclopropylmethyl, methoxy, ethoxy, phenylmethoxy, methoxyethyl, hydroxymethyl, cyanomethyl, trifluoromethyl, trideuteriomethyl, difluoromethyl, dideuteriomethyl and aminomethyl, or, $R_1$ and $R_2$, together with the carbon atom directly attached thereto, form $C_{3-6}$ cycloalkyl;

$R_3$ is selected from the group consisting of hydrogen, deuterium, methyl, ethyl, cyclopropyl, cyclopropylmethyl, trifluoromethyl, trideuteriomethyl, difluoromethyl and dideuteriomethyl;

$R_9$ is selected from the group consisting of hydrogen, deuterium, fluorine, chlorine, cyano, cyclopropyl and cyclopropylmethyl.

As a more further preferred embodiment, in the compound of formula (I), the stereoisomer or pharmaceutically acceptable salt thereof, $R_4$ is selected from the group consisting of $C_{5-8}$ aryl, 5-8 membered heteroaryl and —NR$_{14}$R$_{15}$, wherein the $C_{5-8}$ aryl and 5-8 membered heteroaryl are selected from the following structures:

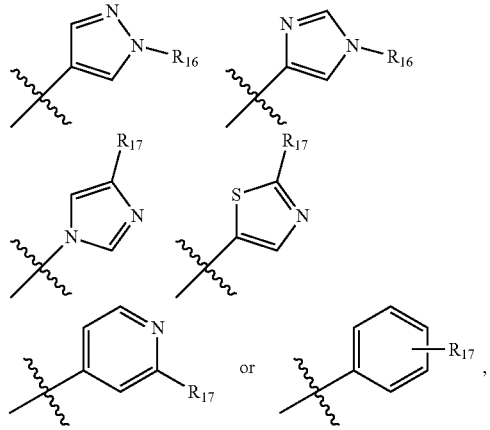

wherein, each $R_{16}$ is independently selected from the group consisting of hydrogen deuterium $C_{1-4}$ alkyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, $C_{0-4}$—C(O)OR$_{12}$ and —$C_{0-4}$—C(O)R$_{13}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—COR$_{13}$, —$C_{0-4}$—NR$_{14}$R$_{15}$ and —$C_{0-4}$—C(O)NR$_{14}$R$_{15}$ and —$C_{0-4}$—N(R$_{14}$)—C(O)R$_{13}$, wherein the cycloalkyl, heterocyclyl, aryl, and heteroaryl are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$;

each $R_{17}$ is independently selected from the group consisting of hydrogen, deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$13NR$_{14}$R$_{15}$, —$C_{0-4}$—C(O)NR$_{14}$R$_{15}$ and —$C_{0-4}$—N(R$_{14}$)—C(O)R$_{13}$, wherein cycloalkyl, heterocyclyl, aryl, and heteroaryl are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$;

wherein, $R_{11}$, $R_{12}$, $R_{13}$, $R_{14}$, $R_{15}$, and r are defined as above.

As a more further preferred embodiment, in the compound of formula (I), the stereoisomer or pharmaceutically acceptable salt thereof, wherein each $R_{16}$ is independently selected from the group consisting of hydrogen, deuterium, $C_{1-4}$ alkyl, $C_{3-6}$ cycloalkyl, 3-6 membered heterocyclyl, phenyl and 5-6 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, haloalkyl, $C_{3-8}$ cycloalkyl, 3-8 membered heterocyclyl, $C_{5-8}$ aryl, 5-8 membered heteroaryl, —$C_{0-4}$—S(O)$_r R_{11}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$;

each $R_{17}$ is independently selected from the group consisting of hydrogen, deuterium, fluorine, chlorine, cyano, nitro, azido, methyl, ethyl, isopropyl, allyl, ethynyl, cyclopropyl, cyclopropylmethyl, coxa-cyclobutyl, aza-cyclopentyl, aza-cyclohexyl, phenyl, diazole, triazole, methanesulfonyl, isopropylsulfonyl, aminosulfonyl, methoxy, ethoxy, isopropoxy, methoxyethyl, ethoxyethyl, hydroxymethyl, hydroxyethyl, cyanomethyl, trifluoromethyl, trideuteriomethyl, difluoromethyl, dideuteriomethyl, methoxycarbonyl, ethoxycarbonyl, acetyl, acetoxy, acetoxymethyl, amino, dimethylamino, aminomethyl, aminocarbonyl, dimethylaminocarbonyl and acetylamino;

wherein, $R_{11}$, $R_{12}$, $R_{13}$, $R_{14}$, $R_{15}$ and r are defined as above.

As the most preferred embodiment, the compound of formula (I), a stereoisomer or pharmaceutically acceptable salt thereof includes, but is not limited to the following specific compounds:

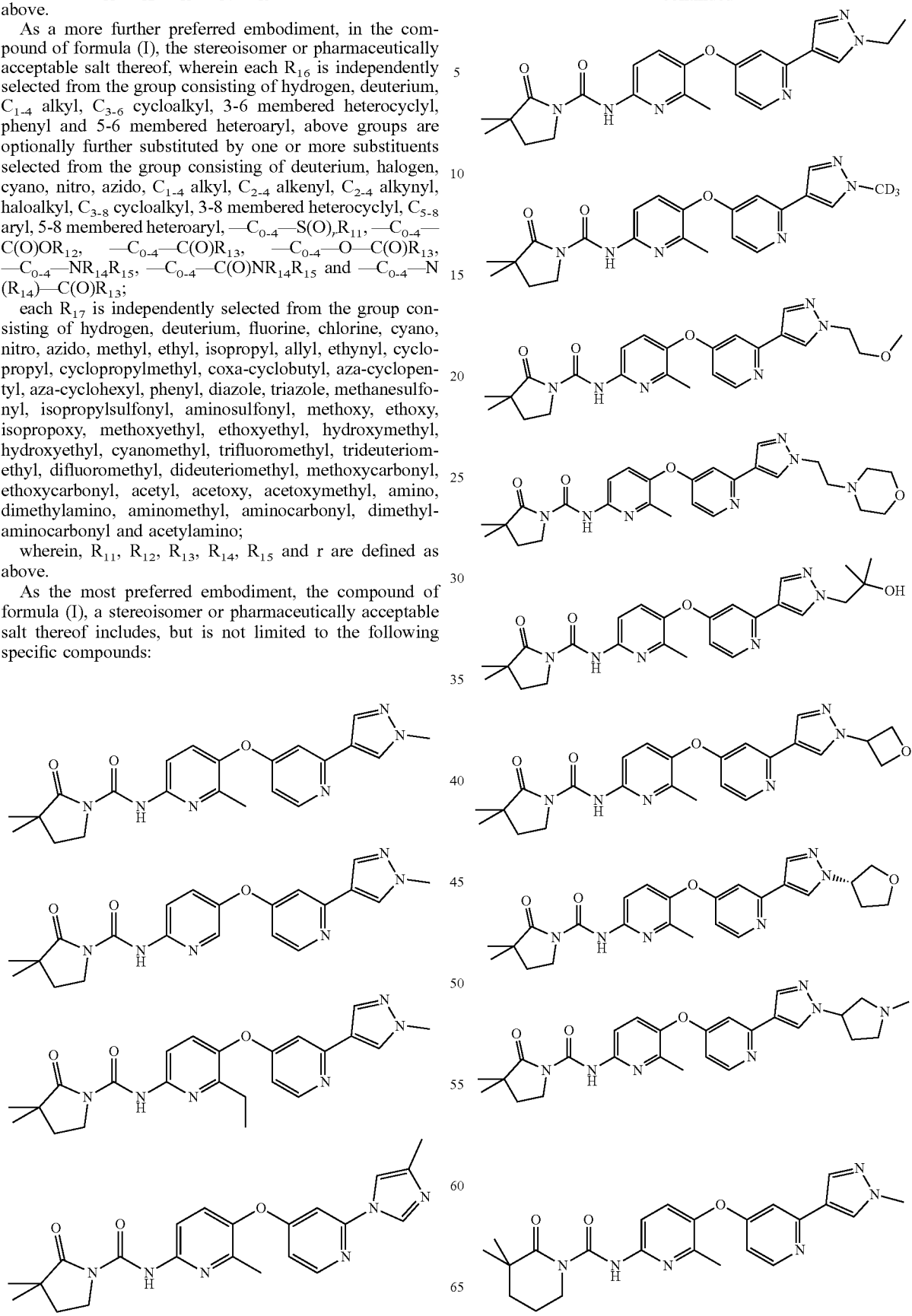

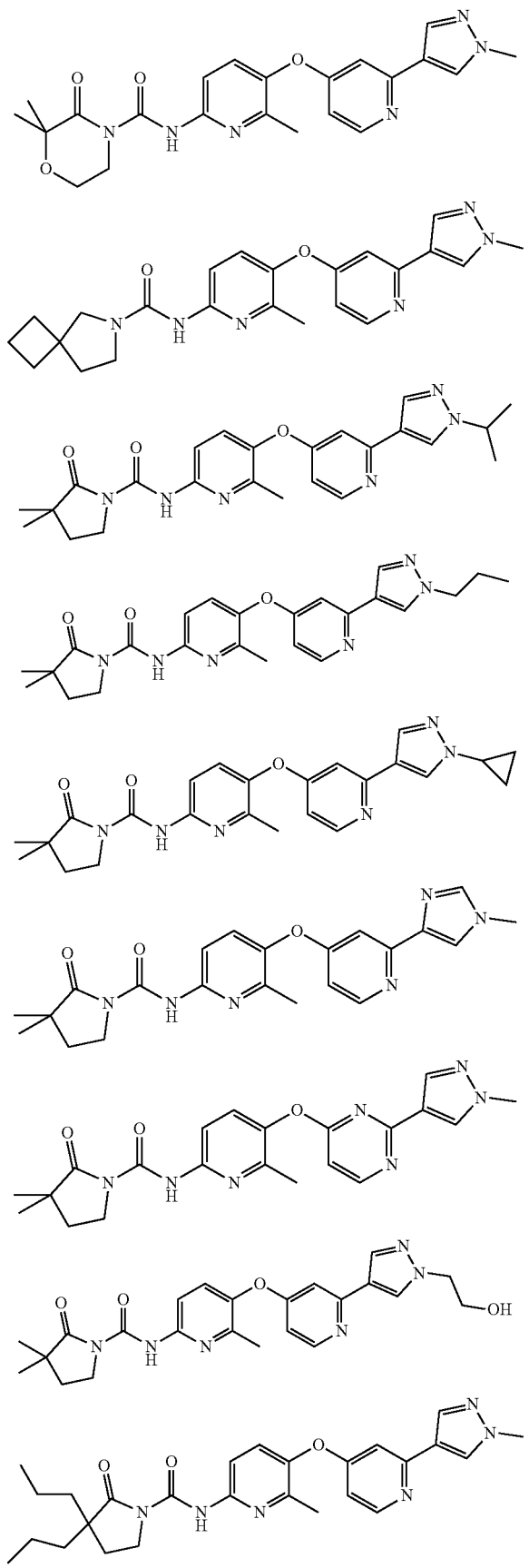
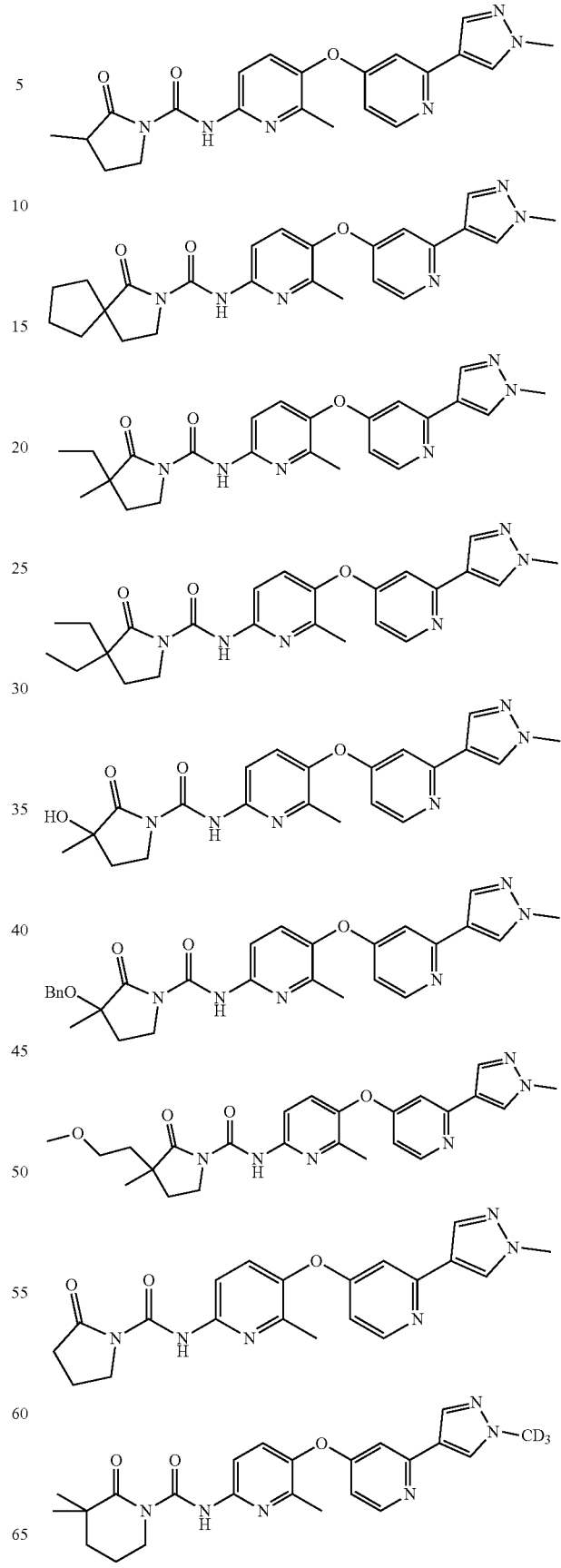

-continued

[chemical structures]

As a further preferred embodiment, the compound of formula (I) is a compound having formula (IIb):

(IIb)

[structure]

wherein, $X_3$ is —C(O)—N($R_8$)— or —N($R_8$)—C(O)—;
$R_1$ and $R_2$ are each independently selected from the group consisting of hydrogen, deuterium, hydroxy, methyl, ethyl, propyl, cyclopropyl, cyclopropylmethyl, methoxy, ethoxy, methoxyethyl, hydroxymethyl, cyanomethyl, trifluoromethyl, trideuteriomethyl, difluoromethyl, dideuteriomethyl and aminomethyl, or, $R_1$ and $R_2$, together with the carbon atom directly attached thereto, form carbonyl, $C_{3-6}$ cycloalkyl or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, cyclopropyl, cyclopropylmethyl, methoxy, ethoxy, methoxyethyl, hydroxymethyl, cyanomethyl, trifluoromethyl, difluoromethyl and aminomethyl;

$R_3$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_4$ is selected from the group consisting of hydrogen, deuterium, $C_{1-4}$ alkyl, $C_{3-8}$ cycloalkyl, 3-8 membered heterocyclyl, $C_{5-8}$ aryl, 5-8 membered heteroaryl, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$ and —$C_{0-4}$—N$R_{14}R_{15}$, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_rR_{11}$, —$C_{0-4}$—O—$R_{12}$, —$C_{0-4}$—C(O)O$R_{12}$, —$C_{0-4}$—(O)$R_{13}$, —$C_{0-4}$—O—C(O)$R_{13}$, —$C_{0-4}$—O—N$R_{14}R_{15}$, —$C_{0-4}$—C(O)N$R_{14}R_{15}$ and —$C_{0-4}$—N($R_{14}$)—C(O)$R_{13}$;

$R_8$ is selected from the group consisting of hydrogen, deuterium, methyl, trifluoromethyl, trideuteriomethyl, cyclopropyl and cyclopropylmethyl;

Wherein, $R_{11}$, $R_{12}$, $R_{13}$, $R_{14}$, $R_{15}$, and r are defined as those in the compound of formula (I).

As a more further preferred embodiment, in the compound of formula (I), the stereoisomer or pharmaceutically acceptable salt thereof, $R_1$ and $R_2$ are each independently selected from the group consisting of hydrogen, deuterium, hydroxy, methyl, ethyl, propyl, cyclopropyl, cyclopropylmethyl, hydroxymethyl, cyanomethyl, trifluoromethyl, trideuteriomethyl, difluoromethyl and dideuteriomethyl;

$R_3$ is selected from the group consisting of hydrogen, deuterium, methyl, ethyl, cyclopropyl, cyclopropylmethyl, trifluoromethyl, trideuteriomethyl, difluoromethyl and dideuteriomethyl;

$R_4$ is selected from the group consisting of $C_{1-4}$ alkyl, $C_{3-8}$ cycloalkyl and 3-8 membered heterocyclyl, above groups are optionally further substituted by one or more substituents selected from the group consisting of deuterium, $C_{1-4}$ alkyl, $C_{1-4}$ haloalkyl, $C_{3-8}$ cycloalkyl, 3-8 membered heterocyclyl, $C_{5-8}$ aryl and 5-8 membered heteroaryl;

$R_8$ is selected from the group consisting of hydrogen, deuterium, methyl, cyclopropyl and cyclopropylmethyl.

As the most preferred embodiment, the compound of formula (I), the stereoisomer or pharmaceutically acceptable salt thereof includes, but is not limited to the following specific compounds:

[chemical structures]

-continued

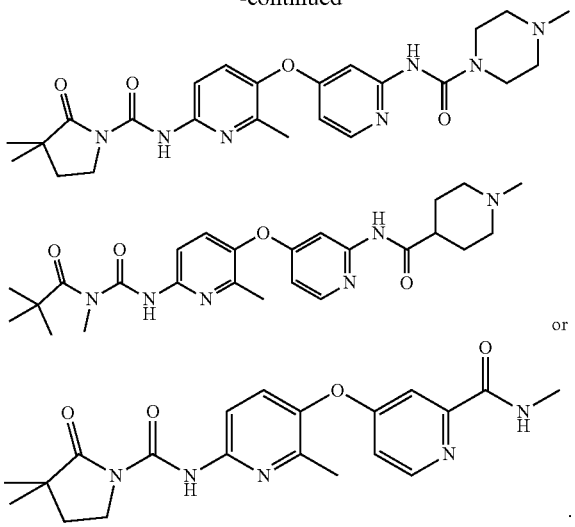

The second aspect of the present invention provides a process for preparing the compound of formula (I) and the stereoisomer or pharmaceutically acceptable salt thereof, comprising the following steps: the compound of formula (I) is synthesized through a condensation reaction of the compound of formula (Ia) or an acidic salt thereof and the compound of formula (Ib), and the reaction equation is as follows:

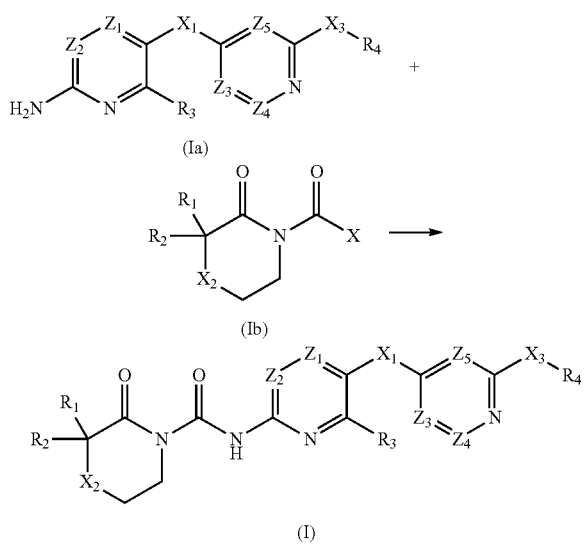

wherein, X is halogen or carboxyl, preferably chlorine or bromine; $X_1$, $X_2$, $X_3$, $Zr$, $Z_2$, $Z_3$, $Z_4$, $Z_5$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, m, and r are defined as those in the compound of formula (I).

The third aspect of the present invention provides a pharmaceutical composition, comprising the compound of formula (I), the stereoisomer or pharmaceutically acceptable salt thereof, and a pharmaceutically acceptable carrier.

The fourth aspect of the present invention provides use of the compound of formula (I), the stereoisomer or pharmaceutically acceptable salt thereof, or the above pharmaceutical composition in the preparation of medicament for treating cancer, tumor, autoimmune disease, metabolic disease or metastatic disease.

The fifth aspect of the present invention provides use of a compound of formula (I), the stereoisomer or pharmaceutically acceptable salt thereof, the above pharmaceutical composition in the preparation of medicament for treating ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia.

Preferably uses in the preparation of medicament for treating ovarian cancer, pancreatic cancer, prostate cancer, breast cancer, cervical cancer, glioblastoma, multiple myeloma, metabolic disease, neurodegenerative disease, primary tumor site metastasis or osseous metastasis cancer.

The sixth aspect of the present invention provides the compound of formula (I), the stereoisomer or pharmaceutically acceptable salt thereof, the aforementioned pharmaceutical composition for use as a medicament for treating cancer, tumor, autoimmune disease, metabolic disease or metastatic disease.

The seventh aspect of the present invention provides the compound of formula. (I), the stereoisomer or pharmaceutically acceptable salt thereof, the aforementioned pharmaceutical composition for use as a medicament for treating ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia, preferably for used as a medicament for treating ovarian cancer, pancreatic cancer, prostate cancer, breast cancer, cervical cancer, glioblastoma, multiple myeloma, metabolic disease, neurodegenerative disease, primary tumor site metastasis or osseous metastasis cancer.

The eighth aspect of the present invention provides a method for treating cancer, tumor, autoimmune disease, metabolic disease or metastatic disease, comprising administering the compound of formula (I), the stereoisomer or pharmaceutically acceptable salt thereof, or the above pharmaceutical composition to a patient.

The ninth aspect of the present invention provides a method for treating ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia, comprising administering the compound of formula (I), the stereoisomer or pharmaceutically acceptable salt thereof, or the above pharmaceutical composition to a patient.

DETAILED DESCRIPTION OF EMBODIMENTS

After an extensive and intensive research, the inventors of the present invention develops a N-(azaaryl)cyclolactam-1-carboxamide derivative with the structure of formula (I) as well as a preparation method therefor, and a use thereof for the first time. With a strong inhibitory effect on the activity of CSF-1R kinase, the series of compounds of the present invention can be widely applied in the preparation of drugs for treating cancer, tumor, autoimmune disease, metabolic disease or metastatic disease, particularly for treating ovarian cancer, pancreatic cancer, prostate cancer, breast cancer, cervical cancer, glioblastoma, multiple myeloma, metabolic disease, neurodegenerative disease, primary tenor site metastasis or osseous metastasis cancer, and are expected to be developed into anew generation of CSF-1R inhibitor drugs. The present invention is achieved on this basis.

Detailed description: unless otherwise stated, the following terms used in the specification and claims have the following meanings.

"Alkyl" refers to linear or branched saturated aliphatic alkyl groups, for example, "$C_{1-8}$ alkyl" means a linear alkyl or a branched alkyl containing 1 to 8 carbon atoms, which includes, but is not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof, etc.

Alkyl may be optionally substituted or unsubstituted, and when it is substituted, the substituent is preferably one or more of groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$.

"Cycloalkyl" refers to monocyclic or polycyclic hydrocarbon substituents that are saturated or partially unsaturated, for example, "$C_{3-10}$ cycloalkyl" means a cycloalkyl containing 3 to 10 carbon atoms, which may be monocyclic cycloalkyl and polycyclic cycloalkyl, wherein, monocyclic cycloalkyl includes but is not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl, etc.

Polycyclic cycloalkyl includes spirocycloalkyl, fused cycloalkyl and bridged cycloalkyl. "Spirocycloalkyl" refers to a polycyclic group in which a carbon atom (called spiro-atom) is shared among monocyclic rings, wherein those rings may contain one or more double bonds, but none of them has a fully conjugated a-electron system. According to the number of the spiro-atoms shared among the rings, the spirocycloalkyl may be monospirocycoalkyl, bispirocycloalkyl or polyspirocycloalkyl, including but not limited to:

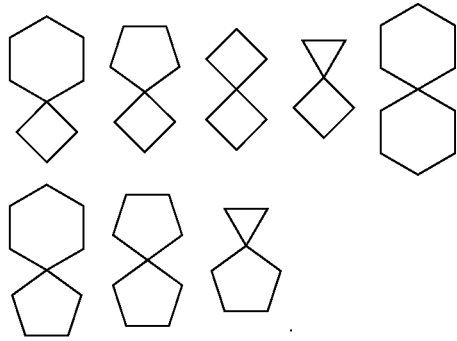

"Fused cycloalkyl" refers to an all-carbon polycyclic group in which each ring share a pair of adjacent carbon atoms with the other rings in the system, wherein one or more of the rings may contain one or more double bonds, but none of them has a fully conjugated z-electron system. According to the number of formed rings, the fused cycloalkyl may be bicyclic, tricyclic, tetracyclic or polycyclic, including but not limited to:

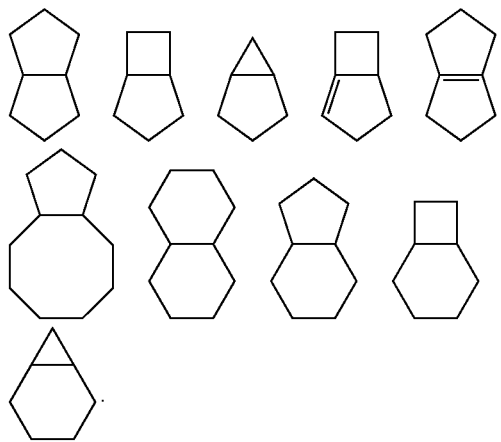

"Bridged cycloalkyl" refers to an all-carbon polycyclic group in which any two rings share two carbon atoms that are not directly connected to each other, wherein these rings may contain one or more double bonds, but none of them has a fully conjugated π-electron system. According to the number of formed rings, the bridged cycloalkyl may be bicyclic, tricyclic, tetracyclic or polycyclic, including but not limited to:

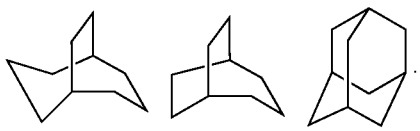

The cycloalkyl ring can be fused to an aryl, heteroaryl or heterocycloalkyl ring, wherein the ring attached to the parent structure is cycloalkyl, which includes but is not limited to indanyl, tetrahydronaphthyl, benzocycloheptyl, etc.

Cycloalkyl may be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, $C_{0-8}$—S(O)$_r$R$_{11}$, —C$_{0-8}$—O—R$_{12}$, —C$_{0-8}$—C(O)OR$_{12}$, —C$_{0-8}$—C(O)R$_{13}$, —C$_{0-8}$—O—C(O)R$_{13}$, —C$_{0-8}$—NR$_{14}$R$_{15}$, —C$_{0-8}$—C(O)NR$_{14}$R$_{15}$ and —C$_{0-8}$—N(R$_{14}$)—C(O)R$_{13}$.

"Heterocyclyl" refers to a monocyclic or polycyclic hydrocarbon substituent that is saturated or partially unsaturated, wherein one or more of the ring atoms are heteroatoms selected from nitrogen, oxygen or S(O)$_r$(wherein r is an integer of 0, 1 or 2), excluding ring portions of —O—O—, —O—S— or —S—S—, and the remaining ring atoms are carbon atoms. For example, "5-10 membered heterocyclyl" refers to a cyclic group containing 5 to 10 ring atoms, and "3-10 membered heterocyclyl" means a cyclic group containing 3 to 10 ring atoms.

Monocyclic heterocyclyl includes but is not limited to pyrrolidinyl, piperadinyl, piperazinyl, morpholinyl, thiomorpholinyl, homopiperazinyl, etc.

Polycyclic heterocyclyl includes spiroheterocyclyl, fused heterocyclyl, and bridged heterocyclyl. "Spiroheterocyclyl" refers to a polycyclic heterocyclyl group in which an atom (called spiro-atom) is shared among monocyclic rings, wherein one or more ring atoms are heteroatoms selected from nitrogen, oxygen or S(O)$_r$(wherein r is an integer of 0, 1 or 2), and the remaining ring atoms are carbon atoms. These rings may contain one or more double bonds, but none of them has a fully conjugated π-electron system. According to the number of spiro-atoms shared among the rings, spiroheterocyclyl may be monospiroheterocyclyl, bispiroheterocyclyl or polyspiroheterocyclyl. Spiroheterocyclyl includes but is not limited to:

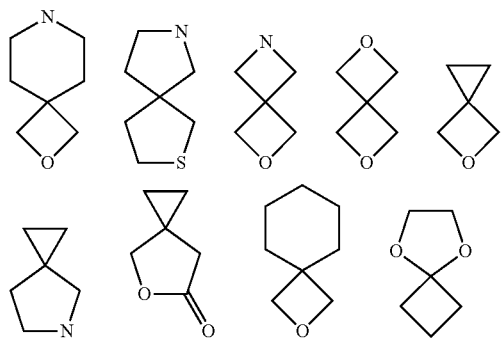

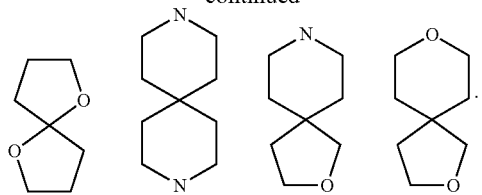

"Fused heterocyclyl" refers to a polycyclic heterocyclyl in which each ring shares a pair of adjacent atoms with the other rings in the system, wherein one or more of the rings may contain one or more double bonds, but none of them has a fully conjugated a-electron system, wherein one or more of the ring atoms are heteroatoms selected from nitrogen, oxygen or S(O)$_r$ (wherein r is an integer of 0, 1 or 2), and the remaining ring atoms are carbon atoms. According to the number of formed rings, the fused heterocyclyl may be bicyclic, tricyclic, tetracyclic or polycyclic, including but not limited to:

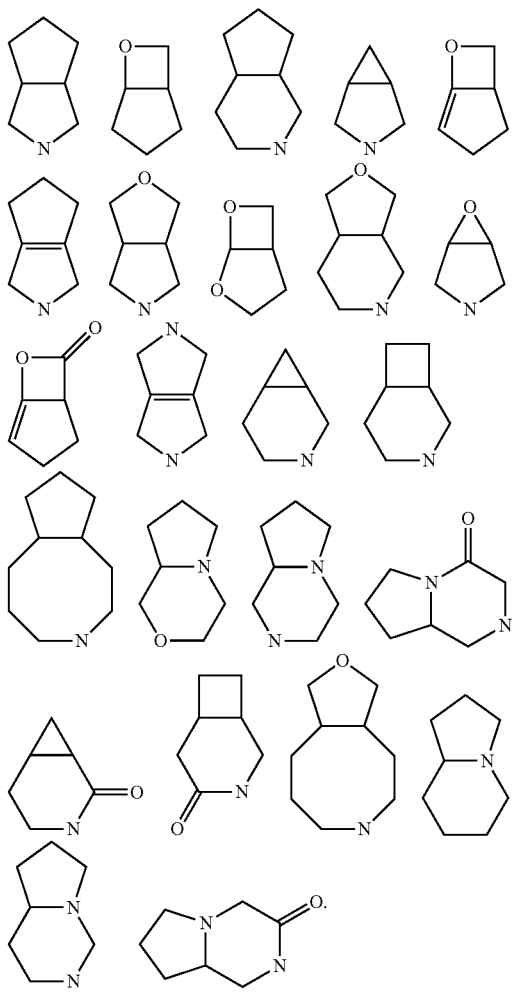

"Bridged heterocyclyl" refers to a polycyclic heterocyclyl in which any two rings share two carbon atoms that are not directly attached to each other, wherein these rings may contain one or more double bonds, but none of them has a fully conjugated it-electron system, wherein one or more of the ring atoms are heteroatoms selected from nitrogen, oxygen or $S(O)_r$(wherein r is an integer of 0, 1 or 2), and the remaining ring atoms are carbon atoms. According to the number of formed rings, the bridged heterocyclyl may be bicyclic, tricyclic, tetracyclic or polycyclic including but not limited to:

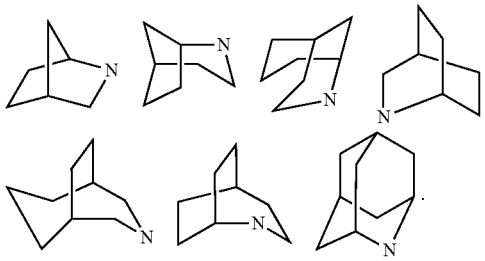

The heterocyclyl ring may be fused to an aryl, heteroaryl or cycloalkyl ring, wherein the ring attached to the parent structure is heterocyclyl, including but not limited to:

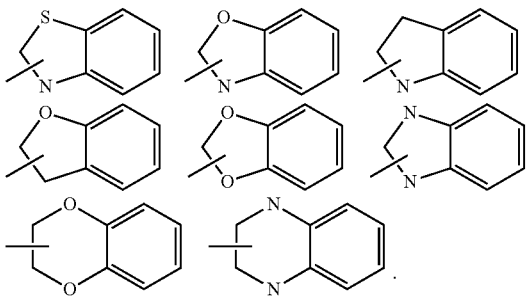

Heterocyclyl may be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—$S(O)_rR_{11}$, —$C_{0-8}$—O—$R_{12}$, —$C_{0-8}$—C(O)$OR_{12}$, —$C_{0-8}$—C(O)$R_{13}$, —$C_{0-8}$—O—C(O)$R_{13}$, —$C_{0-8}$—$NR_{14}R_{15}$, —$C_{0-8}$—C(O)$NR_{14}R_{15}$ and —$C_{0-8}$—N($R_{14}$)—C(O)$R_{13}$.

"Aryl" means an all-carbon monocyclic or fused-polycyclic (i.e., rings that share a pair of adjacent carbon atoms) group and a polycyclic group having a conjugated R-electron system (i.e., rings with adjacent pairs of carbon atoms), for example, "$C_{5-10}$ aryl" means an all-carbon aryl containing 5 to 10 carbon atoms, and "5-10 membered aryl" means an all-carbon aryl containing 5 to 10 carbon atoms, including but not limited to phenyl and naphthyl. The aryl ring can be fused to a heteroaryl, heterocyclyl or cycloalkyl ring, wherein the ring attached to the parent structure is the aryl ring, including but not limited to:

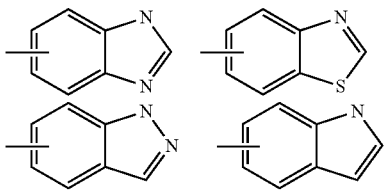

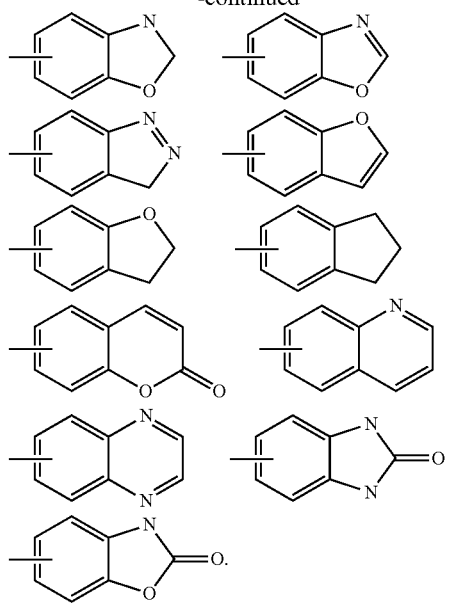

Aryl can be substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—$S(O)_rR_{11}$, —$C_{0-8}$—O—$R_{12}$, —$C_{0-8}$—C(O)$OR_{12}$, —$C_{0-8}$—C(O)$R_{13}$, —$C_{0-8}$—O—C(O)$R_{13}$, —$C_{0-8}$—$NR_{14}R_{15}$, —$C_{0-8}$—C(O)$NR_{14}R_{15}$ and —$C_{0-8}$—N($R_{14}$)—C(O)$R_{13}$.

"Heteroaryl" refers to a heteroaromatic system containing 1 to 4 heteroatoms, and the heteroatoms include heteroatoms selected from nitrogen, oxygen or $S(O)_r$(wherein r is an integer of 0, 1 or 2), for example, 5-8 membered heteroaryl means a heteroaromatic system containing 5 to 8 ring atoms, and 5-10 membered heteroaryl means a heteroaromatic system containing 5 to 10 ring atoms, including but not limited to furyl, thiophenyl, pyridyl, pyrrolyl, N-alkylpyrrolyl, pyrimidinyl, pyrazinyl, imidazolyl, tetrazolyl, etc. The heteroaryl ring can be fused to an aryl, heterocyclyl or cycloalkyl ring, wherein the ring attached to the parent structure is the heteroaryl ring, including but not limited to:

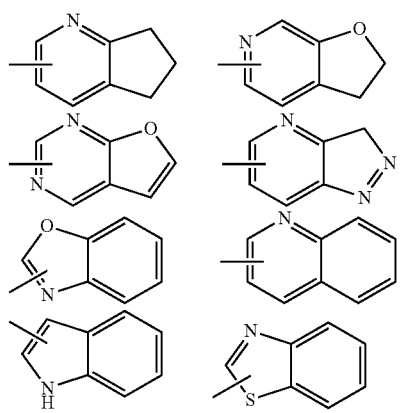

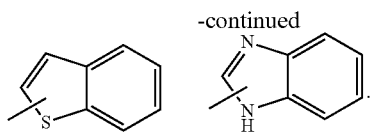

Heteroaryl can be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$.

"Alkenyl" refers to an alkyl defined as above consisting of at least two carbon atoms and at least one carbon-carbon double bond, for example, $C_{2-8}$ alkenyl means a linear or branched alkenyl containing 2 to 8 carbon atoms. The alkenyl includes but is not limited to vinyl, 1-propenyl, 2-propenyl, 1-, 2- or 3-butenyl, etc.

Alkenyl can be substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{2-8}$ haloalkyl, $C_{3-10}$ cycloalkyl, 3-10 membered heterocyclyl, $C_{5-10}$ aryl, 5-10 membered heteroxyl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$.

"Alkynyl" refers to an alkyl defined as above consisting of at least two carbon atoms and at least one carbon-carbon triple bond, for example, $C_{2-8}$ alkynyl means a linear or branched alkynyl containing 2 to 8 carbon atoms. The alkynyl includes but is not limited to ethynyl, 1-propynyl, 2-propynyl, 1-, 2- or 3-butynyl, etc.

Alkynyl may be substituted or unsubstituted, and when it is substituted, the substituent s preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$.

"Alkoxy" refers to —O-(alkyl), wherein the alkyl is defined as above, for example, "$C_{1-8}$ alkoxy" means an alkoxy containing 1 to 8 carbons atoms, including but not limited to methoxy ethoxy, propoxy, butoxy, etc.

Alkoxy may be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$.

"Cycloalkyloxy" refers to —O-(unsubstituted cycloalkyl) wherein the cycloalkyl is defined as above, for example, "$C_{3-10}$ cycloalkyloxy" means a cycloalkyloxy containing 3 to 10 carbon atoms, including but not limited to cyclopropyloxy, cyclobutyloxy, cyclopentyloxy, cyclohexyloxy, etc.

Cycloalkyloxy may be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$.

"3-10 membered heterocyclyloxy" refers to —O-(unsubstituted 3-10 membered heterocyclyl), wherein 3-10 membered heterocyclyl is defined as above. The 3-10 membered heterocyclyloxy may be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$.

"$C_{5-10}$ aryloxy" refers to —O-(unsubstituted $C_{5-10}$ aryl), wherein $C_{5-10}$ aryl is defined as above. The $C_{5-10}$ aryloxy may be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$.

"5-10 membered heteroaryloxy" refers to —O-(unsubstituted 5-10 membered heteroaryl), wherein the 5-10 membered heteroaryl is defined as above. The 5-10 membered heteroaryloxy may be optionally substituted or unsubstituted, and when it is substituted, the substituent is preferably one or more of the groups independently selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$.

"$C_{1-8}$ alkanoyl" refers to a monovalent atomic group which is obtained after a hydroxy is removed from the $C_{1-8}$ alkyl acid, and is also generally referred to as "$C_{0-7}$—C(O)—", for example, "$C_1$—C(O)—" refers to an acetyl; "$C_2$—C(O)—" refers to a propionyl; and "$C_3$—C(O)—" refers to a butyryl or isobutyryl.

"—$C_{0-8}$—S(O) (=NR$_{10}$)R$_{11}$" means that the sulfur atom in —S(O) (=NR$_{10}$)R$_{11}$ is attached to $C_{0-8}$ alkyl, wherein $C_0$ alkyl refers to a bond, and $C_{1-8}$ alkyl is defined as above.

"—$C_{0-8}$—B(OR$_{12}$)$_2$" means that the boron atom in —B(OR$_{12}$)$_2$ is attached to $C_{0-8}$ alkyl, wherein $C_0$ alkyl refers to a bond, and $C_{1-8}$ alkyl is defined as above.

"—$C_{0-8}$—P(O)(R$_{13}$)$_2$" means that the phosphorus atom in —P(O)(R$_{13}$)$_2$ is attached to $C_{0-8}$ alkyl, wherein $C_0$ alkyl refers to a bond, and $C_{1-8}$ alkyl is defined as above.

"—C$_{0-8}$—S(O)$_r$R$_{11}$" means that the sulfur atom in —S(O)$_r$R$_{11}$ is attached to C$_{0-8}$ alkyl, wherein C$_0$ alkyl refers to a bond, and C$_{1-8}$ alkyl is defined as above.

"—C$_{0-8}$—O—R$_{12}$" means that the oxygen atom in —O—R$_{12}$ is attached to C$_{0-8}$ alkyl, wherein C$_0$ alkyl refers to a bond, and C$_{1-8}$ alkyl is defined as above.

"—C$_{0-8}$—C(O)OR$_{12}$" means that the carbonyl in —C(O)OR$_{12}$ is attached to C$_{0-8}$ alkyl, wherein C$_0$ alkyl refers to a bond, and C$_{1-8}$ alkyl is defined as above.

"—C$_{0-8}$—C(O)R$_{13}$" means that the carbonyl in —C(O)R$_{13}$ is attached to C$_{0-8}$ alkyl, wherein C$_0$ alkyl refers to a bond, and C$_{1-8}$ alkyl is defined as above.

"—C$_{0-8}$—O—C(O)R$_{13}$" means that the oxygen atom in —O—C(O)R$_{13}$ is attached to C$_{0-8}$ alkyl, wherein C$_0$ alkyl refers to a bond, and C$_{1-8}$ alkyl is defined as above.

"—C$_{0-8}$—NR$_{14}$R$_{15}$" means that the nitrogen atom in —NR$_{14}$R$_{15}$ is attached to C$_{0-8}$ alkyl, wherein C$_0$ alkyl refers to a bond, and C$_{1-8}$ alkyl is defined as above.

"—C$_{0-8}$—C(O)NR$_{13}$R$_{14}$" means that the carbonyl in -C(O)NR$_{13}$R$_{14}$ is attached to C$_{0-8}$ alkyl, wherein C$_0$ alkyl refers to a bond, and C$_{1-8}$ alkyl is defined as above.

"—C$_{0-8}$—N(R$_{14}$)–C(O)R$_{13}$" means that the nitrogen atom in —N(R$_{14}$)—C(O)R$_{13}$ is attached to C$_{0-8}$ alkyl, wherein C$_0$ alkyl refers to a bond, and C$_{1-8}$ alkyl is defined as above.

"C$_{1-8}$ haloalkyl" refers to an alkyl having 1 to 8 carbon atoms in which hydrogens on the alkyl are optionally substituted by a fluorine, chlorine, bromine or iodine atom, including but not limited to difluoromethyl, dichloromethyl, dibromomethyl, trifluoromethyl, trichloromethyl, tribromomethyl, etc.

"C$_{1-8}$ haloalkoxy" refers to an alkoxy having 1 to 8 carbon atoms in which hydrogens on the alkyl are optionally substituted by a fluorine, chlorine, bromine or iodine atom, including but not limited to difluoromethoxy, dichloromethoxy, dibromomethoxy, trifluoromethoxy, trichloromethoxy, tribromomethoxy, etc.

"Halogen" refers to fluorine, chlorine, bromine or iodine.

"MeOH" refers to methanol. "DCM" refers to dichloromethane. "EA" refers to ethyl acetate, "PE" refers to petroleum ether. "BINAP" refers to (±)-2,2'-bis-(diphenylphosphino)-1,1'-dinaphthalene. "XPhos-Pd-G3" refers to methanesulfonato(2-dicyclohexylphosphino-2',4',6'-triisopropyl-1,1'-biphenyl)(2'-amino-1,1'-biphenyl-2-yl)palladium(II). "Pd(dppf)Cl$_2$" refers to [1,1'-bis(diphenylphosphino)ferrocene]palladium dichloride.

The term "optional" or "optionally" means that the event or circumstance subsequently described may, but not necessarily, occur, and that the description includes instances where the event or circumstance occurs or does not occur. For example, "heterocyclyl group optionally substituted by alkyl" means that alkyl may be, but not necessarily, present, and that the description includes instances where the heterocyclyl group is or is not substituted by alkyl.

The term "substituted" means that one or more hydrogen atoms in a group are each independently substituted by a corresponding number of substituents. It goes without saying that a substituent is only in its possible chemical position, and those skilled in the art will be able to determine (by experiments or theories) possible or impossible substitution without undue efforts. For example, it may be unstable when an amino or hydroxyl having a free hydrogen is bound to a carbon atom having an unsaturated bond (such as olefin).

"Pharmaceutical composition" refers to a mixture containing one or more of the compounds described herein or a physiologically/pharmaceutically acceptable salt or prodrug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The present invention is further explained in detail below with reference to embodiments, which are not intended to limit the present invention, and the present invention is not merely limited to the contents of the embodiments.

The compound structure of the present invention is determined by nuclear magnetic resonance (NMR) and/or liquid chromatography-mass spectrometry (LC-MS). The NMR chemical shift (d) is given in parts per million (ppm). The NMR determination is conducted by using a Barker AVANCE-400 nuclear magnetic resonance apparatus, with hexadeuterodimethyl sulfoxide (DMSO-d$_6$), tetradeuteromethanol (CD$_3$OD) and deuterated chloroform (CDCl$_3$) as determination solvents, and tetramethylsilane (TMS) as internal standard.

The LC-MS determination is conducted by using an Agilent 6120 mass spectrometer. The HPLC determination is conducted by using an Agilent 1200 DAD high pressure liquid chromatograph (Sunfire C18 150×4.6 mm chromatographic column) and a Waters 2695-2996 high pressure liquid chromatograph (Gimini C18 150×4.6 mm chromatographic column).

Yantai Yellow Sea HSGF254 or Qingdao GF254 silica gel plate is adopted as a thin layer chromatography (TLC) silica gel plate. The specification adopted by the TLC is 0.15-0.20 mm, and the specification adopted by the thin layer chromatography for the separation and purification of products is 0,4-0.5 mm. The Yantai Yellow Sea silica gel of 200-300 mesh is generally utilized as a carrier in column chromatography.

Starting materials in the embodiments of the present invention are known and commercially available, or may be synthesized by using or according to methods known in the art.

Unless otherwise stated, all reactions of the present invention are carried out under a dry nitrogen or argon atmosphere with continuous magnetic stirring, wherein the solvent is a dry solvent, and the reaction temperature is in degree centigrade (° C.).

Preparation of Intermediates

Preparation of Intermediate A1: 1-(2-methoxyethyl)-4-(4,4,5,5-tetramethyl-1,3,2-dioxaborolan-2-yl)-1H-pyrazole

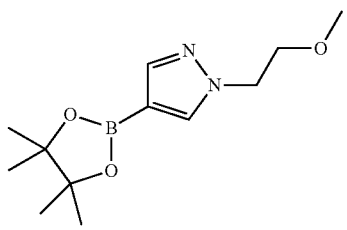

4-(4,4,5,5-tetramethyl-1,3,2-dioxaborolan-2-yl)-1H-pyrazole (582 mg, 3.0 mmol) was dissolved in N,N-dimethylformamide (5 mL), and then 1-bromo-2-methoxyethane (798 mg, 6.0 mmol), cesium carbonate (2.9 g, 9.0 mmol.), and sodium iodide (224 mg, 1.5 mmol) were added. The reaction solution was stirred at 70° C. for 3 hrs, then poured into water (50 mL) and extracted with ethyl acetate (40 mL*2). Organic phases were combined and washed with brine (40 mL), dried over sodium sulfate, and then filtered. The filtrate was concentrated to obtain a crude product of 1-(2-methoxyethyl)-4-(4,4,5,5-tetramethyl-1,3,2-dioxaborolan-2-yl)-1H-pyrazole (240 mg, yield 32%). MS m/z (ESI): 253 [M+H]$^+$.

Preparation of Intermediate A2: 4-(2-(4-(4,4,5,5-tetramethyl-1,3,2-dioxaborolan-2-yl)-1H-pyrazol-1-yl)ethyl)morpholine

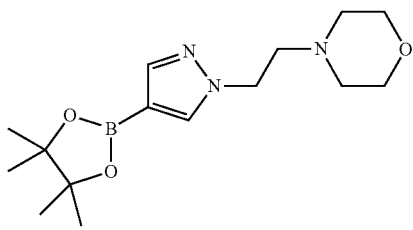 [SMILES: CC1(C)OB(c2cnn(CCN3CCOCC3)c2)OC1(C)C]

The intermediate A2 was prepared according to the synthesis method of the intermediate A1. MS m/z (ESI): 308 [M+H]$^+$.

Preparation of Intermediate A3: 1-(2-(2-((tert-butyldimethylsilyl)oxy)ethyl)-4-(4,4,5,5-tetramethyl-1,3,2-dioxaborolan-2-yl)1H-pyrazole

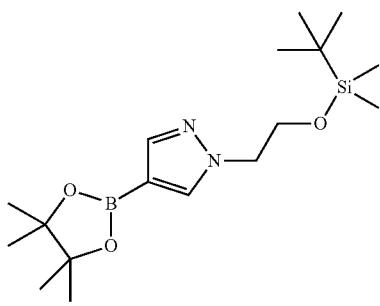

4-(4,4,5,5-tetramethyl-1,3,2-dioxaborolan-2-yl)-1H-pyrazole (8.5 g, 43.8 mmol) was dissolved in acetonitrile (100 mL), then (2-bromoethoxy)(tert-butyl)dimethylsilane (15.7 g, 65.7 mmol) and potassium carbonate (18 g, 131.4 mmol) were added. The reaction solution was stirred at 90° C. for 16 hrs. Then the solution was filtered and concentrated to obtain a crude product of 1-(2-((tert-butyldimethylsilyl)oxy)ethyl)-4-(4,4,5,5-tetramethyl-1,3,2-dioxaborolan-2-yl)-1H-pyrazole (2 g, yield 100%). MS m/z (ESI): 353 [M+H]$^+$.

Preparation of Intermediate A4: 1-(methyl-d$_3$)-4-(4,4,5,5-tetramethyl-1,3,2-dioxaborolan-2-yl)1H-pyrazole

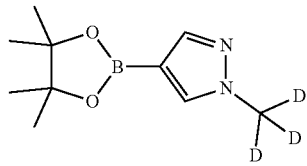 [SMILES: [2H]C([2H])([2H])n1cc(B2OC(C)(C)C(C)(C)O2)cn1]

4-(4,4,5,5-tetramethyl-1,3,2-dioxaborolan-2-yl)-1H-pyrazole (0.501 g, 2.58 mmol) and potassium carbonate (1.172 g, 8.48 mmol) were added to a dry flask. Acetonitrile (20 ml) was added as a reaction solvent, and then deuterated iodomethane (3.5 mL, 5.16 mmol) was added. The reaction solution was stirred at 90° C. for 3.5 hrs with the container being sealed. After the reaction completed, the solid was filtered off, and the filtrate was concentrated to obtain 1-(methyl-d$_3$)-4-(4,4,5,5-tetramethyl-1,3,2-dioxaborolan-2-yl)-1H-pyrazole (0.532 g, yield 93%). MS m/z (ESI): 212 [M-H]$^+$.

Preparation of Intermediate A5: (S)-1-(tetrahydrofuran-3-yl)-4-(4,4,5,5-tetramethyl-1,3,2-dioxaborolan-2-yl)-1H-pyrazole

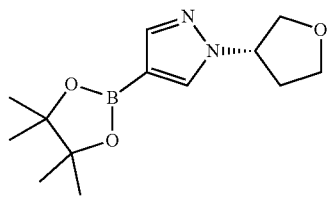 [SMILES: CC1(C)OB(c2cnn([C@H]3CCOC3)c2)OC1(C)C]

Diisopropyl azodiformate (1.7 mL, 8.58 mmol) was added dropwise to the solution of 4-(4,4,5,5-tetramethyl-1,3,2-dioxaborolan-2-yl)-1H-pyrazole (1.110 g, 5.72 mmol), (R)-tetrahydrofuran-3-ol (0.515 g, 5.84 mmol) and triphenylphosphine (2.243 g, 8.55) in an anhydrous tetrahydrofuran (7 mL) under nitrogen protection and an ice bath. The reaction solution was stirred under an ice bath for 30 min, and then at room temperature for 21 hrs. After ethyl acetate (10 mL) was added for diluting, the solution was washed with a saturated brine (15 mL*2). The organic layers were combined, dried and concentrated under reduced pressure, and then separated by the column chromatography to obtain (S)-1-(tetrahydrofuran-3-yl)-4-(4,4,5,5-tetramethyl-1,3,2-dioxaborolan-2-yl)-1H-pyrazole 0.324 g, 21.5%). MS m/z (ESI): 265 [M+H]$^+$.

Preparation of Intermediate A6: 2-methyl-1-(4-(4,4,5,5-tetramethyl-1,3,2-dioxaborolan-2-yl)-1H-pyrazol-1-yl)propan-2-ol

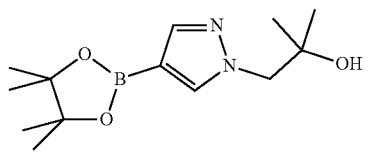 [SMILES: CC(C)(O)Cn1cc(B2OC(C)(C)C(C)(C)O2)cn1]

4-(4,4,5,5-tetramethyl-1,3,2-dioxaborolan-2-yl)-1H-pyrazole (500 mg, 2.58 mmol), 2,2-dimethyloxirane (0.57 mL, 6.44 mmol), cesium carbonate (1.25 g, 3.84 mmol), and acetonitrile (10 mL) were added to a microwave tube. The reaction mixture was reacted in a microwave reactor at 130° C. for 1 hr. After the reaction completed, dichloromethane was added, and then the mixture was filtered. The filtrate was concentrated to obtain 2-methyl-1-(4-(4,4,5,5-tetramethyl-1,3,2-dioxaborolan-2-yl)-1H-pyrazol-1-yl)propan-2-ol (480 mg, yield 35%). MS m/z (ESI): 267 [M+H]$^+$.

Preparation of Intermediate A7: 1-(1-methylpyrrolidin-3-yl)-4-(4,4,5,5-tetramethyl-1,3,2-dioxaborolan-2-yl)-1H-pyrazole

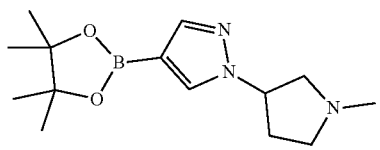

Step 1: preparation of 1-methylpyrrolidin-3-yl methanesulfonate

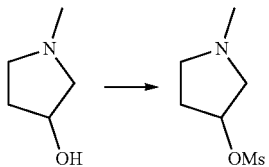

Methanesulfonyl chloride (1.68 mL, 21.7 mmol) and triethylamine (3.29 mL, 23.7 mmol) were respectively added to the solution of 1-methylpyrrolidine-3-ol (2.00 g, 19.8 mmol) in dichloromethane (30 mL) under an ice bath, and then the mixture was reacted at room temperature for 1.5 hrs after the temperature was stable. After dichloromethane (5 mL) was added to dilute the reaction solution, the mixture solution was washed twice with saturated sodium bicarbonate (5 mL), and then washed twice with water. The organic phase was dried and concentrated under reduced pressure to obtain a yellow oily liquid crude product which was directly used in the next step reaction.

Step 2: preparation of 1-(1-methylpyrrolidin-3-yl)-4-(4,4,5,5-tetramethyl-1,3,2-dioxaborolan-2-yl)-1H-pyrazole

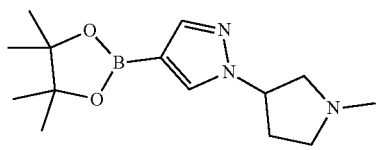

Sodium hydride (0.62 g, 15.5 mmol) was added to the solution of 4-(4,4,5,5-tetramethyl-1,3,2-dioxaborolan-2-yl)-1H-pyrazole (2.427 g, 12.5 mmol) in N,N-dimethylformamide (18 mL) under an ice bath, the mixture solution was stirred for 10 min. Then 1-methylpyrrolidin-3-yl methanesulfonate (2.220 g, 12.4 mmol) was added to the above reaction solution. The reaction solution was stirred at 100° C. for 18 hrs. After the reaction is completed, the solution was cooled to room temperature, diluted with ethyl acetate (5 mL), washed with a saturated ammonium chloride solution (5 mL), and then washed with water. The organic layer was dried and concentrated, and then separated by column chromatography (eluent: dichloromethane/methanol) to obtain 1-(1-methylpyrrolidin-3-yl)-4-(4,4,5,5-tetramethyl-1,3,2-dioxaborolan-2-yl)-1H-pyrazole (0.476 g, yield 13.9%), which was directly used in the next step reaction.

Preparation of Intermediate A8: 1-(oxetan-3-yl)-4-(4,4,5,5-tetramethyl-1,3,2-dioxaborolan-2-yl)-1H-pyrazole

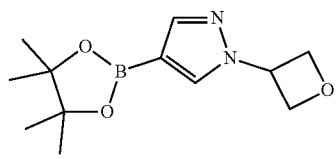 [SMILES: CC1(C)OB(c2cnn(C3COC3)c2)OC1(C)C]

Step 1: Preparation of oxetan-3-yl methanesulfonate

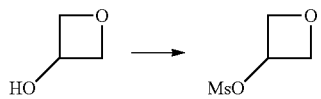

Methanesulfonyl chloride (2.30 mL, 29.7 mmol) and triethylamine (4.5 mL, 32.4 mmol) were respectively added to the solution of oxetane-3-ol (2.01 g, 27.0 mmol) in dichloromethane (20 mL) under an ice bath, then the mixture solution was stirred at room temperature for 5.5 hrs after the temperature was stable. After dichloromethane (10 mL) was added to dilute the reaction solution, the solution was washed twice with saturated sodium bicarbonate (10 mL), and then washed twice with a saturated brine (10 mL). The organic phase was dried and concentrated under reduced pressure to obtain a crude product of oxetan-3-yl methanesulfonate (2.80 g, yield 68%), which was directly used in the next step reaction.

Step 2: Preparation of 1-(oxetan-3-yl)-4-4,4,5,5-tetramethyl-1,3,2-dioxaborolan-2-yl)-1H-pyrazole

60% sodium hydride (0.873 g, 36.4 mmol) was added to the solution of 4-(4,4,5,5-tetramethyl-1,3,2-dioxaborolan-2-yl)-1H-pyrazole (3.482 g, 17.9 mmol) in N,N-dimethylformamide (30 mL) under an ice bath, then the mixture solution was stirred for 10 min. Then oxetan-3-yl methanesulfonate (2.80 g, 18.4 mmol) was added to the above reaction solution, then the reaction solution was stirred at 100° C. for 21 hrs. After the reaction was completed, the mixture solution was cooled to room temperature, diluted with ethyl acetate (15 mL), washed with a saturated ammonium chloride solution (15 mL), and then washed with a saturated brine (15 mL). The organic layer was dried and concentrated, and then separated by column chromatography [eluent: dichloromethane/methanol] to obtain 1-(oxetan-3-yl)-4-(4,4,5,5-tetramethyl)-1,3,2-dioxaborolan-2-yl)-1H-pyrazole (0.587 g, yield 13%). MS m/z (ESI): 251 [M+H]⁺.

Preparation of Intermediate B1:
5-bromo-6-ethylpyridine-2-amine

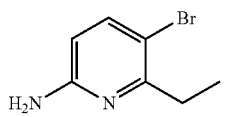

6-ethylpyridin-2-amine (4.5 g, 36.8 mmol) was dissolved in dichloromethane (20 mL), and then liquid bromine (5.25 g, 29.5 mmol) was added. The reaction solution was stirred for 30 min wider an ice bath. Dichloromethane and water were added, and then the mixture solution was separated. The organic phase was successively washed with water and saturated brine, then dried over anhydrous sodium sulfate, filtered, concentrated, and separated by column chromatography to obtain 5-bromo-6-ethylpyridin-2-amine (5.9 g, yield 74%). MS m/z (ESI): 201 [M+1]⁺.

Preparation of Intermediate C1:
3-bromo-2-methyl-6-nitropyridine

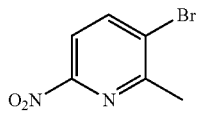

In a three-necked flask, 30% hydrogen peroxide (25 mL) was added dropwise to concentrated sulfuric acid (38 mL), and the reaction temperature was controlled not to exceed 10° C. Then the solution of 5-bromo-6-methylpyridin-2-amine (7.0 g, 37.4 mmol) in concentrated sulfuric acid (38 mL) was added dropwise to the above reaction solution, and the reaction temperature was controlled not to exceed 20° C. The reaction solution was stirred for 1 hr under an ice bath, and then stirred at room temperature for 2 hrs. The reaction solution was poured into 1.5 L of ice water, then filtered. The filter cake was washed with 1.5 L of water, and then dissolved in dichloromethane (200 mL). The organic phase was washed with water and a saturated brine, dried over anhydrous sodium sulfate and filtered, and the filtrate was concentrated to obtain 3-bromo-2-methyl-6-nitropyridine (3.8 g, yield 45%).

Preparation of Intermediate C2:
3-bromo-2-ethyl-6-nitropyridine

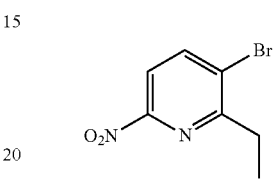

The intermediate C2 was prepared according to the synthesis method of the intermediate C1. MS m/z (ESI): 201 [M−30]⁺.

Preparation of Intermediate D1: 3-((2-chloropyridin-4-yl)oxy)-2-methyl-6-nitropyridine

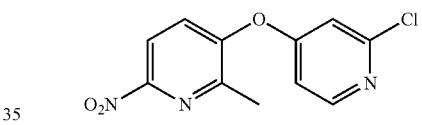

3-bromo-2-methyl-6-nitropyridine (3.8 g, 17.5 mmol) was dissolved in N,N-dimethylformamide (80 mL), then 2-chloropyridin-4-ol (4.5 g, 35 mmol) and potassium carbonate (7.2 g, 52.3 mmol) were added, the reaction solution was stirred overnight at 100° C. Ethyl acetate and water were added, and then the mixture solution was separated. The organic phase was successively washed with water and a saturated brine, then dried over anhydrous sodium sulfate, filtered, concentrated, and separated by column chromatography (eluent: petroleum ether/ethyl acetate (15:1)~(2:1)) to obtain 3-((2-chloropyridin-4-yl)oxy)-2-methyl-6-nitropyridine (1.76 g, yield 37.8%). MS m/z (ESI): 235 [M−30]⁺.

Intermediates D2 and D3 were Prepared According to the Synthesis Method of the intermediate D1.

| Intermediate No. | Structural formula | English name | MS m/z (ESI): [M − 30]⁺ |
|---|---|---|---|
| D2 | | 2-chloro-4-((6-nitropyridin-3-yl)oxy)pyridine | 221 |
| D3 | | 3-((2-chloropyridin-4-yl)oxy)-2-ethyl-6-nitropyridine | 250 |

Preparation of Intermediate E1: 2-methyl-3-((2-(1-methyl-1H-pyrazol)pyridin-4-yl) oxy)-6-nitropyridine

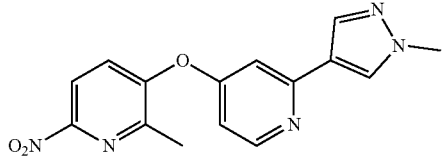 [SMILES: Cc1nc([N+](=O)[O-])ccc1Oc1ccnc(-c2cnn(C)c2)c1]

3-((2-chloropyridin-4-yl)oxy)-2-methyl-6-nitropyridine (300 mg, 1.13 mmol) was dissolved in 1,4-dioxane/water (20 mL/10 mL), and 1-methyl-4-(4,4,5,5-tetramethyl-1,3,2-dioxaborolan-2-yl)-1H-pyrazole (353 mg, 1.69 mmol), potassium carbonate (467 mg, 3.39 mmol), and palladium [1,1-dikis(diphenylphosphorus)ferrocene]dichloride (165 mg, 0.226 mmol) were added. The nitrogen was charged to replace three times by evacuation, then the reaction solution was stirred at 95° C. for 1 hr. Ethyl acetate and water were added, and then the mixture solution was separated. The organic phase was successively washed with water and a saturated brine, then dried over anhydrous sodium sulfate, filtered, concentrated, and separated by column chromatography (eluent: petroleum ether/ethyl acetate 2:1 ~ethyl acetate) to obtain 2-methyl-3-((2-(1-methyl-1H-pyrazol-4-yl)pyridin-4-yl)oxy)-6-nitropyridine (300 mg, yield 85%). MS m/z (ESI): 312 [M+H]$^+$.

The intermediates E2 to E18 were prepared according to the synthesis method of the intermediate E1.

| Intermediate No. | Structural formula | English name | MS m/z (ESI): [M + H]$^+$ |
|---|---|---|---|
| E2 | | 2-(1-methyl-1H-pyrazol-4-yl)-4-((6-nitropyridin-3-yl)oxy)pyridine | 298 |
| E3 | | 2-ethyl-3-((2-(1-methyl-1H-pyrazol-4-yl)pyridin-4-yl)oxy)-6-nitropyridine | 326 |
| E4 | | 2'-methyl-4-((2-methyl-6-nitropyridin-3-yl)oxy)-2,4'-bipyridine | 323 |
| E5 | | 2-methyl-5-(4-((2-methyl-6-nitropyridin-3-yl)oxy)pyridin-2-yl)thiazole | 329 |
| E6 | | 3-((2-(1-ethyl-1H-pyrazol-4-yl)pyridin-4-yl)oxy)-2-methyl-6-nitropyridine | 326 |
| E7 | | 3-((2-(1-(2-methoxyethyl)-1H-pyrazol-4-yl)pyridin-4-yl)oxy)-2-methyl-6-nitropyridine | 356 |

-continued

| Intermediate No. | Structural formula | English name | MS m/z (ESI): [M + H]+ |
|---|---|---|---|
| E8 | 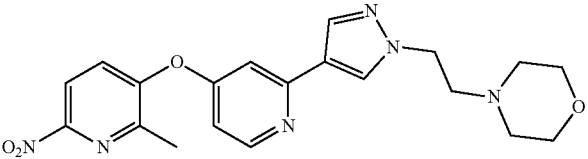 [SMILES: Cc1nc([N+](=O)[O-])ccc1Oc1ccnc(-c2cnn(CCN3CCOCC3)c2)c1] | 4-(2-(4-(4-(2-methyl-6-nitropyridin-3-yl)oxy)pyridin-2-yl)-1H-pyrazol-1-yl)ethyl)morpholine | 411 |
| E9 | 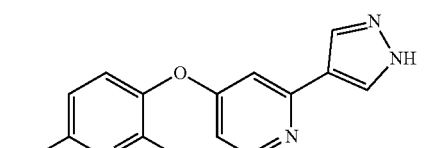 | 3-((2-(1H-pyrazol-4-yl)pyridin-4-yl)oxy)-2-methyl-6-nitropyridine | 298 |
| E10 | 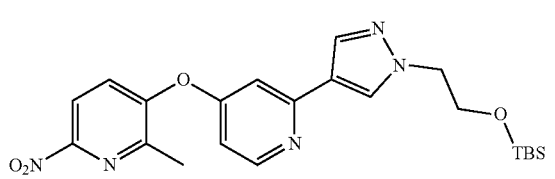 | 3-((2-(1-(2-((tert-butyldimethylsilyl)oxy)ethyl)-1H-pyrazol-4-yl)pyridin-4-yl)oxy)-2-methyl-6-nitropyridine | 456 |
| E11 | 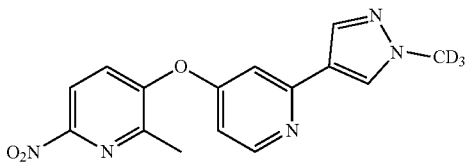 [SMILES: [2H]C([2H])([2H])n1cc(-c2cc(Oc3ccc([N+](=O)[O-])nc3C)ccn2)cn1] | 2-methyl-3-((2-(1-(methyl-$d_3$)-1H-pyrazol-4-yl)pyridin-4-yl)oxy)-6-nitropyridine | 315 |
| E12 | 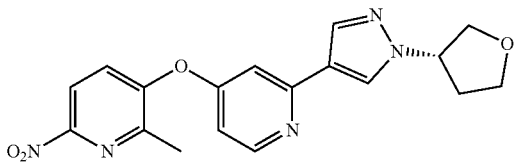 [SMILES: Cc1nc([N+](=O)[O-])ccc1Oc1ccnc(-c2cnn([C@H]3CCOC3)c2)c1] | (S)-2-methyl-6-nitro-3-((2-(1-(tetrahydrofuran-3-yl)-1H-pyrazol-4-yl)pyridin-4-yl)oxy)pyridine | 368 |
| E13 | 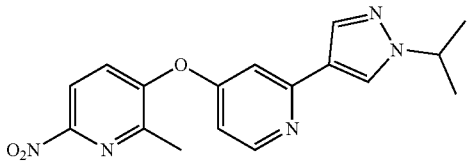 [SMILES: Cc1nc([N+](=O)[O-])ccc1Oc1ccnc(-c2cnn(C(C)C)c2)c1] | 3-((2-(1-isopropyl-1H-pyrazol-4-yl)pyridin-4-yl)oxy)-2-methyl-6-nitropyridine | 340 |
| E14 | 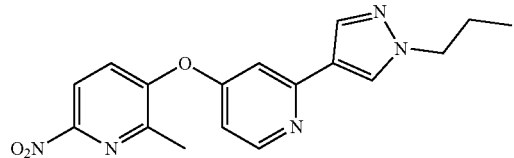 | 2-methyl-6-nitro-3-((2-(1-propyl-1H-pyrazol-4-l)pyridin-4-yl)oxy)pyridine | 340 |
| E15 | 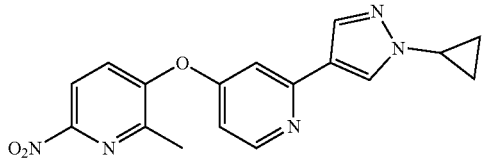 | 3-((2-(1-cyclopropyl-1H-pyrazol-4-yl)pyridin-4-yl)oxy)-2-methyl-6-nitropyridine | 338 |

| Intermediate No. | Structural formula | English name | MS m/z (ESI): [M + H]+ |
|---|---|---|---|
| E16 | | 2-methyl-1-(4-(4-((2-methyl-6-nitropyridin-3-yl)oxy)pyridin-2-yl)-1H-pyrazol-1-yl)propan-2-ol | 370 |
| E17 | | 2-methyl-3-((2-(1-(1-methylpyrrolidine-3-yl)-1H-pyrazol-4-yl)pyridin-4-yl)oxy)-6-nitropyridine | 381 |
| E18 | | 2-methyl-6-nitro-3-((2-(1-(oxetan-3-yl)-1H-pyrazol-4-yl)pyridin-4-yl)oxy)pyridine | 354 |

Preparation of Intermediate E19: 2-methyl-3-((2-(1-methyl-1H-imidazol-4-yl)pyridin-4-yl)oxy)-6-nitropyridine

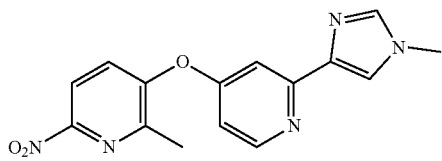 [SMILES: Cc1nc([N+](=O)[O-])ccc1Oc1ccnc(-c2cn(C)cn2)c1]

Step 1: Preparation of 1-methyl-4-(tributylstannyl)-1H-imidazole

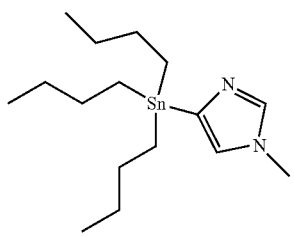 [SMILES: CCC[CH2][Sn]([CH2]CCC)([CH2]CCC)[c]1cn(C)cn1]

4-iodo-1-methyl-1H-imidazole (2.50 mg, 1.2 mmol) was dissolved in anhydrous tetrahydrofuran (4 mL). Magnesium ethylbromide (1.2 mL, 1.2 mmol) was slowly added dropwise at −15° C., and the mixture solution was continuously stirred for 1 hr. Tin tributylchloride (391 mg, 1.2 mmol) was added, and the reaction solution was stirred at −15° C. for 1 hr. Then the saturated ammonium chloride solution (20 mL) was added for quenching. The solution was then extracted three times with ethyl acetate (30 mL*3). The organic phases were combined and washed once with a brine (20 mL), dried over sodium sulfate, filtered, and then concentrated to obtain a crude product of 1-methyl-4-(tributylstannyl)-1H-imidazole (400 mg, yield 90%). MS m/z (ESI): 373 [M+H]+.

Step 2: Preparation of 2-methyl-3-((2-(1-methyl-1H-imidazol-4-yl)pyridin-4-yl)oxy)-6-nitropyridine 1-methyl-4-(tributylstannyl)-1H-imidazole (400 mg, 1.07 mmol) was dissolved in 1,4-dioxane (20 mL), and then 3-((2-chloropyridine-4-yl)oxo)-2-methyl-6-nitropyridine (200 mg, 0.75 mmol) and palladium [1,1'-dikis(diphenylphosphino)ferrocene]dichloride (73 mg, 0.1 mmol) were added. The nitrogen was charged to replace three times by evacuation, and then the reaction solution was stirred at 110° C. for 6 hrs. Then the solution is filtered, concentrated, and separated by column chromatography (eluent: petroleum ether~petroleum ether/ethyl acetate (1:8)) to obtain 2-methyl-3-((2-(1-methyl-1H-imidazol-4-yl)pyridin-4-yl)oxy)-6-nitropyridine (52 mg, yield 22%). MS m/z (ESI): 312 [M+H]+.

Preparation of Intermediate E20: 2-methyl-3-((2-(4-methyl-1H-imidazol-1-yl)pyridin-4-yl)oxy)-6-nitropyridine

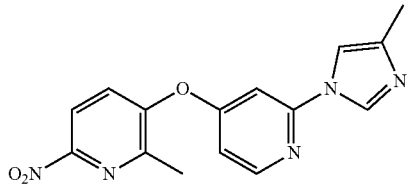 [SMILES: Cc1cn(-c2cc(Oc3ccc([N+](=O)[O-])nc3C)ccn2)cn1]

Step 1: preparation of 4-iodo-2-(4-methyl-1H-imidazol-1-yl)pyridine

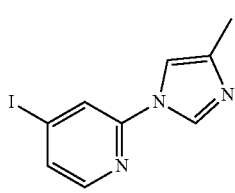

2-fluoro-4-iodopyridine (2.0 g, 8.97 mmol) was dissolved in N,N-dimethylformamide (10 mL). Potassium carbonate (3.7 g, 26.9 mmol) and 4-methyl-1H-imidazole (0.81 g, 9.86 mmol) were added at room temperature. The reaction solution was stirred at 80° C. for 4 hrs, then poured into water (50 mL), and then extracted twice with ethyl acetate (30 mL*2). The organic phases were combined and washed once with a brine (40 mL), dried over sodium sulfate, filtered and concentrated to obtain a crude product of 4-iodo-2-(4-methyl-1H-imidazol-1-yl)pyridine (2.2 g, yield 86%). MS m/z (ESI): 286 [M+H]$^{30}$.

Step 2: Preparation of 4-methoxy-2-(4-methyl-1H-imidazol-1-yl)pyridine

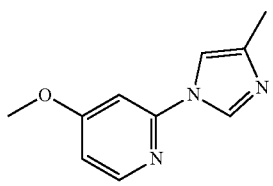

4-iodo-2-(4-methyl-1H-imidazol-1-yl)pyridine (660 mg, 2.3 mmol) was dissolved in the mixture of methanol/N,N-dimethylformamide (10 mL/10 mL). Cuprous bromide (660 mg, 4.6 mmol) and sodium methoxide (6.25 g, 115.78 mmol) were added. The nitrogen was charged to replace three times by evacuation. The reaction solution was stirred at 100° C. for 2 hrs, then poured into water (50 mL), and then extracted twice with ethyl acetate (40 ML*2). The organic phases were combined and washed once with a brine (50 mL), dried over sodium sulfate, filtered and concentrated to obtain a crude product of 4-methoxy-2-(4-methyl-1H-imidazol-1-yl)pyridine (500 mg, yield 100%). MS m/z (ESI): 190 [M+H]$^+$.

Step 3: Preparation of 2-(4-methyl-1H-imidazol-1-yl)pyridin-4-ol

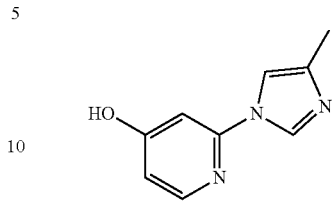

4-methoxy-2-(4-methyl-1H-imidazol-1-yl)pyridine (300 mg, 1.587 mmol) was dissolved in 48% hydrobromic acidaquasolution (20 mL). The reaction solution was stirred at 130° C. for 3 days. The pH of solution was adjusted to 7 with sodium carbonate. After being lyophilized, the solution was ultrasonicated with ethanol for 1 min and then filtered. The filtrate was concentrated to obtain a crude product of 2-(4-methyl-1H-imidazol-1-yl)pyridin-4-ol (250 mg, yield 100%). MS m/z (ESI): 176 [M+H]$^+$.

Step 4: Preparation of 2-methyl-3-((2-(4-methyl-1H-imidazol-1-yl)pyridin-4-yl)oxy)-6-nitropyridine

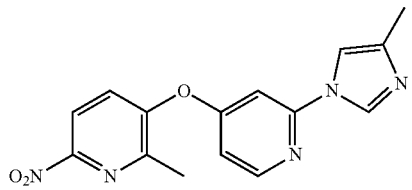 [SMILES: Cc1cn(-c2cc(Oc3ccc([N+](=O)[O-])nc3C)ccn2)cn1]

2-(4-methyl-1H-imidazol-1-yl)pyridin-4-ol (200 mg, 1.14 mmol) was dissolved in N,N-dimethylformamide (5 mL), and then 3-bromo-2-methyl-6-nitropyridine (250 mg, 1.14 mmol), and potassium carbonate (472 g, 3.42 mmol) were added. The reaction solution was stirred at 90° C. for 16 hrs, then poured into water (200 mL), and then extracted twice with ethyl acetate (50 mL*2). The organic phases were combined and washed once with a brine (100 mL), dried over sodium sulfate, then concentrated, and separated by column chromatography (eluent: petroleum ether~petroleum ether/ethyl acetate (4:6)) to obtain 2-methyl-3-((2-(4-methyl-1H-imidazol-1-yl)pyridin-4-yl)oxy)-6-nitropyridine (60 mg, yield 17%). MS m/z (ESI): 311 [M+H]$^+$.

Preparation of Intermediate E21: 2-methyl-3-((2-(1-methyl-1H-pyrazol-4-yl)pyridin-4-yl)methyl)-6-nitropyridine

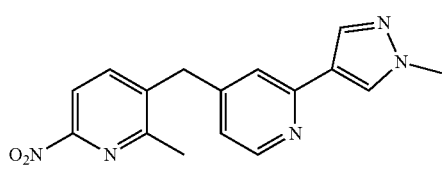 [SMILES: Cc1nc([N+](=O)[O-])ccc1Cc1ccnc(-c2cnn(C)c2)c1]

Step 1: Preparation of 2-(1-methyl-1H-pyrazol-4-yl) isonicotinaldehyde

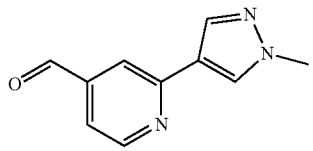

2-chloroisonicotinaldehyde (1.0 g, 7.09 mmol), 1-methyl-1H-pyrazole boronic acid pinacol ester (1.77 g, 8.51 mmol), XPhos-Pd-G3 (100 mg), and potassium carbonate (1.95g, 14.18 mmol) were dissolved in the mixture solution of 1,4-dioxane (20 mL) and water (2 mL). The reaction solution was stirred at 90° C. for 3 hrs under nitrogen protection. When the LCMS showed that the reaction completed, the reaction solution was filtered through celite, and the filtrate is concentrated to dryness. The residue was separated by a rapid silica gel column (0~30% ethyl acetate: petroleum ether) to obtain 2-(1-methyl-1H-pyrazol-4-yl)isonicotinaldehyde (1.0 g, yield 79%). MS m/z (ESI): 188 [M+H]$^+$.

Step 2: Preparation of (2-(1-methyl-1H-pyrazol-4-yl)pyridin-4-yl)methanol

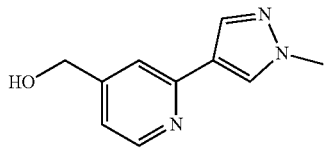

2-(1-methyl-1H-pyrazol-4-yl)isonicotinaldehyde (1.0 g, 5.34 mmol) was dissolved in methanol (20 mL). Sodium borohydride (1.0 g, 26.7 mmol) was added in batches. The reaction solution was stirred at room temperature for 1 hr. When LCMS showed that the reaction completed, the reaction solution was concentrated to dryness. The residue was separated by a rapid silica gel column (0~10% MeOH: DCM) to obtain (2-(1-methyl-1H-pyrazol-4-yl) pyridin-4-yl)methanol (800 mg, yield 80%). MS m/z (ESI): 190 [M+H]$^+$.

Step 3: Preparation of 4-(bromomethyl)-2-(1-methyl-1H-pyrazol-4-yl)pyridine

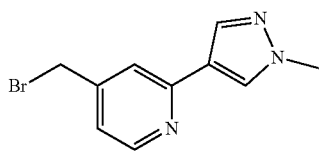

(2-(1-methyl-1H-pyrazol-4-yl)pyridin-4-yl)methanol (500 mg, 2.64 mmol) and carbon tetrabromide (1.31 g, 3.97 mmol) were dissolved in dichloromethane (20 mL). Triphenylphosphine (1.04 g, 3.97 mmol) was added in batches. The reaction solution was stirred at room temperature for 0.5 hr. When the LCMS showed that the reaction completed, the reaction solution was concentrated to dryness. The residue was separated by a rapid silica gel column (0~20% EA:PE) to obtain 4-(bromomethyl)-2-(1-methyl-1H-pyrazol-4-yl) pyridine (300 mg, 45%), which was directly used in the next step reaction.

Step 4: Preparation of 2-methyl-6-nitro-3-(4,4,5,5-tetramethyl-1,3,2-dioxaborolan-2-yl)pyridine

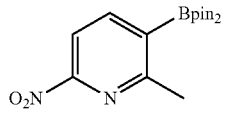

3-bromo-2-methyl-6-nitropyridine (2.2 g, 10.1 mmol), bis(pinacolato)diboron 1.3.0 g, 12.1 mmol), Pd(dppf)Cl$_2$ (200 mg), and potassium acetate (3.0 g, 30.4 mmol) were dissolved in 1,4-dioxane (40 mL). The reaction solution was stirred at 110° C. for 2 hrs under nitrogen protection. When the LCMS showed that the reaction completed, the reaction solution was filtered through celite, and the filtrate is concentrated to dryness. The residue was separated by a rapid silica gel column (0~20% EA:PE) to obtain 2-methyl-6-nitro-3-(4,4,5,5-tetramethyl-1,3,2-dioxaborolan-2-yl)pyridine (1.8 g, yield 67%), which was directly used in the next reaction.

Step 5: Preparation of 2-methyl-3-((2-(1-methyl-1H-pyrazol-4-yl)pyridin-4-yl)methyl)-6-nitropyridine

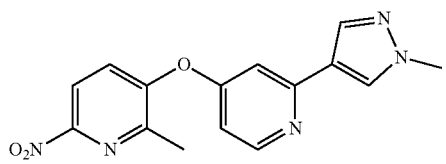 [SMILES: Cc1nc([N+](=O)[O-])ccc1Oc1ccnc(-c2cnn(C)c2)c1]

2-methyl-6-nitro-3-(4,4,5,5-tetramethyl-1,3,2-dioxaborolan-2-yl)pyridine (270 mg, 1.02 mmol), 4-(bromomethyl)-2-(1-methyl-1H-pyrazol-4-yl)pyridine (260 mg, 1.02 mmol), XPhos-Pd-G3 (50 mg), and potassium phosphate (650 mg, 3.06 mmol) were dissolved in the mixture solution of 1,4-dioxane (10 mL) and water (2 mL). The reaction solution was stirred at 90° C. for 3 hrs under nitrogen protection. When the LCMS showed that the reaction completed, the reaction solution was filtered through celite, and the filtrate was concentrated to dryness. The residue was separated by a rapid silica gel column (0~10% MeOH: DCM) to obtain 2-methyl-3-((2-(1-methyl-1H-pyrazol-4-yl) pyridin-4-yl)methyl)-6-nitropyridine (250 mg, yield 79%), MS m/z (ESI): 280 [M–30]$^+$.

Preparation of Intermediate E22: 2-(1-methyl-1H-pyrazol-4-yl)-4-((2-methyl-6-nitropyridin-3-yl)oxy) pyrimidine

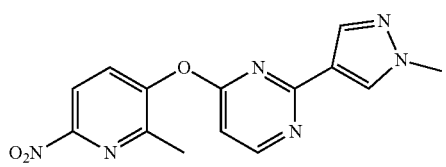 [SMILES: Cc1nc([N+](=O)[O-])ccc1Oc1ccnc(-c2cnn(C)c2)n1]

Step 1: Preparation of 2-methyl-6-nitropyridin-3-ol

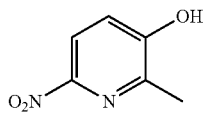

2-methyl-6-nitro-3-(4,4,5,5-tetramethyl-1,3,2-dioxaborolan-2-yl)pyridine (1.4 g, 5.28 mmol) was dissolved in dichloromethane (50 mL). Hydrogen peroxide (30% aqueous solution, 3:0 g. 26.4 mmol) was added to the above solution. The reaction solution was stirred at room temperature for 16 hrs. After the reaction completed, the solution was filtered, and the solvent was removed under reduced pressure to obtain 2-methyl-6-nitropyridin-3-ol (700 mg, yield 86%). MS m/z (ESI): 155 [M+H]$^+$.

Step 2: Preparation of 2-chloro-4-((2-methyl-6-nitropyridin-3-yl)oxy)pyrimidine

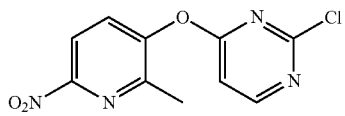 [SMILES: Cc1nc([N+](=O)[O-])ccc1Oc1ccnc(Cl)n1]

2-methyl-6-nitropyridin-3-ol (700 mg, 4.5 mmol) was dissolved in N,N-dimethylacetamide (25 mL), 2,4-dichloropyrimidine (1.0 g, 6.75 mmol) and potassium carbonate (1.24 g, 9.0 mmol) were added to the above solution. The reaction solution was stirred at 80° C. for 2 hrs, then cooled to room temperature, diluted with water (50 mL), and extracted with ethyl acetate (50 mL*3). The organic phases were combined, dried over anhydrous sodium sulfate, and filtered, and the solvent was removed under reduced pressure. The obtained crude product was separated by column chromatography (eluent: petroleum ether~petroleum ether/ethyl acetate (1:1)) to obtain 2-chloro-4-((2-methyl-6-nitropyridin-3-yl)oxy pyrimidine (478 mg, yield 40%). MS m/z (ESI): 267 [M+H]$^+$.

Step 3: Preparation of 2-(1-methyl-1H-pyrazol-4-yl)-4-((2-methyl-6-nitropyridin-3-yl)oxy)pyrimidine

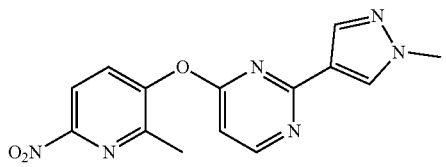 [SMILES: Cc1nc([N+](=O)[O-])ccc1Oc1ccnc(-c2cnn(C)c2)n1]

2-chloro-4-((2-methyl-6-nitropyridin-3-yl)oxy)pyrimidine (180 mg, 0.67 mmol) was dissolved in a mixture solution (1,4-dioxane: water=6:1, 3.5 mL). 1-methyl-4-(4,4,5,5-tetramethyl-1,3,2-dioxaborolan-2-yl)-1H-pyrazole (169 mg, 0.81 mmol), potassium carbonate (185 mg. 1.34 mmol), and palladium [1,1'-dikis(diphenylphosphino)ferrocene]dichloride (60 mg, 0.08 mmol) were added to the above solution. The reaction solution underwent air change twice under a nitrogen atmosphere and reacted at 90° C. for 16 hrs. The reaction solution was cooled to room temperature and then diluted with ethyl acetate, and extracted with water. The organic phase was dried and concentrated, and then separated by column chromatography (eluent: petroleum ether~ethyl acetate in a ratio of 1:3) to obtain 2-(1-methyl-1H-pyrazol-4-yl)-4-((2(2-methyl-6-nitropyridin-3-yl)oxy)pyrimidine (130 mg, yield 62%). MS m/z (ESI): 313 [M+H]$^+$.

Preparation of Intermediate E23: N-(4-((2-methyl-6-nitropyridin-3-yl)oxy)pyridin-2-yl) acetamide

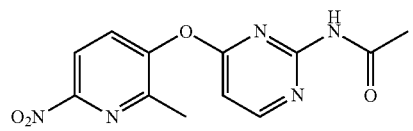 [SMILES: CC(=O)Nc1nccc(Oc2ccc([N+](=O)[O-])nc2C)n1]

3-((2-chloropyridin-4-yl)oxy)-2-methyl-6-nitropyridine (200 mg, 0.75 mmol) was dissolved in 1,4-dioxane (15 mL). Acetamide (266 mg, 4.52 mmol), cesium carbonate (731 mg, 2.25 mmol), 2-(dicyclohexylphosphino)-2,4,6-triisopropylbiphenyl (142 mg, 0.3 mmol), and tris (dibenzylideneacetone) dipalladium (137 mg, 0.15 mmol) were added. The nitrogen was charged to replace three times by evacuation, and then the reaction solution was stirred at 100° C. for 16 hrs. Ethyl acetate and water were added, and the mixture was separated. The organic phase was successively washed with water and a saturated brine, then dried over anhydrous sodium sulfate, filtered, concentrated, and separated by column chromatography (eluent: petroleum ether/ethyl acetate (2:1)~(1:1)) to obtain N-(4-((2-methyl-6-nitropyridin-3-yl)oxy)pyridin-2-yl) acetamide (200 mg, yield 76%). MS m/z (ESI): 289 [M+H]$^+$.

Preparation of Intermediate E24: 4-methyl-N-(4-((2-methyl-6-nitropyridin-3-yl)oxy)pyridin-2-yl) piperazine-1-carboxamide

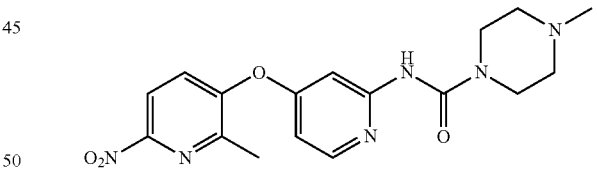

Step 1: Preparation of 4-methylpiperazine-1-carboxamide

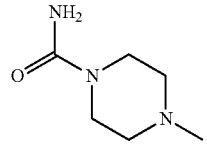

N-methylpiperazine (1.17 g, 11.74 mmol) was dissolved in isopropanol (30 mL), trimethylsilyl isocyanate (2,38 g, 20,72 mmol) was added, and the reaction solution was stirred at room temperature for 16 hrs under a nitrogen atmosphere. The solution was concentrated to obtain 4-methylpiperazine-1-carboxamide (1.7 g, yield 100%). MS m/z (ESI): 144 [M+H]⁺.

Step 2: preparation of 4-methyl-N-(4-((2-methyl-6-nitropyridin-3-yl)oxy)pyridin-2-yl) piperazine-1-carboxamide

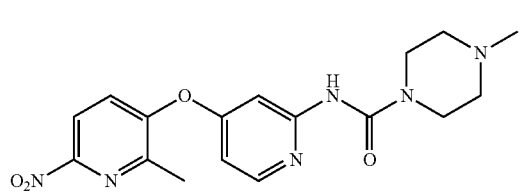 [SMILES: Cc1nc([N+](=O)[O-])ccc1Oc1ccnc(NC(=O)N2CCN(C)CC2)c1]

3-((2-chloropyridin-4-yl)oxy)-2-methyl-6-nitropyridine (500 mg, 1.88 mmol), 4-methylpiperazine-1-carboxamide (538 mg, 3.76 mmol), cesium carbonate (1.53 g. 4.7 mmol), tris(dibenzylideneacetone)dipalladium (173 mg, 0.19 mmol), and 2-dicyclohexylphosphoro-2,4,6-triisopropylbiphenyl (180 mg, 0.38 mmol) were added to a dry three-necked flask. The nitrogen was charged to replace three times by evacuation. Anhydrous 1,4-dioxane (18 mL) was added, and the reaction solution was stirred overnight at 110° C. After the reaction completed, the solution was diluted with ethyl acetate (30 mL), and filtered through the celite pad to remove the solid. The filtrate was concentrated and separated by column chromatography (eluent: dichloromethane dichloromethane/methanol (10:1)) to obtain 4-methyl-N-(4-((2-methyl-6-nitropyridin-3-yl)oxy)pyridin-2-yl)piperazine-1-carboxamide (400 mg, yield 58%). MS m/z (ESI): 373 [M+H]⁺.

Intermediates E25 and E26 were prepared according to the synthesis method of the intermediate E23.

Preparation of Intermediate F1 : 6-methyl-5-((2-(1-methyl-1H-pyrazol-4-yl)pyridin-4-yl) oxy)pyridin-2-amine

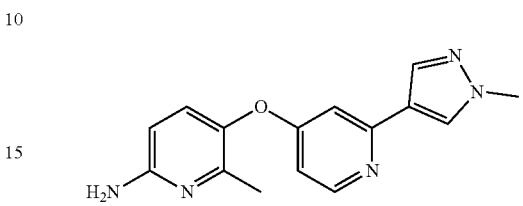

2-methyl-3-((2-(1-methyl-1H-pyrazol-4-yl)pyridin-4-yl) oxy)-6-nitropyridine (300 mg, 0.96 mmol) was dissolved in the mixture of ethanol/water (30 mL/15 mL). Iron powder (430 mg, 7.68 mmol) and ammonium chloride (518 mg, 9.60 mmol) were added. The reaction solution was stirred at 95° C. for 2 hrs. Dichloromethane and water were added, then the mixture was separated. The organic phase was successively washed with water and a saturated brine, then dried over anhydrous sodium sulfate, filtered, and concentrated to obtain 6-methyl-5-((2-(1-methyl-1H-pyrazol-4-yl)pyridin-4-yl)oxy)pyridin-2-amine (250 mg, yield 94%) MS m/z (ESI): 282 [M+H]⁺.

Intermediates F2-F26 were prepared according to the synthesis method of the intermediate F1.

| Intermediate No. | Structural formula | English name | MS m/z (ESI): [M + H]⁺ |
|---|---|---|---|
| E25 | | 1-methyl-N-(4-((2-methyl-6-nitropyridin-3-yl)oxy)pyridin-2-yl)piperidine-4-carboxamide | 372 |
| E26 | | N-(4-((2-methyl-6-nitropyridin-3-yl)oxy)pyridin-2-yl)cyclopropanecarboxamide | 315 |

| Intermediate No. | Structural formula | English name | MS m/z (ESI): [M + H]+ |
|---|---|---|---|
| F2 | | 5-((2-(1-methyl-1H-pyrazol-4-yl)pyridin-4-yl)oxy)pyridin-2-amine | 268 |
| F3 | | 6-ethyl-5-((2-(1-methyl-1H-pyrazol-4-yl)pyridin-4-yl)oxy)pyridin-2-amine | 296 |
| F4 | | 6-methyl-5-((2'-methyl-[2,4'-bipyridin]-4-yl)oxy)pyridin-2-amine | 293 |
| F5 | | 6-Methyl-5-((2-(2-methylthiazol-5-yl)pyridin-4-yl)oxy)pyridin-2-amine | 299 |
| F6 | | 5-((2-(1-ethyl-1H-pyrazol-4-yl)pyridin-4-yl)oxy)-6-methylpyridin-2-amine | 296 |
| F7 | | 5-((2-(1-(2-methoxyethyl)-1H-pyrazol-4-yl)pyridin-4-yl)oxy)-6-methylpyridin-2-amine | 326 |
| F8 | | 6-methyl-5-((2-(1-(2-morpholinoethyl)-1H-pyrazol-4-yl)pyridin-4-yl)oxy)pyridin-2-amine | 381 |
| F11 | | 6-methyl-5-((2-(1-(methyl-$d_3$)-1H-pyrazol-4-yl)pyridin-4-yl)oxy)pyridin-2-amine | 285 |

-continued

| Intermediate No. | Structural formula | English name | MS m/z (ESI): [M + H]+ |
|---|---|---|---|
| F12 | | (S)-6-methyl-5-((2-(1-(tetrahydrofuran-3-yl)-1H-pyrazol-4-yl)pyridin-4-yl)oxy)pyridin-2-amine | 338 |
| F13 | | 5-((2-(1-isopropyl-1H-pyrazol-4-yl)pyridin-4-yl)oxy)-6-methylpyridin-2-amine | 310 |
| F14 | | 6-methyl-5-((2-(1-propyl-1H-pyrazol-4-yl)pyridin-4-yl)oxy)pyridin-2-amine | 310 |
| F15 | | 5-((2-(1-cyclopropyl-1H-pyrazol-4-yl)pyridin-4-yl)oxy)-6-methylpyridin-2-amine | 308 |
| F16 | | 1-(4-(4-((6-amino-2-methylpyridin-3-yl)oxy)pyridin-2-yl)-1H-pyrazol-1-yl)-2-methylpropan-2-ol | 340 |
| F17 | | 6-methyl-5-((2-(1-(1-methylpyrrolidin-3-yl)-1H-pyrazol-4-yl)pyridin-4-yl)oxy)pyridin-2-amine | 351 |
| F18 | | 6-methyl-5-((2-(1-(oxetan-3-yl)-1H-pyrazol-4-yl)pyridin-4-yl)oxy)pyridin-2-amine | 324 |
| F19 | | 6-methyl-5-((2-(1-methyl-1H-imidazol-4-yl)pyridin-4-yl)oxy)pyridin-2-amine | 282 |

-continued

| Intermediate No. | Structural formula | English name | MS m/z (ESI): [M + H]+ |
|---|---|---|---|
| F20 | | 6-methyl-5-((2-(4-methyl-1H-imidazol-1-yl)pyridin-4-yl)oxy)pyridin-2-amine | 282 |
| F22 | | 6-methyl-5-((2-(1-methyl-1H-pyrazol-4-yl)pyrimidin-4-yl)oxy)pyridin-2-amine | 283 |
| F23 | | N-(4-((6-amino-2-methylpyridin-3-yl)oxy)pyridin-2-yl)acetamide | 259 |
| F24 | | N-(4-((6-amino-2-methylpyridin-3-yl)oxy)pyridin-2-yl)-4-methylpiperazine-1-carboxamide | 343 |
| F25 | | N-(4-((6-amino-2-methylpyridin-3-yl)oxy)pyridin-2-yl)-1-methylpiperidine-4-carboxamide | 342 |
| F26 | | N-(4-((6-amino-2-methylpyridin-3-yl)oxy)pyridin-2-yl)cyclopropanecarboxamide | 285 |

Preparation of Intermediate F9: Tert-butyl 4-(4-((6-amino-2-methylpyridin-3-yl)oxy)pyridin-2-yl)-1H-pyrazole-1-carboxylate Step 1: Preparation of tert-butyl 4-(4-((2-methyl-6-nitropyridin-3-yl)oxy)pyridin-2-yl)-1H-pyrazole-1-carboxylate

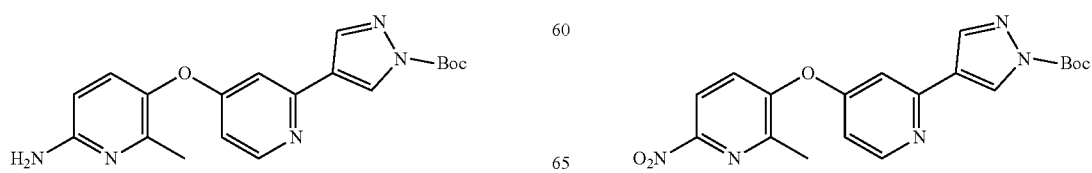

3-((2-(1H-pyrazol-4-yl)pyridin-4-yl)oxy)-2-methyl-6-nitropyridine (200 mg, 0.67 mmol) was dissolved in dichloromethane (5 mL). Triethylamine (135 mg, 1.34 mmol), 4-dimethylaminopyridine (8 mg, 0.067 mmol), and di-tert-butyl dicarbonate (294 mg, 1.34 mmol) were added. The reaction solution was stirred at room temperature for 1 hr, then poured into water (50 mL), and then extracted with dichloromethane (20 mL*2). The organic phases were combined and washed once with a brine (20 mL), dried over sodium sulfate, filtered, and then concentrated to obtain a crude product of tert-butyl 4-(4-((2-methyl-6-nitropyridin-3-yl)oxy)pyridin-2-yl)-1H-pyrazole-1-carboxylate (270 mg, yield 100%). MS m/z (ESI): 398 [M+H]+.

Step 2: Preparation of tert-butyl 4-(4-((6-amino-2-methylpyridin-3-yl)oxy)pyridin-2-yl)-1H-pyrazole-1-carboxylate

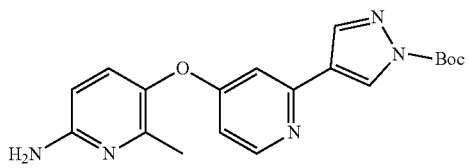 [SMILES: Cc1nc([N+](=O)[O-])ccc1Oc1ccnc(-c2cnn(C(=O)OC(C)(C)C)c2)c1]

Tert-butyl 4-(4-((2-methyl-6-nitropyridin-3-yl)oxy)pyridin-2-yl)-1H-pyrazole-1-carboxylate (240 mg, 0.6 mmol) was dissolved in methanol (15 mL), and 10% palladium on carbon (24 mg) was added. The nitrogen was charged to replace three times by evacuation. The reaction solution was stirred for 22 hrs under a hydrogen atmosphere. Then the solution was filtered, and the filtrate was concentrated to obtain a crude product of tert-butyl 4-(4-((6-amino-2-methylpyridin-3-yl)oxy)pyridin-2-yl)-1H-pyrazole-1-carboxylate (200 mg, yield 91%). MS m/z (ESI): 368 [M+H]+.

Preparation of Intermediate F10: 5-((2-(1-(2-((tert-butyldimethylsilyl)oxy)ethyl)-1H-pyrazol-4-yl)pyridin-4-yl)oxy)-6-methylpyridin-2-amine

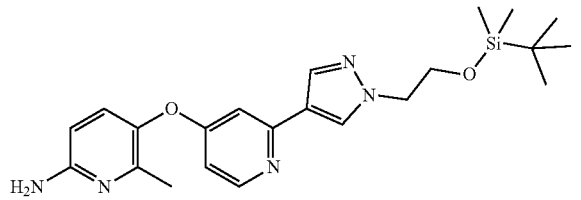 [SMILES: Cc1nc(N)ccc1Oc1ccnc(-c2cnn(CCO[Si](C)(C)C(C)(C)C)c2)c1]

3-((2-(1-(2-((tert-butyldimethylsilyl)oxy)ethyl)-1H-pyrazol-4-yl)pyridin-4-yl)oxy)-2-methyl-6-nitropyridine (3.7 g, 8.13 mmol) was dissolved in methanol (150 mL), and 7 M ammonia-methanol solution (2 mL) and 10% palladium on carbon (400 mg) were added. The nitrogen was charged to replace three times by evacuation. The reaction solution was stirred for 16 hrs under hydrogen atmosphere. The solution was filtered, and the filtrate was concentrated to obtain a crude product of 5-((2-(1-(2-((tert-butyldimethylsilyl)oxy)ethyl)-1H-pyrazol-4-yl)pyridin-4-yl)oxy)-6-methylpyridin-2-amine (3.0 g, yield 87%). MS m/z (ESI): 426 [M+H]+.

Preparation of Intermediate F21: 6-methyl-5-((2-(1-methyl-1H-pyrazol-4-yl)pyridin-4-yl)methyl)pyridin-2-amine

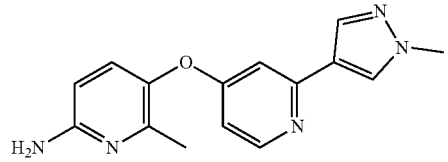 [SMILES: Cc1nc(N)ccc1Oc1ccnc(-c2cnn(C)c2)c1]

2-methyl-3-((2-(1-methyl-1H-pyrazol-4-yl)pyridin-4-yl)methyl)-6-nitropyridine (250 mg, 0.81 mmol) and 10% palladium on carbon (30 mg) were added to methanol (20 mL). The reaction solution was stirred at room temperature for 2 hrs under a hydrogen atmosphere. When the LCMS showed that the reaction completed, the reaction solution was filtered through celite, and the filtrate was concentrated to dryness. The residue was separated by a rapid silica gel column (0-10% MeOH:DCM) to obtain 6-methyl-5-((2-(1-methyl-1H-pyrazol-4-yl)pyridin-4-yl)methyl)pyridin-2-amine (150 mg, yield 66%). MS m/z (ESI): 280 [M+H]+.

Preparation of Intermediate F27: 4-((6-amino-2-methylpyridin-3-yl)oxy)-N-methylpicolinamide

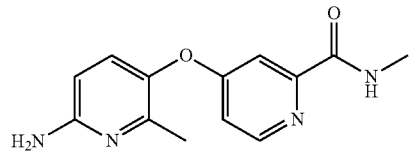 [SMILES: CNC(=O)c1cc(Oc2ccc(N)nc2C)ccn1]

Step 1: Preparation of 6-iodo-2-methylpyridin-3-ol

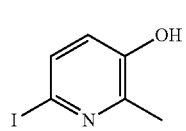

Sodium carbonate (20.5 g, 193.4 mmol) and iodine (23.6 g, 92.9 mmol) were added to the solution of 2-methylpyridin-3-ol (13.5 g, 123.8 mmol) in the mixture of methanol/water (100 mL/160 mL). The reaction solution was stirred at room temperature for 2 hrs. The pH of the solution was adjusted to 3 with concentrated hydrochloric acid. Dichloromethane and water were added, then the mixture was separated. The organic phase was successively washed with water and a saturated brine, and then dried over anhydrous sodium sulfate, filtered, and concentrated. The crude product was reslurried with dichloromethane, and then filtered to obtain 6-iodo-2-methylpyridin-3-ol (8.4 g, yield 38%). MS m/z (ESI): 236 [M+H]+.

Step 2: Preparation of methyl 4-((6-iodo-2-methylpyridin-3-yl)oxy)picolinate

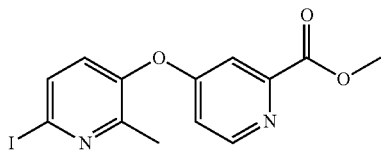 [SMILES: COC(=O)c1cc(Oc2ccc(I)nc2C)ccn1]

Methyl 4-chloropicolinate (8.73 g, 51 mmol) and potassium carbonate (7.0 g, 51 mmol) were added to the solution of 6-iodo-2-methylpyridin-3-ol (6.0 g, 25.5 mmol) in N,N-dimethylformamide (50 mL). The reaction solution was stirred overnight at 100° C. Dichloromethane and water were added, then the mixture was separated. The organic phase was successively washed with water and a saturated brine, then dried over anhydrous sodium sulfate, filtered, concentrated, and then separated by column chromatography (petroleum ether/ethyl acetate in a ratio of 3:1) to obtain 4-((6-iodo-2-methylpyridin-3-yl)oxy)picolinate (3.3 g, yield 34%), MS m/z (ESI): 371 [M+H]$^+$.

Step 3: Preparation of 4-((6-iodo-2-methylpyridin-3-yl)oxy) picolinic acid

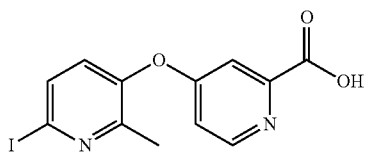 [SMILES: Cc1nc(I)ccc1Oc1ccnc(C(=O)O)c1]

Lithium hydroxide (3.7 g, 89 mmol) was added to methyl 4-((6-iodo-2-methylpyridin-3-yl)oxy)picolinate (3.3 g, 8.9 mmol) in a methanol/tetrahydrofuran/water (10 mL/10 mL/10 mL) solution. The reaction solution was stirred at room temperature for 1 hr. The pH of the solution was adjusted to 6 with 1 M hydrochloric acid, and then the solution was extracted three times with dichloromethane. The organic phase was successively washed with water and a saturated brine, then dried over anhydrous sodium sulfate, filtered, and concentrated to obtain 4-((6-iodo-2-methylpyridin-3-yl)oxy) picolinic acid (3.2 g, yield 100%). MS m/z (ESI): 357 [M+H]$^+$.

Step 4: Preparation of 4-((6-iodo-2-methylpyridin-3-yl)oxy)picolinoyl chloride

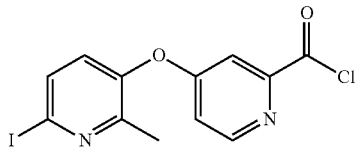 [SMILES: Cc1nc(I)ccc1Oc1ccnc(C(=O)Cl)c1]

Oxalyl chloride (2.8 g, 22.4 mmol) and N,N-dimethylformamide (1 drop) were added to 4-((6-iodo-2-methylpyridin-3-yl)oxy)picolinic acid (2.0 g, 5.6 mmol) in a dichloromethane solution (50 mL). The reaction solution was stirred at room temperature for 1 hr. The solution was concentrated to obtain 4-((6-iodo-2-methylpyridin-3-yl)oxy)picolinoyl chloride (2.1 g, yield 100%) which was directly used in the next step reaction. MS m/z (ESI): 375 [M+H]$^+$.

Step 5: Preparation of 4-((6-iodo-2-methylpyridin-3-yl)oxy)-N-methylpicolinamide

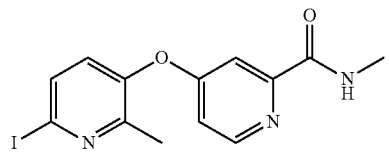 [SMILES: CNC(=O)c1cc(Oc2ccc(I)nc2C)ccn1]

N,N-diisopropylethylamine (2.1 g, 16.8 mmol) and 4-((6-iodo-2-methylpyridin-3-yl) oxy)picolinoyl chloride (2.1 g, 5.6 mmol) were added to the 2 M solution of methylamine in tetrahydrofuran (20 mL, 40 mmol). The reaction solution was stirred at room temperature for 30 min. Dichloromethane and water were added, then the mixture was separated. The organic phase was successively washed with water and a saturated brine, then dried over anhydrous sodium sulfate, filtered, concentrated, and then separated by column chromatography (petroleum ether/ethyl acetate (2:1)) to obtain 4-((6-iodo-2-methylpyridin-3-yl)oxy)methylpicolinamide (700 mg, yield 34%). MS m/z (ESI): 370 [M+H]$^+$.

Step 6: Preparation of tert-butyl (6-methyl-5-((2-(methylcarbamoyl)pyridin-4-yl)oxy)pyridin-2-yl) carbamate

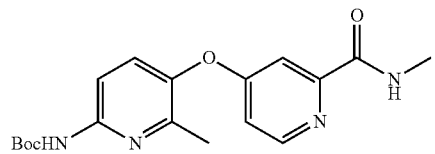 [SMILES: CNC(=O)c1cc(Oc2ccc(NC(=O)OC(C)(C)C)nc2C)ccn1]

4-((6-iodo-2-methylpyridin-3-yl)oxy)-N-methylpicolinamide (700 mg, 1.9 mmol) was dissolved in 1,4-dioxane (50 mL), and tert-butyl carbamate (1.1 g, 9.5 mmol), cesium carbonate (1.8 g, 5.7 mmol), palladium 1,1'-didiphenylphosphineferrocenedichloride (347 mg, 0.38 mmol), and 2-(dicyclohexylphosphino)-2',4',6'-triisopropyl-1,1'-biphenyl (360 mg, 0.76 mmol) were added. The nitrogen was charged to replace three times by evacuation, then the reaction solution was stirred at 100° C. for 16 hrs. The solution was filtered, concentrated, and then separated by column chromatography (dichloromethane/methanol in a ratio of 1:1) to obtain tert-butyl (6-methyl-5-((2-(methylcarbamoyl)pyridin-4-yl)oxy)pyridin-2-yl)carbamate (80 mg, yield 11%). MS m/z (ESI): 359 [M+H]$^+$.

Step 7: Preparation of 4-((6-amino-2-methylpyridin-3-yl)oxy)-N-methylpicolinamide

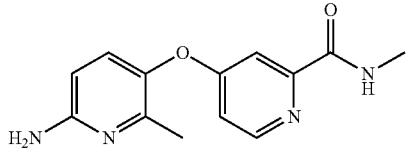 [SMILES: CNC(=O)c1cc(Oc2ccc(N)nc2C)ccn1]

The solution of tert-butyl (6-methyl-5-((2-(methylcarbamoyl)pyridin-4-yl)oxy)pyridin-2-yl) carbamate (80 mg, 0.22 mmol) in 1 M solution of hydrochloric acid/ethyl acetate (6 mL, 6 mmol) was stirred at room temperature for 1 hr. The solution was concentrated to obtain 4-((6-amino-2-methylpyridin-3-yl)oxy)-N-methylpicolinamide (40 mg, yield 70%). MS m/z (ESI): 259 [M+H]$^+$.

Preparation of Intermediate 3,3-dimethylpyrrolidine-2-one

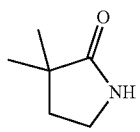

Step 1: Preparation of tert-butyl 2-oxopyrrolidine-1-carboxylate

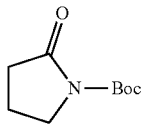 [SMILES: CC(C)(C)OC(=O)N1CCCC1=O]

Pyrrolidin-2-one (2.5 g, 29.4 mmol) was dissolved in dichloromethane (100 mL), and di-tert-butyldicarbonate (12.83 g, 58.8 mmol), 4-dimethylaminopyridine (3.6 g, 29.4 mmol), and triethylamine (2.95 g, 29.4 mmol) were added. The reaction solution was stirred at room temperature for 2 hrs. Dichloromethane and water were added, then the mixture was separated. The organic phase was successively washed with water and a saturated brine, then dried over anhydrous sodium sulfate, filtered, concentrated, and then separated by column chromatography (eluent: petroleum ether/ethyl acetate (30:1)~(9:1)) to obtain tert-butyl 2-oxopyrrolidine-1-carboxylate (4.6 g, yield 84%). MS m/z (ESI):393 [M+H]$^+$.

Step 2: Preparation of tert-butyl 3,3-dimethyl-2-oxopyrrolidine-1-carboxylate

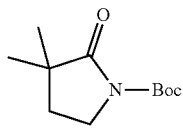

Tert-butyl 2-oxopyrrolidine-1-carboxylate (2.0 g. 10.8 mmol) was dissolved in tetrahydrofuran (100 mL), and 1 M solution of lithium bis(trimethylsilyl)amide tetrahydrofuran (32 mL, 32.4 mmol) was added at −78° C. After the mixture solution was stirred for 30 minutes, methyl iodide (9.23 g, 65 mmol) was added to above solution. The reaction solution was stirred at −78° C. for 40 min, and then stirred at room temperature for 2 hrs. Ethyl acetate and water were added, then the solution was separated. The organic phase was successively washed with water and a saturated brine, then dried over anhydrous sodium sulfate, filtered, concentrated, and separated by column chromatography (eluent: petroleum ether/ethyl acetate (30:1)~(9:1)) to obtain tert-butyl 3,3-dimethyl-2-oxopyrrolidine-1-carboxylate (1.3 g, yield 56%). MS na/z. (ESI): 449 [2M+Na]$^+$.

Step 3: Preparation of 3,3-dimethylpyrrolidin-2-one

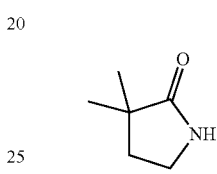

Tert-butyl 3,3-dimethyl-2-oxopyrrolidine-1-carboxylate (2.3 g, 10.7 mmol) was dissolved in a 4 M solution of hydrochloric acid in 1,4-dioxane (10 mL). The reaction solution was stirred at room temperature for 2 hrs. A 7 M solution of ammonia in methanol was added, and the mixture solution was concentrated, the residue solid was washed twice with methyl tert-butyl ether. The organic phase was combined and concentrated to obtain 3,3-dimethylpyrrolidin-2-one (1.09 g, yield 89%). MS m/z (ESI): 227 [2M+Na]$^+$.

Preparation of Intermediate G2: 3,3-dimethylpiperidin-2-one

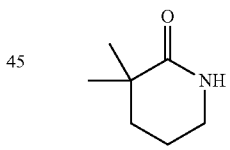

Step 1: Preparation of tert-butyl 2-oxopiperidine-1-carboxylate

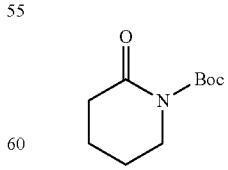

Piperidin-2-one (5.0 2, 50 mmol) was dissolved in dichloromethane (100 mL), and di-tert-butyldicarbonate (13.0 g, 60 mmol), 4-dimethylaminopyridine (6.15 g, 50 mmol), and N,N-diisopropylethylamine (12.9 g, 100 mmol) were added. The reaction solution was stirred overnight at room temperature. Dichloromethane and water were added, then the mixture was separated. The organic phase was successively washed with water and a saturated brine, then dried over anhydrous sodium sulfate, filtered, concentrated, and then separated by column chromatography (petroleum ether/ethyl acetate in a ratio of 2:1) to obtain tert-butyl 2-oxopiperidine-1-carboxylate (8.5 g, yield 84%). MS m/z (ESI): 393 [2M+Na]⁺.

Step 2: Preparation of tert-butyl 3,3-dimethyl-2-oxopiperidine-1-carboxylate

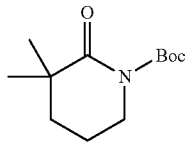 [SMILES: CC(C)(C)OC(=O)N1CCCC(C)(C)C1=O]

Tert-butyl 2-oxopiperidine-1-carboxylate (5.1 g, 25 mmol) was dissolved in tetrahydrofuran (50 mL), and 1 M solution of lithium bis(trimethylsilyl)amide in tetrahydrofuran (100 mL, 100 mmol) was added at −78° C. After the mixture was stirred for 30 mM, methyl iodide (17.75 g, 125 mmol) was added. The reaction solution was stirred at −78° C. for 40 min, and then stirred at room temperature for 2 hrs. Ethyl acetate and water were added, then the mixture was separated. The organic phase was successively washed with water and a saturated brine, then dried over anhydrous sodium sulfate, filtered, concentrated, and then separated by column chromatography (petroleum ether/ethyl acetate in a ratio of 5:1) to obtain tert-butyl 3,3-dimethyl-2-oxopiperidine-1-carboxylate (3.0 g, yield 52%). MS m/z (ESI): 421 [2M+Na]⁺.

Step 3: Preparation of 3,3-dimethylpiperidin-2-one

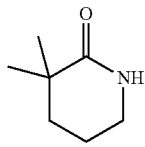

Tert-butyl 3,3-dimethyl-2-oxopiperidine-1-carboxylate (3.0 g, 13 mmol) was dissolved in a 4 M solution of hydrochloric acid in 1,4-dioxane (39 mL). The reaction solution was stirred at room temperature for 2 hrs, then concentrated, and then a 7 M solution of ammonia in methanol was added. The mixture was concentrated, the residue solid was washed twice with methyl tert-butyl ether. The organic phase was combined and concentrated to obtain 3.3-dimethylpiperidin-2-one (1.5 g, yield 90%). MS m/z (ESI): 277 [2M+Na]⁺.

Preparation of Intermediate G3: 2,2-dimethylmorpholin-3-one

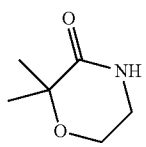

Step 1: Preparation of 2-((tert-butyldimethylsilyl)oxy)-N-(2,4,6-trimethoxybenzyl)ethan-1-amine

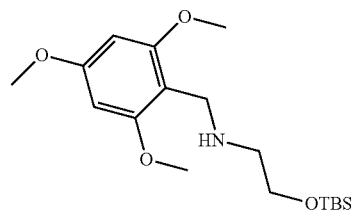 [SMILES: COc1cc(OC)c(CNCCO[Si](C)(C)C(C)(C)C)c(OC)c1]

2-((tert-butyldimethylsilyl)oxy)ethan-1-amine (1.75 g, 8.9 mmol) was dissolved in 1,2-dichloroethane (20 mL), and 2,4,6-trimethoxybenzaldehyde (1.75 g, 8.9 mmol) was added. After the reaction solution was stirred overnight at room temperature, sodium borohydride (760 mg, 20 mmol) was added. After the reaction solution was continuously stirred for 2 hrs, dichloromethane and water were added, then the mixture was separated. The organic phase was successively washed with water and a saturated brine, then dried over anhydrous sodium sulfate, filtered, concentrated, and then separated by column chromatography to obtain 2-((tert-butyldimethylsilyl)oxy)-N-(2,4,6-trimethoxybenzyl)ethan-1-amine (2 g, yield 63%). MS m/z (ESI): 356 [M+1]⁺.

Step 2: Preparation of 2-bromo-N-(2-((tert-butyldimethylsilyl)oxy)ethyl)-2-methyl-N-(2,4,6-trimethoxybenzyl)propanamide

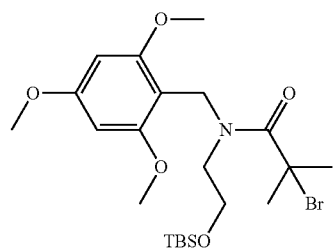 [SMILES: COc1cc(OC)c(CN(CCO[Si](C)(C)C(C)(C)C)C(=O)C(C)(C)Br)c(OC)c1]

2-((tert-butyldimethylsilyl)oxy)-N-(2,4,6-trimethoxybenzyl)ethan-1-amine (2.0 g, 5.6 mmol) was dissolved in dichloromethane (20 mL) under an ice bath. Triethylamine (1.13 g, 11.2 mmol) and 2-promo-2-methylpropionyl bromide (1.4 g, 6.2 mmol) were added. The reaction solution was stirred for 30 min under an ice bath. Dichloromethane and water were added, then the mixture was separated. The organic phase was successively washed with water and a saturated brine, then dried over anhydrous sodium sulfate, filtered, concentrated, and then separated by column chromatography to obtain 2-bromo-N-(2-((tert-butyldimethylsilyl)oxy)ethyl)-2-methyl-N-(2,4,6-trimethoxybenzyl)propanamide (2.4 g, yield 85%). MS m/z (ESI): 504 [M+H]⁺.

Step 3: Preparation of 2-bromo-N-(2-hydroxyethyl)-2-methyl-N-(2,4,6-trimethoxybenzyl)propanamide

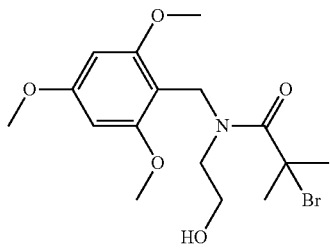 [SMILES: COc1cc(OC)c(CN(CCO)C(=O)C(C)(C)Br)c(OC)c1]

2-bromo-N-(2-((tert-butyldimethylsilyl)oxy)ethyl)-2-methyl-N-(2,4,6-trimethoxybenzyl)propanamide (2.4 g, 4.7 mmol) was dissolved in a 1 M solution of tetrabutylammonium fluoride in tetrahydrofuran (9.4 mL, 9.4 mmol). The reaction solution was stirred at room temperature for 30 min. Dichloromethane and water were added, then the mixture was separated. The organic phase was successively washed with water and a saturated brine, then dried over anhydrous sodium sulfate, filtered, concentrated, and then separated by column chromatography to obtain 2-bromo-N-(2-hydroxyethyl)-2-methyl-N-(2,4,6-trimethoxybenzyl) propanamide (1.2 g, yield 63%). MS m/z (ESI): 390 [M+H]$^+$.

Step 4: Preparation of 2,2-dimethyl-4-(2,4,6-trimethoxybenzyl)morpholin-3-one

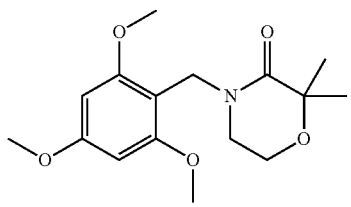

2-bromo-N-(2-hydroxyethyl)-2-methyl-2,4,6-trimethoxybenzyl)propanamide (1.2 g, 3 mmol) was dissolved in tetrahydrofuran (20 mL). Then potassium tert-butoxide (504 mg, 4.5 mmol) was added. The reaction solution was stirred at room temperature for 1 hr. Dichloromethane and water were added, then the mixture was separated. The organic phase was successively washed with water and a saturated brine, then dried over anhydrous sodium sulfate, filtered, concentrated, and then separated by column chromatography to obtain 2,2-dimethyl-4-(2,4,6-trimethoxybenzyl)morpholin-3-one (700 mg, yield 75%). MS m/z (ESI): 310 [M+H]$^+$.

Step 5: Preparation of 2,2-dimethylmorpholin-3-one

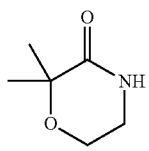

Trifluoromethanesulfonic acid (1 mL) was added to a solution of 2,2-dimethyl-4-(2,4,6-trimethoxybenzyl)morpholine-3-one (350 mg, 1.13 mmol) in toluene (8 mL). The reaction solution was stirred under microwave at 210° C. for 20 min, then concentrated, then a 7 M solution of ammonia in methanol was added, and then the mixture was concentrated again. The residue was dissolved in dichloromethane, then the mixture was filtered. The filtrate was concentrated to obtain 2,2-dimethylmorpholin-3-one (250 mg, yield 100%). MS m/z (ESI): 130 [M+H]$^+$.

Preparation of Intermediate G4: 3,3-dipropylpyrrolidin-2-one

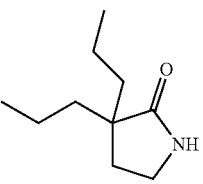

Step 1: Preparation of 3,3-diallylpyrrolidin-2-one

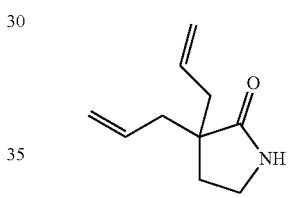

1 M of 1,1,1,3,3,3-lithium hexamethyldisilazane (48.6 mL, 48.6 mmol) was added to the solution of tert-butyl 2-oxopyrrolidine-1-carboxylate (3.0 g, 16.2 mmol) in tetrahydrofuran (80 mL) under a dry ice-acetone bath. After the mixture solution was stirred at −78° C. for 30 min, 3-bromoprop-1-ene (6.8 g, 56.7 mmol) was added. The reaction solution was stirred at −78° C. for 1 hr, and then stirred at room temperature for 2 hrs. The reaction solution was poured into ice water, and then extracted with ethyl acetate. The organic phase was successively washed with water and a saturated brine, then dried over anhydrous sodium sulfate, filtered, concentrated, and then separated by column chromatography (petroleum ether/ethyl acetate (1:1)) to obtain 3,3-diallylpyrrolidin-2-one (850 mg, yield 31%). MS m/z (ESI): 166 [M+H]$^+$.

Step 2: Preparation of tert-butyl 3,3-diallyl-2-oxopyrrolidine-1-carboxylate

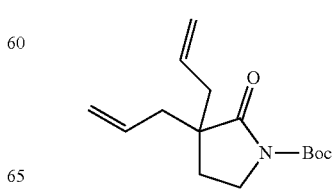

Triethylamine (520 mg, 5.15 mmol), di-tert-butyldicarbonate (2.2 g, 10.3 mmol), and 4-(dimethylamino)-pyridine (633 mg, 5.15 mmol) were added to a solution of 3,3-diallylpyrrolidin-2-one (850 mg, 5.15 mmol) in dichloromethane (20 mL). The reaction solution was stirred overnight at room temperature. Dichloromethane and water were added, then the mixture was separated. The organic phase was successively washed with water and a saturated brine, then dried over anhydrous sodium sulfate, filtered, concentrated, and then separated by column chromatography (petroleum ether/ethyl acetate (2:1)) to obtain tert-butyl 3,3-diallyl-2-oxopyrrolidine-1-carboxylate (750 mg, yield 55%). MS m/z (ESI): 266 [M+H]⁺.

Step 3: Preparation of tert-butyl 2-oxo-3,3-dipropylpyrrolidine-1-carboxylate

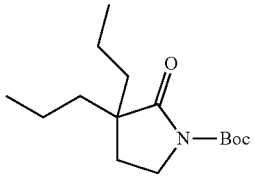 [SMILES: CCCC1(CCC)CCN(C(=O)OC(C)(C)C)C1=O]

10% palladium on carbon (50 mg) was added to a solution of tert-butyl 3,3-diallyl-2-oxopyrrolidine-1-carboxylate (200 mg, 0.75 mmol) in methanol (10 mL), and the reaction mixture was stirred overnight at room temperature under hydrogen atmosphere. The reaction mixture was filtered, and the filtrate was concentrated to obtain tert-butyl 2-oxo-3,3-dipropylpyrrolidine-1-carboxylate (200 mg, yield 100%). MS m/z (ESI): 270 [M+H]⁺.

Step 4: Preparation of 3,3-dipropylpyrrolidin-2-one

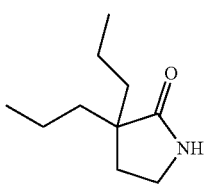

The mixture solution of tert-butyl 2-oxo-3,3-dipropylpyrrolidine-1-carboxylate (200 mg, 0.74 mmol) in a 1 M solution of hydrochloric acid in 1,4-dioxane (8 mL) was stirred at room temperature for 2 hrs. The reaction solution was concentrated, the residue was dissolved in a 7 M solution of ammonia in methanol, and then the mixture was concentrated again. The residue was treated with methyl tert-butyl ether, and then the mixture was filtered. The filtrate was concentrated to obtain 3,3-dipropylpyrrolidin-2-one (120 mg, yield 96%). MS m/z (ESI): 170 [M+H]⁺.

Preparation of Intermediate G5: 2-azaspiro[4.4]nonan-1-one

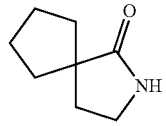

Step 1: Preparation of tert-butyl 1-oxo-2-azaspiro[4.4]non-7-ene-2-carboxylate

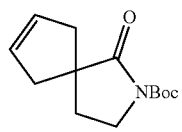 [SMILES: CC(C)(C)OC(=O)N1CCC2(CC=CC2)C1=O]

The second-generation Grubbs catalyst (160 mg, 0.188 mmol) was added to a solution of tert-butyl 3,3-diallyl-2-oxopyrrolidine-1-carboxylate (500 mg, 1.88 mmol) in dichloromethane (30 mL). The reaction solution was stirred overnight at room temperature. Dichloromethane and water were added, then the mixture was separated. The organic phase was successively washed with water and a saturated brine, then dried over anhydrous sodium sulfate, filtered, concentrated, and then separated by column chromatography (petroleum ether/ethyl acetate (3:1)) to obtain tert-butyl 1-oxo-2-azaspiro[4.4]non-7-ene-2-carboxylate (410 mg, yield 92%). MS m/z (ESI): 238 [M+H]⁺.

Step 2: Preparation of tert-butyl 1-oxo-2-azaspiro[4.4]nonane-2-carboxylate

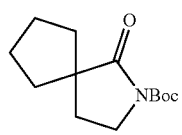 [SMILES: CC(C)(C)OC(=O)N1CCC2(CCCC2)C1=O]

Palladium on carbon (100 mg) was added to a solution of tert-butyl 1-oxo-2-azaspiro[4.4]non-7-ene-2-carboxylate (410 mg, 1.73 mmol) in methanol (10 mL). The reaction solution was stirred at room temperature for 2 hrs under a hydrogen atmosphere, then filtered. The filtrate is concentrated to obtain tert-butyl 1-oxo-2-azaspiro[4.4]nonane-2-carboxylate (400 mg, yield 96%). MS m/z (ESI): 240 [M+H]⁺.

Step 3: Preparation of 2-azaspirop[4.4]nonan-4-one

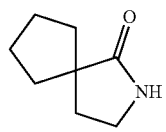

The mixture of tert-butyl 1-oxo-2-azaspiro[4.4]nonane-2-carboxylate (400 mg, 1.68 mmol) in a 1 M solution of hydrochloric acid in 1,4-dioxane (8 mL) was stirred at room temperature for 2 hrs. The reaction solution was concentrated, the residue was dissolved in a 7 M solution of ammonia in methanol, and then the mixture was concentrated again. The residue was treated with methyl tert-butyl ether, and then the mixture was filtered. The filtrate was concentrated to obtain 2-azaspiro[4.4]nonan-1-one (230 mg, yield 99%). MS m/z (ESI): 140 [M+H]$^+$.

Preparation of Intermediate G6: 3-methylpyrrolidin-2-one

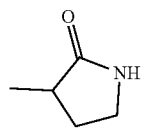

Step 1: Preparation of tert-butyl 3-methyl-2-oxopyrrolidine-1-carboxylate

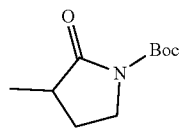

Tert-butyl 2-oxopyrrolidine-1-carboxylate (2.0 g, 10.81 mmol) was dissolved in tetrahydrofuran (50 mL). Lithium bis(trimethylsilyl)amide (13 mL, 13 mmol) was added dropwise at −78° C., and the mixture solution was stirred for 30 min. Then methyl iodide (1.61 g, 11.35 mmol) was added to the above solution, and the reaction solution was stirred at room temperature for 1 hr. A saturated ammonium chloride solution was added for quenching. The mixture solution was poured into water (150 mL) and then extracted with ethyl acetate (100 mL*2). The organic phases were combined and washed once with brine (100 mL), dried over sodium sulfate, filtered, concentrated, and then separated by column chromatography (eluent: petroleum ether~petroleum ether/ethyl acetate (85:15)) to obtain tert-butyl 3-methyl-2-oxopyrrolidine-1-carboxylate (0.6 g, yield 28%). MS m/z (ESI): 421 [2M+Na]$^+$.

Step 2: Preparation of 3-methylpyrrolidin-2-one

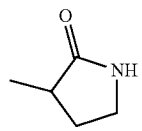

Tert-butyl 3-methyl-2-oxopyrrolidine-1-carboxylate (0.6 g, 3 mmol) was dissolved in solution of hydrochloric acid in ethyl acetate (10 m, 10 mmol). The reaction solution was stirred at room temperature for 4 hrs. A 7 M solution of ammonia in methanol (2 mL) was added, the mixture solution was concentrated, and then methyl tert-butyl ether (20 mL) was added to residue. After the mixture solution was filtered, the filtrate was concentrated to obtain a crude product of 3-methylpyrrolidin-2-one (300 mg, yield 100%). MS m/z (ESI): 199 [2M+H]$^+$.

Preparation of Intermediate G7-1: methyl 2-(cyanomethyl)-2-methylbutanoate

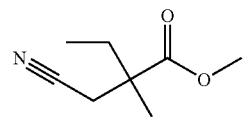

Methyl 2-methylbutanoate (5.0 g, 43.1 mmol) was dissolved in tetrahydrofuran (30 mL), and lithium diisopropylamide (23.7 mL, 47.4 mmol) was added dropwise at −78° C., and the mixture solution was stirred for 30 min. Then a solution of bromoacetonitrile (6.2 g, 51.7 mmol) in tetrahydrofuran (10 mL) was added. The reaction mixture was slowly warmed to room temperature and stirred at room temperature for 16 hrs, A 1 M of hydrochloric acid aqueous solution (75 mL) was added for quenching. The mixture solution was extracted with methyl tert-butyl ether (75 mL*3). The organic phases were combined and washed once with brine (100 mL), dried over magnesium sulfate and filtered, then concentrated at 0° C., and distilled under reduced pressure to obtain methyl 2-(cyanomethyl)-2-methylbutanoate (3.5 g, yield 57.5%).

Intermediates G8-1 and G9-1 were prepared according the synthesis method of the intermediate G7-1.

| Intermediate No. | Structural formula | English name | MS m/z (ESI): [M + H]$^+$ |
|---|---|---|---|
| G8-1 | | Methyl 2-(cyanomethyl)-2-ethylbutanoate | — |
| G9-1 | | Methyl 1-(cyanomethyl)cyclobutane-1-carboxylate | — |

Preparation of Intermediate G10-1: methyl 2-(benzyloxy)-3-cyano-2-methylpropanoate

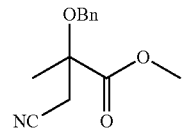

Step 1: Preparation of methyl 2-(benzyloxy)propanoate

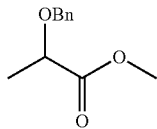

60% sodium hydride (5.7 g, 144 mmol) and benzyl bromide (19.6 g, 115 mmol) were added to a solution of methyl 2-hydroxypropanoate (10.0 g, 96 mmol) in tetrahydrofuran (100 mL). The reaction solution was stirred for 1 hr under an ice bath, and then stirred at room temperature for 1 hr. The reaction solution was poured into ice water, and then extracted with ethyl acetate. The organic phase was successively washed with water and a saturated brine, then dried over anhydrous sodium sulfate, filtered, concentrated, and then separated by column chromatography (petroleum ether/ethyl acetate (5:1)) to obtain methyl 2-(benzyloxy)propanoate (12.8 g, yield 68%). MS m/z (ESI): 195 [M+H]$^+$.

Step 2: Preparation of methyl 2-(benzyloxy)-3-cyano-2-methylpropanoate

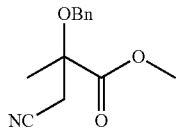 [SMILES: COC(=O)C(C)(CC#N)OCc1ccccc1]

2 M of lithium diisopropylamide (6.5 mL, 13 mmol) was added to a solution of methyl 2-(benzyloxy)propanoate (2.0 g, 10 mmol) in tetrahydrofuran (40 mL) under a dry ice-acetone bath. After the mixture solution was stirred at −78° C. for 30 min, bromoacetonitrile (1.8 g, 15 mmol) was added. The reaction solution was stirred at −78° C. for 1 hr, and then stirred at room temperature for 1 hr. Dichloromethane and saturated ammonium chloride were added, the mixture was separated. The organic phase was successively washed with water and a saturated brine, then dried over anhydrous sodium sulfate, filtered, concentrated, and then separated by column chromatography (petroleum ether/ethyl acetate (3:1)) to obtain methyl 2-(benzyloxy)-3-cyano-2-methylpropanoate (800 mg, yield 33%). MS m/z (ESI): 234 [M+H]$^{30}$.

Preparation of Intermediate G11-1: methyl 2-(cyanomethyl)-4-methoxy-2-methylbutanoate

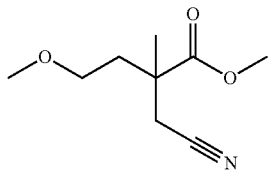

Step 1: Preparation of methyl 4-methoxy-2-methylbutanoate

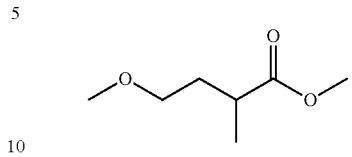

3-methyldihydrofuran-2(3H)-one (4.0 g, 40 mmol) was dissolved in methanol (40 mL), and triethyl orthoformate (8.48 g, 80 mmol) and concentrated sulfuric acid (100 mg) were added at room temperature. The reaction solution was stirred at room temperature for 16 hrs, then poured into water (200 mL), and then extracted with ethyl acetate (100 mL*2). Organic phases were combined and washed once with brine (100 mL), dried over sodium sulfate and filtered, and concentrated to obtain a crude product of methyl 4-methoxy-2-methylbutanoate (4.0 g, yield 68.5%). MS m/z (ESI): 147 [M+H]$^+$.

Step 2: Preparation of methyl 2-(cyanomethyl)-4-methoxy-2-methylbutanoate

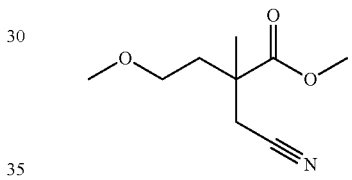

Methyl 4-methoxy-2-methylbutanoate (4.0 g, 27.36 mmol) was dissolved in tetrahydrofuran (100 mL), and lithium diisopropylamide (15.05 mL, 30.1 mmol) was added dropwise at −78° C., then the mixture solution was stirred for 30 min. Bromoacetonitrile (3.94 g, 32.83 mmol) was added, and the reaction solution was stirred at room temperature for 16 hrs. 1 M of hydrochloric acid aqueous solution (75 mL) was added for quenching. The solution was extracted with methyl tert-butyl ether (75 mL*3). Organic phases were combined and washed once with brine (100 mL), dried over sodium sulfate and filtered, then concentrated at 0° C., and distilled under reduced pressure to obtain methyl 2-(cyanomethyl)-4-methoxy-2-methylbutanoate (2.5 g, yield 49.5%).

Preparation of Intermediate G7: 3-ethyl-3-methylpyrrolidin-2-one

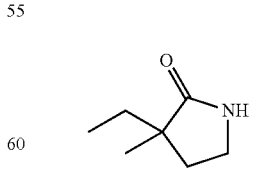

Methyl 2-(cyanomethyl)-2-methylbutanoate (1.5 g, 10 mmol) was dissolved in a solution of tetrahydrofuran in water (20 mL/10 mL), and cobalt chloride hexahydrate (1.19 g, 5 mmol) was added. Then sodium borohydride (1.9 g, 50 mmol) was slowly added under an ice bath. The reaction mixture was stirred at room temperature for 16 hrs. Concentrated ammonia liquor (5 mL) was added, then the mixture was filtered, and the solution was extracted with ethyl acetate (30 mL*2). The organic phases were combined and washed once with brine (40 mL), dried over sodium sulfate and filtered, then concentrated to obtain a crude product of 3-ethyl-3-methylpyrrolidin-2-one (600 mg, yield 47%). MS m/z (ESI): 128 [M+H]$^+$.

Intermediates G8, G9, G10, and G11 were prepared according to the synthesis method of the intermediate G7.

| Intermediate No. | Structural formula | English name | MS m/z (ESI): [M + H]$^+$ |
|---|---|---|---|
| G8 | | 3,3-diethylpyrrolidin-2-one | 142 |
| G9 | | 6-azaspiro[3.4]octan-5-one | 146 |
| G10 | | 3-(benzyloxy)-3-methylpyrrolidin-2-one | 206 |
| G11 | | 3-(2-methoxyethyl)-3-methylpyrrolidin-2-one | 158 |

PREPARATION OF EXAMPLES

Example 1: Preparation of 3,3-dimethyl-N-(6-methyl-5-((2-(1-methyl-1H-pyrazol-4-yl) pyridin-4-yl)oxy)pyridin-2-yl)-2-oxopyrrolidine-1-carboxamide

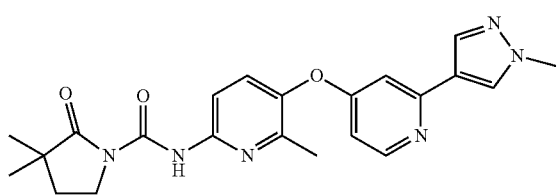

Step 1: Preparation of 3,3-dimethyl-2-oxopyrrolidine-1-carbonyl chloride

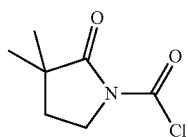

The solution of 3,3-dimethylpyrrolidin-2-one (200 mg, 1.75 mmol) and pyridine (415 mg, 5.26 mmol) in dichloromethane (5 mL) was added dropwise to the solution of triphosgene (172 mg, 0.58 mmol) in dichloromethane (5 mL) under an ice bath. The reaction solution was stirred at 5° C. for 30 min. The reaction solution was directly used in the next step without any treatment.

Step 2: Preparation of 3,3-dimethyl-N-(6-methyl-5-((2-(1-methyl-1H-pyrazol-4-yl)pyridin-4-yl)oxy)pyridin-2-yl-)-2-oxopyrrolidine-1-carboxamide

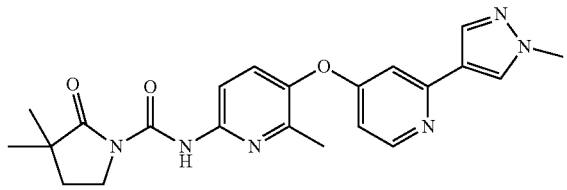

The solution of 3,3-dimethyl-2-oxopyrrolidine-1-carbonyl chloride (0.33 mmol) in dichloromethane (10 mL) obtained from the above reaction was added dropwise to the solution of 6-methyl-5-((2-(1-methyl-1H-pyrazol-4-yl)pyridin-4-yl)oxy)pyridin-2-amine (93 mg, 0.33 mmol) and pyridine (78 mg, 0.99 mmol) in dichloromethane (10 mL) under an ice bath. The reaction solution was stirred at 5° C. for 30 min, and then stirred at room temperature for 2 hrs. Dichloromethane and water was added, and then the mixture was separated. The organic phase was successively washed with water and a saturated brine, then dried over anhydrous sodium sulfate, filtered, concentrated, and separated by column chromatography [eluent: dichloromethane/methanol (15:1)] to obtain 3,3-dimethyl-N-(6-methyl-5-((2-(1-methyl-1H-pyrazol-4-yl)pyridin-4-yl)oxy)pyridin-2-yl)-2-oxopyrrolidine-1-carboxamide (42 mg, yield 30.4%). MS m/z (ESI): 421 [M+H]$^+$.

$^1$H NMR (400 MHz, DMSO-d$_6$) δ 11.02 (s, 1H), 8.37 (d, J=5.6 Hz, 1H), 8.27 (s, 1H), 7.98 (s, 1H), 7.93 (d, J=8.8 Hz, 1H), 7.67 (d, J=8.8 Hz, 1H), 7.19 (d, J=2.5 Hz, 1H), 6.62 (dd, J=5.7, 2.5 Hz, 1H), 3.86 (s, 3H), 3.78 (t, J=7.0 Hz, 2H), 2.28 (s, 3H), 1.91 (1,J=7.0 Hz, 2H), 1.20 (s, 6H).

Examples 2-8 and 11-40 were Prepared According to the Synthesis Method of Example 1

| Example No. | Structural formula | English name | MS m/z (ESI): [M + H]+ |
|---|---|---|---|
| 2 | | 3,3-dimethyl-N-(5-((2-(1-methyl-1H-pyrazol-4-yl)pyridin-4-yl)oxy)pyridin-2-yl)-2-oxopyrrolidine-1-carboxamide | 407 |
| 3 | | N-(6-ethyl-5-((2-(1-methyl-1H-pyrazol-4-yl)pyridin-4-yl)oxy)pyridin-2-yl)-3,3-dimethyl-2-oxopyrrolidine-1-carboxamide | 435 |
| 4 | | 3,3-dimethyl-N-(6-methyl-5-((2'-methyl-[2,4'-bipyridin]-4-yl)oxy)pyridin-2-yl)-2-oxopyrrolidine-1-carboxamide | 432 |
| 5 | | 3,3-dimethyl-N-(6-methyl-5-((2-(2-methylthiazol-5-yl)pyridin-4-yl)oxy)pyridin-2-yl)-2-oxopyrrolidine-1-carboxamide | 438 |
| 6 | | N-(5-((2-(1-ethyl-1H-pyrazol-4-yl)pyridin-4-yl)oxy)-6-methylpyridin-2-yl)-3,3-dimethyl-2-oxopyrrolidine-1-carboxamide | 435 |
| 7 | | N-(5-((2-(1-(2-methoxyethyl)-1H-pyrazol-4-yl)pyridin-4-yl)oxy)-6-methylpyridin-2-yl)-3,3-dimethyl-2-oxopyrrolidine-1-carboxamide | 465 |

-continued

| Example No. | Structural formula | English name | MS m/z (ESI): [M+H]+ |
|---|---|---|---|
| 8 | | 3,3-dimethyl-N-(6-methyl-5-((2-(1-(2-morpholinoethyl)-1H-pyrazol-4-yl)pyridin-4-yl)oxy)pyridin-2-yl)-2-oxopyrrolidine-1-carboxamide | 520 |
| 11 | | 3,3-dimethyl-N-(6-methyl-5-((2-(1-(methyl-d$_3$)-1H-pyrazol-4-yl)pyridin-4-yl)oxy)pyridin-2-yl)-2-oxopyrrolidine-1-carboxamide | 424 |
| 12 | | (S)-3,3-dimethyl-N-(6-methyl-5-((2-(1-(tetrahydrofuran-3-yl)-1H-pyrazol-4-yl)pyridin-4-yl)oxy)pyridin-2-yl)-2-oxopyrrolidine-1-carboxamide | 477 |
| 13 | | N-(5-((2-(1-isopropyl-1H-pyrazol-4-yl)pyridin-4-yl)oxy)-6-methylpyridin-2-yl)-3,3-dimethyl-2-oxopyrrolidine-1-carboxamide | 449 |
| 14 | | 3,3-dimethyl-N-(6-methyl-5-((2-(1-propyl-1H-pyrazol-4-yl)pyridin-4-yl)oxy)pyridin-2-yl)-2-oxopyrrolidine-1-carboxamide | 449 |
| 15 | | N-(5-((2-(1-cyclopropyl-1H-pyrazol-4-yl)pyridin-4-yl)oxy)-6-methylpyridin-2-yl)-3,3-dimethyl-2-oxopyrrolidine-1-carboxamide | 447 |
| 16 | | N-(5-((2-(1-(2-hydroxy-2-methylpropyl)-1H-pyrazol-4-yl)pyridin-4-yl)oxy)-6-methylpyridin-2-yl)-3,3-dimethyl-2-oxopyrrolidine-1-carboxamide | 479 |

-continued

| Example No. | Structural formula | English name | MS m/z (ESI): [M + H]+ |
|---|---|---|---|
| 17 | | 3,3-dimethyl-N-(6-methyl-5-((2-(1-(1-methylpyrrolidin-3-yl)-1H-pyrazol-4-yl)-2-oxopyrrolidine-1-carboxamide | 490 |
| 18 | | 3,3-dimethyl-N-(6-methyl-5-((2-(1-(oxetan-3-yl)-1H-pyrazol-4-yl)pyridin-4-yl)oxy)pyridin-2-yl)-2-oxopyrrolidine-1-carboxamide | 463 |
| 19 | | 3,3-dimethyl-N-(6-methyl-5-((2-(1-methyl-1H-imidazol-4-yl)pyridin-4-yl)oxy)pyridin-2-yl)-2-oxopyrrolidine-1-carboxamide | 421 |
| 20 | | 3,3-dimethyl-N-(6-methyl-5-((2-(4-methyl-1H-imidazol-1-yl)pyridin-4-yl)oxy)pyridin-2-yl)-2-oxopyrrolidine-1-carboxamide | 421 |
| 21 | | 3,3-dimethyl-N-(6-methyl-5-((2-(1-methyl-1H-pyrazol-4-yl)pyridin-4-yl)methyl)pyridin-2-yl)-2-oxopyrrolidine-1-carboxamide | 419 |
| 22 | | 3,3-dimethyl-N-(6-methyl-5-((2-(1-methyl-1H-pyrazol-4-yl)pyrimidin-4-yl)oxy)pyridin-2-yl)-2-oxopyrrolidine-1-carboxamide | 422 |
| 23 | | N-(5-((2-acetylamidopyridin-4-yl)oxy)-6-methylpyridin-2-yl)-3,3-dimethyl-2-oxopyrrolidine-1-carboxamide | 398 |

-continued

| Example No. | Structural formula | English name | MS m/z (ESI): [M + H]+ |
|---|---|---|---|
| 24 | | N-(4-((6-(3,3-dimethyl-2-oxopyrrolidine-1-carboxamido)-2-methylpyridin-3-yl)oxy)pyridin-2-yl)-4-methylpiperazine-1-carboxamide | 482 |
| 25 | | N-(4-((6-(3,3-dimethyl-2-oxopyrrolidine-1-carboxamido)-2-methylpyridin-3-yl)oxy)pyridin-2-yl)-1-methylpiperidine-4-carboxamide | 481 |
| 26 | | N-(5-((2-(cyclopropanecarboxamido)pyridin-4-yl)oxy)-6-methylpyridin-2-yl)-3,3-dimethyl-2-oxopyrrolidine-1-carboxamide | 424 |
| 27 | | 4-((6-(3,3-dimethyl-2-oxopyrrolidine-1-carboxamido)-2-methylpyridin-3-yl)oxy)-N-methylpicolinamide | 398 |
| 28 | | 3,3-dimethyl-N-(6-methyl-5-((2-(1-methyl-1H-pyrazol-4-yl)pyridin-4-yl)oxy)pyridin-2-yl)-2-oxopiperidine-1-carboxamide | 435 |
| 29 | | 2,2-dimethyl-N-(6-methyl-5-((2-(1-methyl-1H-pyrazol-4-yl)pyridin-4-yl)oxy)pyridin-2-yl)-3-oxomorpholine-4-carboxamide | 437 |

| Example No. | Structural formula | English name | MS m/z (ESI): [M + H]+ |
|---|---|---|---|
| 30 | | N-(6-methyl-5-((2-(1-methyl-1H-pyrazol-4-yl)pyridin-4-yl)oxy)pyridin-2-yl)-2-oxo-3,3-dipropylpyrrolidine-1-carboxamide | 477 |
| 31 | | N-(6-methyl-5-((2-(1-methyl-1H-pyrazol-4-yl)pyridin-4-yl)oxy)pyridin-2-yl)-1-oxo-2-azaspiro[4.4]nonane-2-carboxamide | 447 |
| 32 | | 3-methyl-N-(6-methyl-5-((2-(1-methyl-1H-pyrazol-4-yl)pyridin-4-yl)oxy)pyridin-2-yl)-2-oxopyrrolidine-1-carboxamide | 407 |
| 33 | | 3-ethyl-3-methyl-N-(6-methyl-5-((2-(1-methyl-1H-pyrazol-4-yl)pyridin-4-yl)oxy)pyridin-2-yl)-2-oxopyrrolidine-1-carboxamide | 435 |
| 34 | | 3,3-diethyl-N-(6-methyl-5-((2-(1-methyl-1H-pyrazol-4-yl)pyridin-4-yl)oxy)pyridin-2-yl)-2-oxopyrrolidine-1-carboxamide | 449 |
| 35 | | N-(6-methyl-5-((2-(1-methyl-1H-pyrazol-4-yl)pyridin-4-yl)oxy)pyridin-2-yl)-5-oxo-6-azaspiro[3.4]octane-6-carboxamide | 433 |
| 36 | | 3-(benzyloxy)-3-methyl-N-(6-methyl-5-((2-(1-methyl-1H-pyrazol-4-yl)pyridin-4-yl)oxy)pyridin-2-yl)-2-oxopyrrolidine-1-carboxamide | 513 |

| Example No. | Structural formula | English name | MS m/z (ESI): [M + H]+ |
|---|---|---|---|
| 37 | | 3-(2-methoxyethyl)-3-methyl-N-(6-methyl-5-((2-(1-methyl-1H-pyrazol-4-yl)pyridin-4-yl)oxy)pyridin-2-yl)-2-oxopyrrolidine-1-carboxamide | 465 |
| 38 | | N-(6-methyl-5-((2-(1-methyl-1H-pyrazol-4-yl)pyridin-4-yl)oxy)pyridin-2-yl)-2-oxopyrrolidine-1-carboxamide | 393 |
| 39 | | 3,3-dimethyl-N-(6-methyl-5-((2-(1-(methyl-d$_3$)-1H-pyrazol-4-yl)pyridin-4-yl)oxy)pyridin-2-yl)-2-oxopiperidine-1-carboxamide | 438 |
| 40 | | N-(6-methyl-5-((2-(1-methyl-d$_3$)-1H-pyrazol-4-yl)pyridin-4-yl)oxy)pyridin-2-yl)-5-oxo-6-azaspiro[3.4]octane-6-carboxamide | 436 |

$^1$H NMR Data of Examples 2-8 and 11-40 Listed as Follows:

| Example No. | $^1$H NMR (400 MHz) |
|---|---|
| 2 | (DMSO-d$_6$) δ 11.08 (s, 1H), 8.39 (d, J = 5.6 Hz, 1H), 8.29 (d, J = 2.9 Hz, 1H), 8.27 (s, 1H), 8.10 (d, J = 9.1 Hz, 1H), 7.98 (s, 1H), 7.77 (dd, J = 9.1, 2.9 Hz, 1H), 7.25 (d, J = 2.4 Hz, 1H), 6.71 (dd, J = 5.7, 2.4 Hz, 1H), 3.86 (s, 3H), 3.78 (t, J = 7.0 Hz, 2H), 1.91 (t, J = 7.0 Hz, 2H), 1.19 (s, 6H). |
| 3 | (DMSO-d$_6$) δ 11.03 (s, 1H), 8.37 (d, J = 5.7 Hz, 1H), 8.27 (s, 1H), 7.97 (s, 1H), 7.93 (d, J = 8.8 Hz, 1H), 7.66 (d, J = 8.8 Hz, 1H), 7.20 (d, J = 2.4 Hz, 1H), 6.61 (dd, J = 5.8, 2.4 Hz, 1H), 3.86 (s, 3H), 3.78 (t, J = 7.0 Hz, 2H), 2.60 (q, J = 7.5 Hz, 2H), 1.91 (t, J = 7.0 Hz, 2H), 1.20 (s, 6H), 1.14 (t, J = 7.5 Hz, 3H). |
| 4 | (DMSO-d$_6$) δ 11.03 (s, 1H), 8.59 (d, J = 5.7 Hz, 1H), 8.54 (d, J = 5.3 Hz, 1H), 7.98-7.88 (m, 2H), 7.82 (d, J = 5.3 Hz, 1H), 7.75-7.64 (m, 2H), 6.89 (dd, J = 5.7, 2.5 Hz, 1H), 3.78 (t, J = 7.0 Hz, 2H), 2.54 (s, 3H), 2.30 (s, 3H), 1.91 (t, J = 7.0 Hz, 2H), 1.19 (s, 6H). |
| 5 | (DMSO-d$_6$) δ 11.02 (s, 1H), 8.40 (d, J = 5.7 Hz, 1H), 8.34 (s, 1H), 7.93 (d, J = 8.8 Hz, 1H), 7.69 (d, J = 8.8 Hz, 1H), 7.58 (d, J = 2.4 Hz, 1H), 6.72 (dd, J = 5.8, 2.4 Hz, 1H), 3.78 (t, J = 7.1 Hz, 2H), 2.67 (s, 3H), 2.28 (s, 3H), 1.91 (t, J = 7.0 Hz, 2H), 1.19 (s, 6H). |
| 6 | (DMSO-d$_6$) δ 11.01 (s, 1H), 8.37 (d, J = 5.7 Hz, 1H), 8.32 (s, 1H), 7.99 (d, J = 0.7 Hz, 1H), 7.93 (d, J = 8.8 Hz, 1H), 7.66 (d, J = 8.8 Hz, 1H), 7.20 (d, J = 2.4 Hz, 1H), 6.62 (dd, J = 5.7, 2.5 Hz, 1H), 4.15 (q, J = 7.3 Hz, 2H), 3.78 (dd, J = 8.0, 6.1 Hz, 2H), 2.28 (s, 3H), 1.91 (t, J = 7.0 Hz, 2H), 1.39 (t, J = 7.3 Hz, 3H), 1.19 (s, 6H). |
| 7 | (DMSO-d$_6$) δ 11.01 (s, 1H), 8.37 (d, J = 5.7 Hz, 1H), 8.28 (d, J = 0.7 Hz, 1H), 8.00 (d, J = 0.8 Hz, 1H), 7.93 (d, J = 8.8 Hz, 1H), 7.67 (d, J = 8.8 Hz, 1H), 7.21 (d, J = 2.4 Hz, 1H), 6.61 (dd, J = 5.7, 2.4 Hz, 1H), 4.27 (t, J = 5.3 Hz, 2H), 3.78 (t, J = 7.0 Hz, 2H), 3.70 (t, J = 5.3 Hz, 2H), 3.23 (s, 3H), 2.28 (s, 3H), 1.91 (t, J = 7.0 Hz, 2H), 1.19 (s, 6H). |
| 8 | (DMSO-d$_6$) δ 11.01 (s, 1H), 8.37 (d, J = 5.7 Hz, 1H), 8.31 (s, 1H), 7.98 (d, J = 0.8 Hz, 1H), 7.93 (d, J = 8.8 Hz, 1H), 7.67 (d, J = 8.8 Hz, 1H), 7.17 (d, J = 2.4 Hz, 1H), 6.62 (dd, J = 5.7, 2.4 Hz, 1H), 4.24 (t, J = 6.5 Hz, 2H), 3.78 (t, J = 7.0 Hz, 2H), 3.53 (t, J = 4.6 Hz, 4H), 2.72 (t, J = 6.5 Hz, 2H), 2.41 (t, J = 4.2 Hz, 4H), 2.28 (s, 3H), 1.91 (t, J = 7.0 Hz, 2H), 1.19 (s, 6H). |
| 11 | (Chloroform-d) δ 11.09 (s, 1H), 8.40 (d, J = 5.9 Hz, 1H), 8.11 (s, 1H), 8.00 (d, J = 8.8 Hz, 1H), 7.88 (s, 1H), 7.38 (d, |

| Example No. | ¹H NMR (400 MHz) |
|---|---|
|  | J = 8.8 Hz, 1H), 6.93 (d, J = 2.3 Hz, 1H), 6.61 (dd, J = 5.9, 2.2 Hz, 1H), 3.87 (t, J = 8.0, 2H), 2.34 (s, 3H), 1.98-1.93 (m, 2H) 1.28 (s, 6H). |
| 12 | (DMSO-$d_6$) δ 11.01 (s, 1H), 8.41-8.35 (m, 2H), 8.03 (d, J = 0.7 Hz, 1H), 7.93 (d, J = 8.8 Hz, 1H), 7.66 (d, J = 8.8 Hz, 1H), 7.25 (d, J = 2.4 Hz, 1H), 6.61 (dd, J = 5.7, 2.5 Hz, 1H), 5.10-5.00 (m, 1H), 4.03-3.95 (m, 2H), 3.91 (dd, J = 9.4, 3.7 Hz, 1H), 3.86-3.75 (m, 3H), 2.28 (s, 4H), 1.91 (t, J = 7.0 Hz, 2H), 1.19 (s, 6H). |
| 13 | (DMSO-$d_6$) δ 11.01 (s, 1H); 8.37 (d, J = 5.6 Hz, 1H), 8.34 (s, 1H), 7.98 (s, 1H), 7.93 (d, J = 8.4 Hz, 1H), 7.65 (d, J = 8.8 Hz, 1H), 7.22 (d, J = 2.4 Hz 1H), 6.61-6.59 (m, 1H), 4.54-4.79 (m, 1H), 3.78 (t, J = 6.8 Hz, 2H), 2.28 (s, 3H), 1.91 (t, J = 7.2 Hz, 2H), 1.43 (d, J = 6.8 Hz, 6H), 1.19 (s, 6H). |
| 14 | (DMSO-$d_6$) δ 11.01 (s, 1H), 8.36 (d, J = 5.6 Hz, 1H), 8.30 (s, 1H), 7.98 (s, 1H), 7.93 (d, J = 8.4 Hz, 1H), 7.65 (d, J = 8.8 Hz, 1H), 7.19 (d, J = 2.4 Hz, 1H), 6.62-6.60 (m, 1H), 4.07 (t, J = 5.6 Hz, 2H), 3.78 (t, J = 5.6 Hz, 2H), 2.28 (s, 3H), 1.91 (t, J = 7.2 Hz, 2H), 1.84-1.75 (m, 2H), 1.19 (s, 6H), 0.82 (t, J = 7.06 Hz, 3H). |
| 15 | (DMSO-$d_6$): δ 11.01 (s, 1H), 8.45-8.30 (m, 2H), 7.97 (s, 1H), 7.92 (d, J = 8.4 Hz, 1H), 7.65 (d, J = 8.8 Hz, 1H), 7.22 (d, J = 2.4 Hz, 1H), 6.62-6.60 (m, 1H), 3.79-3.72 (m, 3H), 2.28 (s, 3H), 1.91 (t, J = 7.2 Hz, 2H), 1.19 (s, 6H) 1.09-1.05 (m, 2H), 0.99-0.96 m, 2H). |
| 16 | (DMSO-$d_6$): δ 11.01 (s, 1H), 8.37 (d, J = 6.0 Hz, 1H), 8.22 (s, 1H), 7.99 (s, 1H), 7.92 (d, J = 8.4 Hz, 1H), 7.66 (d, J = 8.8 Hz, 1H), 7.21 (d, J = 2.4 Hz, 1H), 6.62-6.60 (m, 1H), 4.72 (s, 1H), 4.03 (s, 2H), 3.78 (t, J = 7.2 Hz, 2H), 2.28 (s, 3H), 1.91 (t, J = 7.2 Hz, 2H), 1.19 (s, 6H), 1.07 (s, 6H). |
| 17 | (Methanol-$d_4$) δ 8.34 (d, J = 5.9 Hz, 1H), 8.27 (s, 1H), 8.05-7.98 (m, 2H), 7.55 (d, J = 8.8 Hz, 1H), 7.18 (d, J = 2.3 Hz, 1H), 6.69 (dd, J = 5.8, 2.4 Hz, 1H), 4.98 (s, 1H), 3.84 (t, J = 7.0 Hz, 2H), 3.05 (t, J = 8.9 Hz, 1H), 2.95-2.87 (m, 2H), 2.75-2.65 (m, 1H), 2.55-2.44 (m, 1H), 2.44-2.39 (m, 3H), 2.33 (s, 3H), 2.28-2.22 (m, 1H), 1.98 (t, J = 7.1 Hz, 2H), 1.26 (s, 6H). |
| 18 | (Chloroform-d) δ 11.08 (s, 1H), 8.41 (d, J = 5.8 Hz, 1H), 8.14 (s, 1H), 8.05-7.95 (m, 2H), 7.38 (d, J = 8.8 Hz, 1H), 6.93 (d, J = 2.4 Hz, 1H), 6.59 (dd, J = 5.8, 2.5 Hz, 1H), 5.49 (p, J = 6.9 Hz, 1H), 5.08 (dd, J = 6.9, 2.1 Hz, 4H) 3.87 (t, J = 7.1 Hz, 2H), 2.34 (s, 3H), 1.95 (t, J = 7.0 Hz, 2H), 1.28 (s, 6H). |
| 19 | (DMSO-$d_6$) δ 11.03 (s, 1H), 8.38 (d, J = 5.7 Hz, 1H), 7.95 (d, J = 8.8 Hz, 1H), 7.75-7.65 (m, 2H), 7.61 (s, 1H), 7.17 (d, J = 2.6 Hz, 1H), 6.77 (dd, J = 5.7, 2.6 Hz, 1H), 3.78 (t, J = 7.0 Hz, 2H), 3.69 (s, 3H), 2.26 (s, 3H), 1.91 (t, J = 7.0 Hz, 2H), 1.19 (d, J = 2.7 Hz, 6H). |
| 20 | (DMSO-$d_6$) δ 11.02 (s, 1H), 8.41 (s, 1H), 8.34 (d, J = 5.7 Hz, 1H), 7.94 (d, J = 8.8 Hz, 1H), 7.70 (d, J = 8.9 Hz, 1H), 7.65 (s, 1H), 7.35 (d, J = 2.2 Hz, 1H), 6.76 (dd, J = 5.9, 2.2 Hz, 1H), 3.78 (t, J = 7.0 Hz, 2H), 2.29 (s, 3H), 2.15 (s, 3H), 1.91 (t, J = 7.0 Hz, 2H), 1.19 (s, 6H). |
| 21 | (Chloroform-d) δ 11.02 (s, 1H), 8.48 (d, J = 5.7 Hz, 1H), 7.95-7.85 (m 2H), 7.43 (d, J = 8.3 Hz, 1H), 7.38 (s, 1H), 7.07 (s, 1H), 4.07 (s, 2H), 3.99 (s, 3H), 3.86 (t, J = 7.1 Hz, 2H), 2.36 (s, 3H), 1.94 (t, J = 7.0 Hz, 2H), 1.27 (s, 6H). |
| 22 | (DMSO-$d_6$): 11.01 (s, 1H), 8.63 (d, J = 6.0 Hz, 1H), 8.09 (s, 1H), 7.94 (d, J = 8.8 Hz, 1H), 7.78 (s, 1H), 7.73 (d, J = 6.0 Hz, 1H), 6.89 (d, J = 5.6 Hz, 1H), 3.85 (s, 3H), 3.78 (t, J = 7.2 Hz, 2H), 2.25 (s, 3H), 1.91 (t, J = 7.2 Hz, 2H), 1.19 (s, 6H). |
| 23 | (DMSO-$d_6$) δ 11.01 (s, 1H), 10.57 (s, 1H), 8.19 (d, J = 5.8 Hz, 1H), 7.92 (d, J = 8.8 Hz, 1H), 7.66 (d, J = 8.8 Hz, 1H), 7.59 (d, J = 2.4 Hz, 1H), 6.64 (dd, J = 5.7, 2.4 Hz, 1H), 3.77 (t, J = 8.0 Hz, 2H), 2.24 (s, 3H), 2.04 (s, 3H), 1.91 (t, J = 8.0 Hz, 2H), 1.19 (s, 6H). |
| 24 | (DMSO-$d_6$) δ 11.01 (s, 1H), 9.25 (s, 1H), 8.12 (d, J = 5.8 Hz, 1H), 7.92 (d, J = 8.7 Hz, 1H), 7.65 (d, J = 8.8 Hz, 1H), 7.29 (d, J = 2.4 Hz, 1H), 6.57 (dd, J = 5.7, 2.3 Hz, 1H), 3.77 (t, J = 7.0 Hz, 2H), 3.40 (d, J = 5.0 Hz, 4H), 2.40-2.30 (m, 7H), 2.16 (s, 3H), 1.90 (t, J = 7.0 Hz, 2H), 1.19 (s, 6H). |
| 25 | (DMSO-$d_6$) δ 11.02 (s, 1H), 10.52 (s, 1H), 8.19 (d, J = 5.8 Hz, 1H), 7.93 (d, J = 8.8 Hz, 1H), 7.66 (d, J = 8.8 Hz, 1H), 7.58 (d, J = 2.4 Hz, 1H), 6.68 (dd, J = 5.7, 2.4 Hz, 1H), 3.78 (t, J = 7.0 Hz, 2H), 2.78-2.70 (m, 2H), 2.42-2.38 (m, 1H), 2.24 (s, 3H), 2.12 (s, 3H), 1.91 (t, J = 7.0 Hz, 2H), 1.82-1.77 (m, 2H), 1.70-1.65 (m, 2H), 1.59-1.52 (m, 2H), 1.19 (s, 6H). |
| 26 | (DMSO-$d_6$) δ 11.01 (s, 1H), 10.87 (s, 1H), 8.20 (d, J = 5.7 Hz, 1H), 7.92 (d, J = 8.8 Hz, 1H), 7.66 (d, J = 8.8 Hz, 1H), 7.56 (d, J = 2.4 Hz, 1H), 6.68 (dd, J = 5.7, 2.4 Hz, 1H), 3.77 (t, J = 7.0 Hz, 2H), 2.23 (s, 3H), 2.00-1.93 (m, 1H), 1.90 (t, J = 7.0 Hz, 2H), 1.19 (s, 6H), 0.80-0.72 (m, 4H). |
| 27 | (DMSO-$d_6$) δ 11.03 (s, 1H), 8.80 (d, J = 5.3 Hz, 1H), 8.53 (d, J = 5.6 Hz, 1H), 7.95 (d, J = 8.8 Hz, 1H), 7.72 (d, J = 8.8 Hz, 1H), 7.35 (d, J = 2.7 Hz, 1H), 7.15 (dd, J = 5.6, 2.6 Hz, 1H), 3.78 (t, J = 7.0 Hz, 2H), 2.79 (d, J = 4.8 Hz, 3H), 2.25 (s, 3H), 1.91 (t, J = 7.0 Hz, 2H), 1.19 (s, 6H). |
| 28 | (DMSO-$d_6$) δ 12.18 (s, 1H), 8.37 (d, J = 5.7 Hz, 1H), 8.27 (s, 1H), 7.97 (s, 1H), 7.94 (d, J = 8.8 Hz, 1H), 7.65 (d, J = 8.8 Hz, 1H), 7.18 (d, J = 2.5 Hz, 1H), 6.61 (dd, J = 5.7, 2.5 Hz, 1H), 3.86 (s, 3H), 3.76 (t, J = 6.0 Hz, 2H), 2.27 (s, 3H), 1.90-1.80 (m, 2H), 1.75-1.66 (m, 2H), 1.26 (s, 6H). |
| 29 | (DMSO-$d_6$) δ 11.86 (s, 1H), 8.37 (d, J = 5.7 Hz, H), 8.27 (s, 1H), 7.97 (s, 1H), 7.94 (d, J = 8.8 Hz, 1H), 7.67 (d, J = 8.8 Hz, 1H), 7.19 (d, J = 2.4 Hz, 1H), 6.62 (dd, J = 5.7, 2.4 Hz, 1H), 3.94 (dd, J = 6.2, 3.8 Hz, 2H), 3.86 (s, 3H), 3.78 (dd, J = 6.2, 3.8 Hz, 2H), 2.28 (s, 3H), 1.46 (s, 6H). |
| 30 | (DMSO-$d_6$) δ 11.09 (s, 1H), 8.37 (d, J = 5.7 Hz, 1H), 8.26 (s, 1H), 7.97 (s, 1H), 7.93 (d, J = 8.8 Hz, 1H), 7.66 (d, J = 8.8 Hz, 1H), 7.17 (d, J = 2.4 Hz, 1H), 6.62 (dd, J = 5.5, 2.4 Hz, 1H), 3.86 (s, 3H), 3.75 (t, J = 7.4 Hz, 2H), 2.28 (s, 3H), 1.94 (t, J = 7.3 Hz, 2H), 1.60-1.16 (m, 8H), 0.89 (t, J = 7.1 Hz, 6H). |
| 31 | (DMSO-$d_6$) δ 11.04 (s, 1H), 8.37 (d, J = 5.7 Hz, 1H), 8.26 (s, 1H), 7.97 (s, 1H), 7.93 (d, J = 8.8 Hz, 1H), 7.66 (d, J = 8.8 Hz, 1H), 7.18 (d, J = 2.4 Hz, 1H), 6.61 (dd, J = 5.7, 2.4 Hz, 1H), 3.86 (s, 3H), 3.76 (t, J = 6.9 Hz, 2H), 2.28 (s, 3H), 1.96 (t, J = 6.9 Hz, 2H), 1.90-1.70 (m, 8H). |
| 32 | (DMSO-$d_6$) δ 11.01 (s, 1H), 8.37 (d, J = 5.7 Hz, 1H), 8.27 (s, 1H), 7.97 (s, 1H), 7.93 (d, J = 8.8 Hz, 1H), 7.66 (d, J = 8.8 Hz, 1H), 7.19 (d, J = 2.4 Hz, 1H), 6.62 (dd, J = 5.7, 2.4 Hz, 1H), 3.86 (s, 4H), 3.68-3.59 (m, 1H), 2.87 (q, J = 8.3 Hz, 1H), 2.28 (s, 4H), 1.72-1.60 (m, 1H), 1.18 (d, J = 7.1 Hz, 3H). |
| 33 | (DMSO-$d_6$) δ 11.05 (s, 1H), 8.37 (d, J = 5.7 Hz, 1H), 8.26 (s, 1H), 7.97 (s, 1H), 7.93 (d, J = 8.8 Hz, 1H), 7.66 (d, J = 8.8 Hz, 1H), 7.18 (d, J = 2.4 Hz, 1H), 6.62 (dd, J = 5.7, 2.4 Hz, 1H), 3.86 (s, 3H), 3.77 (t, J = 7.2 Hz, 2H), 2.28 (s, 3H), 2.00-1.85 (m, 1H), 1.83-1.72 (m, 1H), 1.60-1.50 (m, 2H), 1.17 (s, 3H), 0.88 (t, J = 7.4 Hz, 3H). |
| 34 | (DMSO-$d_6$) δ 11.11 (s, 1H), 8.37 (d, J = 5.7 Hz, 1H), 8.27 (s, 1H), 7.97 (s, 1H), 7.93 (d, J = 8.8 Hz, 1H), 7.67 (d, J = 8.8 Hz, 1H), 7.17 (d, J = 2.4 Hz, 1H), 6.62 (dd, J = 5.7, 2.4 Hz, 1H), 3.86 (s, 3H), 3.76 (t, J = 7.3 Hz, 2H), 2.28 (s, 3H), 1.92 (t, J = 7.3 Hz, 2H), 1.67-1.52 (m, 4H), 0.86 (t, J = 7.4 Hz, 6H). |
| 35 | (DMSO-$d_6$) δ 11.04 (s, 1H), 8.37 (d, J = 5.7 Hz, 1H), 8.27 (s, 1H), 7.97 (s, 1H), 7.92 (d, J = 8.8 Hz, 1H), 7.66 (d, J = 8.8 Hz, 1H), 7.19 (d, J = 2.4 Hz, 1H), 6.62 (dd, J = 5.7, 2.4 Hz, 1H), 3.86 (s, 3H), 3.71 (t, J = 6.9 Hz, 2H), 2.41-2.32 (m, 2H), 2.28 (s, 3H), 2.18 (t, J = 6.9 Hz, 2H), 2.05-1.80 (m, 4H). |
| 36 | (Chloroform-d) δ 10.96 (s, 1H), 8.40 (d, J = 5.9 Hz, 1H), 8.01 (d, J = 8.9 Hz, 1H), 7.88 (s, 1H), 7.43-7.27 (m, 7H), 6.94 (d, J = 2.2 Hz, 1H), 6.60 (dd, J = 5.7, 2.0 Hz, 1H), 4.64 (d, J = 1.6 Hz, 2H), 4.05-3.90 (m, 4H), 3.85-3.80 (m, 1H), 2.41-2.35 (m, 1H) 2.35 (s, 3H), 2.10-2.05 (m, 1H), 1.58 (s, 3H). |
| 37 | (DMSO-$d_6$) δ 11.03 (s, 1H), 8.37 (d, J = 5.7 Hz, 1H), 8.26 (s, 1H), 7.97 (s, 1H), 7.93 (d, J = 8.8 Hz, 1H), 7.66 (d, J = 8.8 Hz, 1H), 7.18 (d, J = 2.4 Hz, 1H), 6.62 (dd, J = 5.7, 2.4 Hz, 1H), 3.86 (s, 3H), 3.76 (t, J = 7.2 Hz, 2H), 3.46-3.42 (m, 2H), 3.21 (s, 3H), 2.28 (s, 3H), 2.12-2.09 (m, 1H), 1.88-1.83 (m, 2H) 1.77-1.70 (m, 1H), 1.19 (s, 3H). |
| 38 | (DMSO-$d_6$) δ 11.02 (s, 1H), 8.37 (d, J = 5.7 Hz, 1H), 8.27 (s, 1H), 7.97 (d, J = 0.7 Hz, 1H), 7.96-7.91 (m, 1H), 7.66 (d, J = 8.8 Hz, 1H), 7.19 (d, J = 2.4 Hz, 1H), 6.62 (dd, J = 5.7, 2.5 Hz, 1H), 3.86 (s, 3H), 3.82 (t, J = 7.2 Hz, 2H), 2.69 (t, J = 8.1 Hz, 2H), 2.28 (s, 3H), 2.04-1.96 (m, 2H). |
| 39 | (Chloroform-d) δ 12.23 (s, 1H), 8.39 (d, J = 5.8 Hz, 1H), 8.00 (d, J = 8.8 Hz, 1H), 7.92 (s, 1H), 7.87 (d, J = 0.8 Hz, 1H), 7.37 (d, J = 8.8 Hz, 1H), 6.90 (d, J = 2.4 Hz, 1H), 6.57 |

| Example No. | ¹H NMR (400 MHz) |
|---|---|
|  | (dd, J = 5.8, 2.4 Hz, 1H), 3.87 (t, J = 6.1 Hz, 2H), 2.33 (s, 3H), 1.97-1.90 (m, 2H), 1.79-1.75 (m, 2H), 1.34 (s, 6H). |
| 40 | (Chloroform-d) δ 11.12 (s, 1H), 8.40 (d, J = 5.9 Hz, 1H), 7.99 (d, J = 8.9 Hz, 1H), 7.88 (s, 1H), 7.38 (d, J = 8.9 Hz, 1H), 7.31-7.27 (m, 1H), 6.95-6.91 (m, 1H), 6.60 (d, J = 7.1 Hz, 1H), 3.81 (t, J = 7.0 Hz, 2H), 2.57-2.47 (m, 2H), 2.34 (s, 3H), 2.21 (t, J = 6.9 Hz, 2H), 2.16-2.00 (m, 4H). |

Example 9: Preparation of N-(5-((2-(1H-pyrazol-4-yl)pyridin-4-yl)oxy)-6-methylpyridin-2-yl)-3,3-dimethyl-2-oxopyrrolidine-1-carboxamide

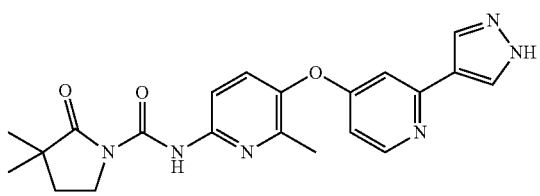 [SMILES: Cc1nc(NC(=O)N2CCC(C)(C)C2=O)ccc1Oc1ccnc(-c2cn[nH]c2)c1]

Step 1: Preparation of tert-butyl 4-(4-((6-(3,3-dimethyl-2-oxopyrrolidine-1-carboxamido)-2-methylpyridin-3-yl)oxy)pyridin-2-yl)-1H-pyrazole-1-carboxylate

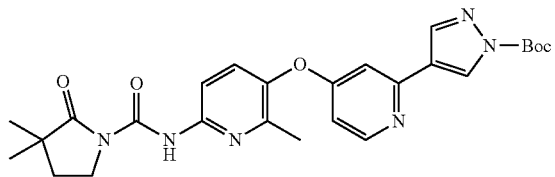 [SMILES: Cc1nc(NC(=O)N2CCC(C)(C)C2=O)ccc1Oc1ccnc(-c2cnn(C(=O)OC(C)(C)C)c2)c1]

Triphosgene (88 mg, 0.296 mmol) was dissolved in dichloromethane (2 mL), and the solution of 3,3-dimethylpyrrolidin-2-one (100 mg, 0.885 mmol) and pyridine (209 mg, 2.655 mmol) in dichloromethane (2 mL) was added under an ice bath. The reaction solution was stirred for 0.5 hr under an ice bath. The above mixture solution was then added to the solution of tert-butyl 4-(4-((6-amino-2-methylpyridin-3-yl)oxy)pyridin-2-yl)-1H-pyrazole-1-carboxylate (90 mg, 0.245 mmol) and pyridine (20 mg, 0.25 mmol) in dichloromethane (2 mL) under the ice bath. The reaction solution was stirred at room temperature for 1 hr, then poured into water (30 mL), and then extracted with dichloromethane (20 mL*2). The organic phases were combined and washed once with brine (40 mL), dried over sodium sulfate and filtered. The filtrate is concentrated to obtain a crude product of tert-butyl 4-(4-((6-(3,3-dimethyl-2-oxopyrrolidine-1-carboxamido)-2-methylpyridin-3-yl)oxy)pyridin-2-yl)-1H-pyrazole-1-carboxylate (50 mg, yield 40%). MS m/z (ESI): 507 [M+H]⁺.

Step 2: Preparation of N-(5-((2-(1H-pyrazol-4-yl)pyridin-4-yl)oxy)-6-methylpyridin-2-yl)-3,3-dimethyl-2-oxopyrrolidine-1-carboxamide

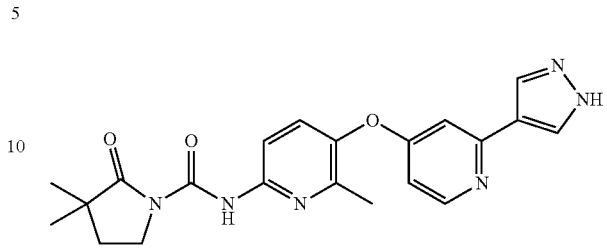

Tert-butyl 4-(4-((6-(3,3-dimethyl-2-oxopyrrolidine-1-carboxamido)-2-methylpyridin-3-yl) oxy)pyridin-2-yl)-1H-pyrazole-1-carboxylate (50 mg, 0.1 mmol) was dissolved in 4 M of hydrochloric acid/ethyl acetate solution (10 mL). The reaction solution was stirred at room temperature for 3 hrs. The solution was filtered and then separated by reversed phase column chromatography (eluent: 0.5% ammonium bicarbonate aqueous solution ~0.5% ammonium bicarbonate aqueous solution/acetonitrile (50:50)] to obtain N-(5-((2-(1H-pyrazol-4-yl)pyridin-4-yl)oxy)-6-methylpyridin-2-yl)-3,3-dimethyl-2-oxopyrrolidine-1-carboxamide (9.3 mg, yield 23%). MS m/z. (ESI): 407 [M+H]⁺.
¹H NMR (400 MHz, DMSO-d₆) δ 13.06 (s, 1H), 11.01 (s, 1H), 8.37 (d, J=5.7 Hz, 1H), 8.33 (s, 1H), 8.04 (s, 1H), 7.93 (d, J=8.8 Hz, 1H), 7.66 (d, J=8.8 Hz, 1H), 7.29 (d, J=2.4 Hz, 1H), 6.58 (dd, J=5.7, 2.4 Hz, 1H), 3.78 (t, J=7.0 Hz, 2H), 2.28 (s, 3H), 1.91 (t, J=7.0 Hz, 2H), 1.19 (s, 6H).

Example 10: Preparation of N-(5-((2-(1-(2-hydroxyethyl)-1H-pyrazol-4-yl)pyridin-4-yl) oxy)-6-methylpyridin-2-yl)-3,3-dimethyl-2-oxopyrrolidine-1-carboxamide

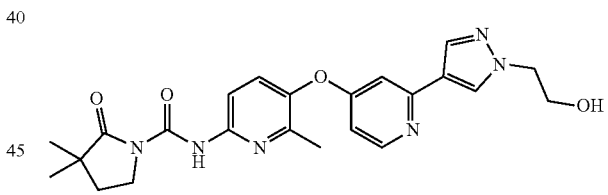

Step 1: Preparation of N-(5-((2-(1-(2-((tert-butyldimethylsilyl)oxy)ethyl)-1H-pyrazol-4-yl)pyridin-4-yl) oxy)-6-methylpyridin-2-yl)-3,3-dimethyl-2-oxopyrrolidine-1-carboxamide

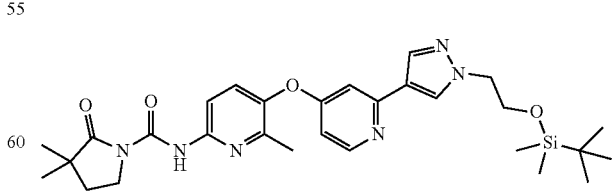

Triphosgene (2.07 g, 7 mmol) was dissolved in dichloromethane (20 mL), and the solution of 3,3-dimethylpyrrolidin-2-one (2.4 g, 21 mmol) and pyridine (4.98 g, 63 mmol) in dichloromethane (20 mL) was added under an ice bath.

The reaction solution was stirred for 0.5 hr under an ice bath. The above solution was then added to the solution of 5-((2-(1-(2-((tert-butyldimethylsilyl)oxy)ethyl)-1H-pyrazol-4-yl)pyridin-4-yl)oxy)-6-methylpyridin-2-amine (3.0 g, 7 mmol) and pyridine (560 mg, 7 mmol) in dichloromethane solution (20 mL) under the ice bath. The reaction solution was stirred at room temperature for 1 hr, then poured into water (200 mL), and then extracted twice with dichloromethane (100 mL*2). The organic phases were combined and washed once with brine (100 mL), dried over sodium sulfate and filtered, and then separated by reversed phase column chromatography (eluent: 0.5% ammonium bicarbonate aqueous solution ~0.5% ammonium bicarbonate aqueous solutionlacetonitrile (50:50)] to obtain N-(5-((2-(1-(2-((tert-butyldimethylsilyl)oxy)ethyl)-1H-pyrazol-4-yl)pyridin-4-yl)oxy)-6-methylpyridin-2-yl)-3,3-dimethyl-2-oxopyrrolidine-1-carboxamide (1.0 g, yield 2.5%). MS m/z (ESI):565 [M+H]$^+$.

Step 2: Preparation of N-(5-((2-(1-(2-hydroxyethyl)-1H-pyrazol-4-yl)pyridin-4-yl)oxy)-6-methylpyridin-2-yl)-3,3-dimethyl-2-oxopyrrolidine-1-carboxamide

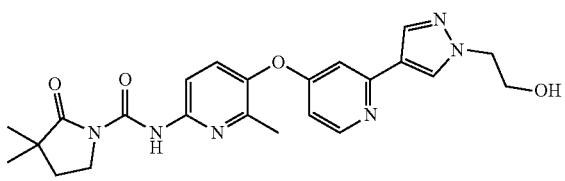 [SMILES: Cc1nc(NC(=O)N2CCC(C)(C)C2=O)ccc1Oc1ccnc(-c2cnn(CCO)c2)c1]

N-(5-((2-(1-(2-((tert-butyldimethylsilyl)oxy)ethyl)-1H-pyrazol-4-yl)pyridin-4-yl)oxy)-6-methylpyridin-2-yl)-3,3-dimethyl-2-oxopyrrolidine-1-carboxamide (1.0 g, 1.77 mmol) was dissolved in 4 M of hydrochloric acid/1,4-dioxane solution (15 mL). The reaction solution was stirred at room temperature for 2 hrs. The solution was filtered and separated by reversed phase column chromatography (eluent: 0.5% ammonium bicarbonate aqueous solution ~0.5% ammonium bicarbonate aqueous solution/acetonitrile (50:50)] to obtain N-(5-((2-(1-(2-hydroxyethyl)-1H-pyrazol-4-yl)pyridin-4-yl)oxy)-6-methylpyridin-2-yl)-3,3-dimethyl-2-oxopyrrolidine-1-carboxamide (377 mg, yield 47.3%). MS m/z (ESI): 451 [M+H]$^+$.

$^1$H NMR (400 MHz, DMSO-d$_6$) δ 11.01 (s, 1H), 8.37 (d, J=5.7 Hz, 1H), 8.28 (d, J=0.7 Hz, 1H), 8.00 (d, J=0.7 Hz, 1H), 7.93 (d, J=8.8 Hz, 1H), 7.66 (d, J=8.8 Hz, 1H), 7.20 (d, J=2.4 Hz, 1H), 6.61 (dd, J=5.7, 2.5 Hz, 1H), 4.15 (t, J=5.6 Hz, 2H), 3.85-3.70 (m, 4H), 2.28 (s, 3H), 1.91 (t, J=7.0 Hz, 2H), 1.19 (s, 6H).

Example 41: Preparation of 3-hydroxy-3-methyl-N-(6-methyl-5-((2-(1-methyl-1H-pyrazol-4-yl)pyridin-4-yl)oxy)pyridin-2-yl)-2-oxopyrrolidine-1-carboxamide

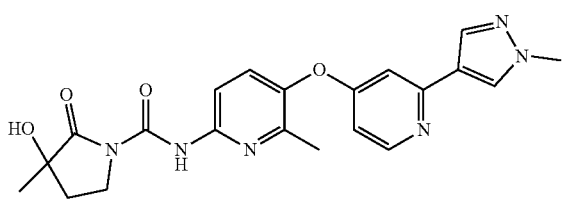

Palladium on carbon (50 mg) was added to the solution of 3-(benzyloxy)-3-methyl-N-(6-methyl-5-((2-(1-methyl-1H-pyrazol-4-yl)pyridin-4-yl)oxy)pyridin-2-yl)-2-oxopyrrolidine-1-carboxamide (80 mg, 0.15 mmol) in methanol (10 mL). The reaction solution was stirred at 50° C. under hydrogen atmosphere for 2 hrs. The solution was filtered, concentrated and separated by plate chromatography (dichloromethane/methanol=18:1) to obtain 3-hydroxy-3-methyl-N-(6-methyl-5-((2-(1-methyl-1H-pyrazol-4-yl)pyridin-4-yl)oxy)pyridin-2-yl)-2-oxopyrrolidine-1-carboxamide (10 mg, yield 15%). MS m/z (ESI): 423 [M+H]$^+$.

$^1$H NMR (400 MHz, DMSO-d$_6$) δ 10.93 (s, 1H), 8.37 (d, J=5.7 Hz, 1H), 8.27 (s, 1H), 8.01-7.85 (m, 2H), 7.67 (d, J=8.8 Hz, 1H), 7.19 (d, J=2.4 Hz, 1H), 6.62 (dd, J=5.7, 2.4 Hz, 1H), 5.89 (s, 1H), 3.86 (s, 3H), 3.83-3.76 (m, 1H), 3.67-3.61 (m, 1H), 2.29 (s, 3H), 2.09-1.98 (m, 2H), 1.34 (s, 3H).

Example 42: Preparation of 3,3-dimethyl-N-(6-methyl-5-((2-(methylamino)pyridin-4-yl)oxy)pyridin-2-yl)-2-oxopyrrolidine-1-carboxamide

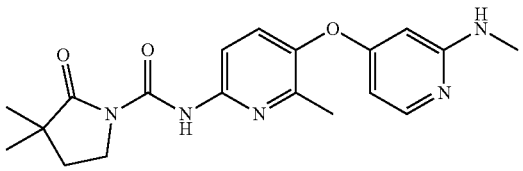

Step 1: Preparation of tert-butyl methyl(4-((2-methyl-6-nitropyridin-3-yl)oxy)pyridin-2-yl) carbamate

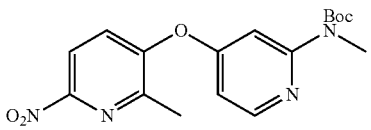 [SMILES: Cc1nc([N+](=O)[O-])ccc1Oc1ccnc(N(C)C(=O)OC(C)(C)C)c1]

3-((2-chloropyridin-4-yl)oxy)-2-methyl-6-nitropyridine (300 mg, 1.13 mmol), tert-butyl methylcarbamate (225 mg, 1.70 mmol), XPhos-Pd-G3 (30 mg), BINAP (60 mg), and cesium carbonate (740 mg, 2.26 mmol) were dissolved in 1,4-dioxane (10 mL). The reaction solution was stirred at 110° C. for 2 hrs under a nitrogen atmosphere. When LCMS showed that the reaction completed, the reaction solution was filtered through celite, and the filtrate was concentrated, the residue was separated by a rapid silica gel column (0~40% EA:PE) to obtain tert-butylmethyl(4-((2-methyl-6-nitropyridin-3-yl)oxy)pyridin-2-yl)carbamate (320 mg, yield 78%). MS m/z (ESI): 361 [M+H]$^+$.

Step 2: Preparation of tert-butyl (4-((6-amino-2-methylpyridin-3-yl)oxy)pyridin-2-yl) (methyl) carbamate

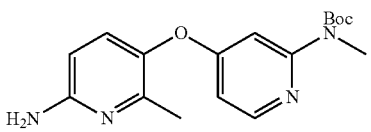

Tert-butyl methyl(4-((2-methyl-6-nitropyridin-3-yl)oxy)pyridin-2-yl)carbamate (320 mg, 0.89 mmol) and 10% palladium on carbon (50 mg) were dissolved in methanol (20 mL). The reaction mixture was stirred at room temperature for 1 hr under hydrogen atmosphere. When LCMS showed that the reaction completed, the reaction solution was filtered through celite, and the filtrate was concentrated, the residue was separated by a rapid silica gel column (0~40% EA:PE) to obtain tert-butyl (4-((6-amino-2-methylpyridin-3-yl)oxy)pyridin-2-yl)(methyl) carbamate (250 mg, 85%). MS m/z (ESI): 331 [M+H]$^+$.

Step 3: Preparation of tert-butyl (4-((6-(3,3-dimethyl-2-oxopyrrolidine4-carboxamido)-2-methylpyridin-3-yl)oxy)pyridin-2-yl)(methyl)carbamate

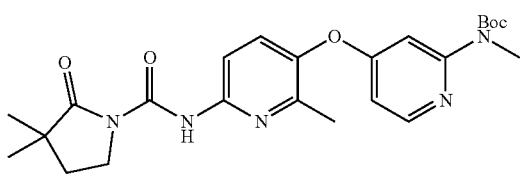

Triphosgene (133 mg, 0.45 mmol) was dissolved in dichloromethane (5 mL), and the solution of 3,3-dimethylpyrrolidin-2-one (103 mg, 0.9 mmol) and pyridine (0.3 mL) in dichloromethane (3 mL) was added under an ice bath. The reaction solution was stirred for 0.5 hr under an ice bath. The above solution was then added to the solution of tert-butyl (4-((6-amino-2-methylpyridin-3-yl)oxy)pyridin-2-yl)(methyl)carbamate (100 mg, 0.3 mmol) and pyridine (0.2 mL) in dichloromethane (5 mL) under an ice bath. The reaction solution was stirred at room temperature for 2 hrs, then poured into water (50 mL) and extracted with dichloromethane (40 mL*2). The organic phases were combined, dried over sodium sulfate, concentrated and separated by column chromatography (0~75% EA:PE) to obtain tert-butyl (4-((6-(3,3-dimethyl-2-oxopyrrolidine-1-carboxamido)-2-methylpyridin-3-yl)oxy)pyridin-2-yl) (methyl) carbamate (60 mg, yield 43%), MS m/z (ESI): 470 [M+H]$^+$.

Step 4: Preparation of 3,3-dimethyl-N-(6-methyl-5-((2-(methylamino)pyridin-4-yl)oxy) pyridin-2-yl)-2-oxopyrrolidine-1-carboxamide

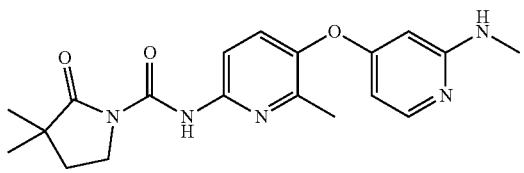

tert-butyl (4-((6-(3,3-dimethyl-2-oxopyrrolidine-1-carboxamido)-2-methylpyridin-3-yl)oxy) pyridin-2-yl) (methyl)carbamate (60 mg, 0.13 mmol) and trifluoroacetic acid (2 mL) were dissolved in dichloromethane (10 mL). The reaction solution was stirred at room temperature for 1 hr. When the LCMS showed that the starting materials disappeared, the resultant solution was concentrated and separated by a rapid reversed phase silica gel column (0~50% MeCN: H$_2$O) to obtain 3,3-dimethyl-N-(6-methyl-5-((2-(methylamino)pyridin-4-yl)oxy)pyridin-2-yl)-2-oxopyrrolidine-1-carboxamide (23.0 mg, yield 48%). MS m/z (ESI): 370 [M+H]$^+$.

$^1$H NMR (400 MHz, Chloroform-d) δ 11.03 (s, 1H), 7.94 (d, J=3.2 Hz, 1H), 7.93 (s, 1H), 7.35 (d, J=8.8 Hz, 1H), 6.12 (dd, J=5.9, 2.1 Hz, 1H), 5.75 (d, J=2.1 Hz, 1H), 4.71 (d, J=5.3 Hz, 1H), 3.86 (t, J=7.1 Hz, 2H), 2.84 (d, J=5.0 Hz, 3H), 2.33 (s, 3H), 1.94 (t, J=7.1 Hz, 2H), 1.27 (s, 6H).

BIOLOGICAL TEST EVALUATION

A CST-1R In Vitro Biochemical Kinase Study

In the present invention, the inhibitory activity of compounds against the CSF-1R activity was determined by using CSF-1R ADP-Glo assay. The compound-mediated inhibition effect was achieved by inhibiting the production of ADP from consumption of ATP, and the activities of compounds were evaluated by using the ADP-Glo kit (Promega, cat. No, V9101). The specific experimental process is as follows:

1. The kinase reaction performed in the present invention was carried out in a 384-well plate (Perkinelmer, cat. No. 6007290). 3.95 nM of CSF-1R, 500 μM of ATP, and 0.2 mg/mL of polypeptide (Poly (Glu4, Try1), Sigma, cat. No. P0275) were respectively weighed and added to each well;

2. following reagents were then added to each well to reach the final reaction system: 40 mM Tris, pH 7.5, 20 mM MgCl$_2$, 0.01% Triton X-100, 0.1 mg/mL BSA, 2.5 mM DTT, and 0.1% DMSO;

3. the reaction was conducted at 30° C. for 60 min;

4. then a equal volume of stop solution (ADP-Glo) was added to the kinase reaction system;

5. the mixed solution was incubated at 25° C. for 60 min, and the kinase reaction was then terminated;

6. a two-fold volume of detection reagent was then added to each well;

7. the mixed solution was incubated at 25° C. for 30 min;

8. the compound IC$_{50}$ value was measured by using a plate reader (Tecan, M1000) and a four-parameter curve was generated in Graphpad Prism. The enzymatic activities of compounds in the specific embodiments are shown in Table 1.

B. KIT/PDGFRA in vitro biochemical kinase study

1. Preparation of 1-fold kinase buffer and stop solution
   1.1. 1-fold kinase buffer: 50 mM HEPES, pH 7.5, 0.0015% Brij-35.
   1.2 stop solution: 100 mM HEPES, pH 7.5, 0.015% Brij-35, 0.2% Coating Reagent #3, 50 mM EDTA 2 Preparation of compound solution
   2.1 Dilution of compound solution
   1) The final concentration of the compound solution was 40 μM, and the concentration of the prepared stock solution was 50 times of the final concentration, i.e., 2 mM.
   2) 80 μL of 100% DMSO was added to the second well of a 96-well plate, and then 20 μL of 10 mM compound solution was added to obtain 2 mM compound solution. 60 μL of 100% DMSO was added to other wells. 20 μL solution was taken from the second well and added to the third well, which was diluted by 4 times. This serial 4-time dilution was conducted in sequence for the total of 10 concentration.

2.2 5-fold compound solution transferred to a reaction plate
1) 10 µL solution was taken from each well of the above 96-well plate and added to another 96-well plate, and 90 p1 of kinase buffer was added in each well of new plate.
2) 5 µL solution was taken from the above 96-well plate and added to a 384-well reaction plate.
2.3 Kinase reaction
1) KIT/PDGFRA kinase was added to the 1-fold kinase buffer solution to obtain a 2.5-fold kinase solution.
2) FAM-labeled polypeptide and ATP were added to the 1-fold kinase buffer solution to obtain a 2.5-fold substrate solution.
3) 10 µL of 2.5-fold kinase solution was added to the 384-well reaction plate, which already contained 5 µL of 5-fold compound in 10% DMSO. And the mixed solution was incubated at room temperature for 10 min.
4) 10 µL of 2.5-fold substrate solution was added to the 384-well reaction plate.
5) Kinase reaction and termination: the mixed solution is incubated at 28° C. for a certain period of time, and 25 µL, of stop solution was added to stop the reaction.
2.4 Data reading of Caliper EZ Reader II
2.5 Calculation of percent inhibition and $IC_{50}$
1) Percent conversion data were copied from the Caliper EZ Reader.
2) Percent conversion was converted into percent inhibition data, wherein, max referred to percent conversion of the DMSO control, and min referred to percent conversion of the negative control without kinase activity.

Percent inhibition=(max-conversion)/(max-min)×100

3) The $IC_{50}$ value was fit with XLFit excel add-in version 5.4.0,8: Fitting formula:

Y=Bottom+(Top-Bottom)/(1+($IC_{50}$/X)^HillSlope).

The enzymatic activities of compounds in the specific embodiments are shown in Table 1.
C. CSF-1R cell proliferation study
Functional effects of compounds on cell proliferation were evaluated by using Cell Titer Glo (CTG) study in the present invention. M-NFS-60 mouse myeloid leukemia lymphocytes (cat. No. CCB,1078) from National Institutes For Food and Drug Control were cultured in the incubator under conditions of RPMI 1640 (Gibco, cat. No. 11875-119), 10% fetal bovine serum (Gibco, 10099-141), human 10 ng/mL M-CSF macrophage colony-stimulating factor (R&D, cat. No. MVN0915101), 37° C., and 5% $CO_2$. Since ATP is an index for viable cell metabolism, CTG (Promega, #G7573) reagent is a homogeneous detection method for detecting the number of viable cells in the culture by quantifying ATP. Therefore, compound-mediated inhibition for cell proliferation/survival was evaluated by quantifying ATP content in cells, and the specific experimental process was as follows:
1. The cells was plated into a tissue-culture-medium-treated 96-well plate (Costar #3904) with 5,000 cells/well/ 80 µL fresh culture medium;
2. 24 hours later, 10 µL culture medium containing testing compound with 10-fold of final concentration was added to each well;
3. 10 µL of culture medium containing M-CSF with 10-fold of the final concentration was then added to each well;
4. dosage effect was evaluated by testing the 3-fold serial dilutions of the compound;
5. after the cells were incubated for 3 days at 37° C. and 5% $CO_2$, the inhibition on cell survival was quantified after 50 µL of CTG was added and the luminescence assay was performed;
6. the compound concentration leading to half maximal inhibitory ($IC_{50}$) and the compound concentration leading to absolute half maximal inhibitory (Absolute $IC_{50}$) was measured by a plate reader (M1000, Tecan) and a four-parameter curve fit in Graphpad Prism 7. The cell viabilities for compounds in the specific embodiments are shown in Table 1.
D. CSF-1R-related cell proliferation experiment
Functional effects of compounds on the proliferation of several cell lines were evaluated by Cell Titer Glo (CTG) studies in the present invention, and effects of the compounds on the proliferation of different cells were evaluated to determine the selectivity of the compounds. In the experiment, M-07e human cytomegalic leukemia cells (cat. No. CBP60791) from Nanjing Kebai Biotechnology Co., Ltd. were cultured in an incubator under conditions of RPMI1640 (Gibco, cat. No, 11875-119), 20% fetal bovine serum (Gibco, 10099-141), human 10 ng/mL GM-CSF granulocyte macrophage colony-stimulating factors (R&D, cat. No. 215-GM-010), 37° C., and 5% $CO_2$; and Kasumi-1 human acute myeloblastic leukemia cells (cat. No. CBP60524) were cultured in an incubator under conditions of RPMI1640 (Gibco, cat. No. 11875-119), 20% fetal bovine serum (Gihco, 10099-141), 37° C., and 5% $CO_2$; NCI-H1703 human non-small cell lung squamous carcinoma cells (cat. No. CBP60115) were cultured in an incubator under conditions of RPM11640 (Gibco, cat. No. 11875-119), 10% fetal bovine serum (Gibco, 10099-141), 37° C., and 5% $CO_2$; MV-4-11 human acute monocytic leukemia cells (cat. No. CBP60522) were cultured in an incubator under conditions of IMDM (Invitrogen, cat. No. 12440053), 20% fetal bovine serum (Gibco, 10099-141), 37° C. and 5% $CO_2$. Since ATP is an index for viable cell metabolism, CTG (Promega, #G7573) reagent is a homogeneous detection method for detecting the number of viable cells in the culture by quantifying ATP. Therefore, compound-mediated inhibition for cell proliferation/survival was evaluated by quantifying ATP content in cells, and the specific experimental process was as follows. The cell viabilities for compounds in the specific embodiments are shown in Table 1.
I) M-07e human cytomegalic leukemia cell:
1. The cells were plated into a tissue-culture-medium-treated 96-well plate (Costar #3904) with 3500 cells/well/80 µL fresh culture medium, and cultured for 24 hrs;
2. the next day, 10 µL of culture medium containing testing compound with 10-fold of final concentration was added to each well;
3. 10 µL, of culture medium containing SCF recombinant human stem cell factor (R&D, cat. No. 7466-SC-010) with 10-fold of the final concentration was then added to each well;
4. the dosage effect was evaluated by testing 4-fold serial dilutions of the compound, which started from 18 µM;
5. after the cells were incubated for 3 days at 37° C. and 5% $CO_2$, the inhibition on cell survival was quantified after 50 µL of CTG was added and the luminescence assay was performed;

6. the compound concentration leading to half maximal inhibitory (IC$_{50}$) and the compound concentration leading to absolute half maximal inhibitory (Absolute IC$_{50}$) were measured by a plate reader (M1000, Tecan) and a four-parameter curve fit in Graphpad Prism 7.

II) NCI-H1703 human non-small cell lung squamous carcinoma cell
1. The cells were inoculated into a tissue-culture-medium-treated 96-well plate (Costar #3904) with 5000 cells/well/90 μL fresh culture medium, and cultured for 24 hrs;
2, the next day, 10 μL of culture medium containing testing compound with 10-fold of final concentration was added to each well;
3. the dosage effect was evaluated by testing 3-fold serial dilutions of the compound, which started from 18 μM;
4. after the cells were incubated for 3 days at 37° C. and 5% CO$_2$, the inhibition on cell survival was quantified after 50 μL of CTG was added and the luminescence assay was performed;
5. the compound concentration leading to half maximal inhibitory (IC$_{50}$) and the compound concentration leading to absolute half maximal inhibitory (Absolute IC$_{50}$) were measured by a plate reader (M1000, Tecan) and a four-parameter curve fit in Graphpad Prism 7.

III) MV-4-11 human acute monocytic leukemia cell
1, The cells were plated into a tissue-culture-medium-treated 96-well plate (Costar #3904) with 5000 cells/well/90 μL fresh culture medium, and cultured for 24 hrs;
2. the next day, 10 μL of culture medium containing testing compound with 10-fold of final concentration was added to each well;
3. the dosage effect was evaluated by testing 3-fold serial dilutions of the compound, which started from 18 μM;
4. after the cells were incubated for 3 days at 37° C. and 5% CO$_2$, the inhibition on cell survival was quantified after 50 μL of CTG is added and the luminescence assay was performed;
5, the compound concentration leading to half maximal inhibitory (IC$_{50}$) and the compound concentration leading to absolute half maximal inhibitory (Absolute IC$_{50}$) are measured by a plate reader (M1000, Tecan) and a four-parameter curve fit in Graphpad Prism 7.

TABLE I

Detection results for enzymatic and cell activities

| | Enzymatic experiment | | | Cytological experiment | | | | |
| | | | | CS1-1R | | | | |
| Example No. | CSF-1R IC$_{50}$ (nM) | KIT IC$_{50}$ (nM) | PDGFRA IC$_{50}$ (nM) | CSF-1R IC$_{50}$ (nM) | Absolute IC$_{50}$ (nM) | KIT IC$_{50}$ (nM) | FLT3 IC$_{50}$ (nM) | PDGERA IC$_{50}$ (nM) |
|---|---|---|---|---|---|---|---|---|
| 1 | 19.48* | 76.98* | 1399.21* | 25.0* | 24.1* | 1060.9* | 5555.6* | 2865.9* |
| 2 | 14.44 | 59.81 | 435.47 | 26.3* | 23.1* | 158.1 | 6000.0 | 18000.0 |
| 3 | 228.80 | NT | NT | 666.7 | 687.0 | NT | NT | NT |
| 4 | 42.85 | NT | NT | 216.5 | 212.7 | NT | NT | NT |
| 5 | 54.74 | NT | NT | 454.4 | 333.5 | NT | NT | NT |
| 6 | 25.76* | 166.96* | 2453.60* | 42.9* | 36.6* | 1668.8* | 9000.0* | 6000.0* |
| 7 | 72.51 | NT | NT | 222.3 | 203.2 | NT | NT | NT |
| 8 | 57.95 | NT | NT | 148.2 | 110.2 | NT | NT | NT |
| 9 | 80.21 | NT | NT | 216.5 | 192.8 | NT | NT | NT |
| 10 | 56.29* | 475.96 | 13065.84 | 104.4* | 139.9* | 4898.8* | 18000.0 | 6000.0 |
| 11 | 21.39 | NT | NT | 43.5 | 35.5 | >1125.0 | >6000.0 | >2000.0 |
| 12 | 71.72 | NT | NT | 158.5 | 133.5 | NT | NT | NT |
| 13 | 99.70 | NT | NT | 263.2 | 245.2 | NT | NT | NT |
| 14 | 46.42 | NT | NT | 117.6 | 114.7 | NT | NT | NT |
| 15 | 20.69 | NT | NT | 64.4 | 38.7 | >1125.0 | >6000.0 | >6000.0 |
| 16 | 230.00 | NT | NT | NT | NT | NT | NT | NT |
| 17 | 101.00 | NT | NT | NT | NT | NT | NT | NT |
| 18 | NT | NT | NT | 125.0 | 113.7 | NT | NT | NT |
| 19 | 176.40 | NT | NT | 644.5 | 646.8 | NT | NT | NT |
| 20 | 273.20 | NT | NT | 391.9 | 298.4 | NT | NT | NT |
| 21 | 59.89 | NT | NT | 45.2* | 31.2* | 727.2 | >2000.0 | >6000.0 |
| 22 | 248.95* | NT | NT | 500.0 | 500.0 | NT | NT | NT |
| 23 | 83.02 | NT | NT | 620.3* | 383.9* | NT | NT | NT |
| 24 | 56.58 | NT | NT | 220.6 | 163.7 | NT | NT | NT |
| 25 | 1118.00 | NT | NT | 1923.0* | 1986.5* | NT | NT | NT |
| 26 | 75.23 | NT | NT | 161.0 | 156.6 | NT | NT | NT |
| 27 | 135.30 | NT | NT | 486.8 | 441.1 | NT | NT | NT |
| 28 | 24.21 | 8.48 | 107.26 | 35.7* | 31.9* | 940.4* | 10000.0* | 9528.5* |
| 29 | 52.18 | 92.51 | 931.12 | 76.3 | 75.1 | >2000.0 | >18000.0 | >6000.0 |
| 30 | 98.33 | NT | NT | 1376.7* | 1155.3* | NT | NT | NT |
| 31 | 8.45 | NT | NT | 19.2* | 19.4* | 190.1 | 2983.0 | 561.3 |
| 32 | 324.10 | NT | NT | 666.7 | 781.6 | NT | NT | NT |
| 33 | 19.85 | NT | NT | 41.9* | 40.3* | 534.7 | >6000.0 | >6000.0 |
| 34 | 51.70 | NT | NT | 21.3* | 21.5* | 666.7 | >2000.0 | 1327.0 |
| 35 | 25.72 | NT | NT | 23.3* | 21.2* | 261.7 | >6000.0 | >2000.0 |
| 36 | NT | NT | NT | 500.0 | 726.8 | NT | NT | NT |
| 37 | 207.30 | NT | NT | 141.0 | 140.2 | NT | NT | NT |
| 38 | 1472.00 | NT | NT | NT | NT | NT | NT | NT |
| 39 | 20.20 | NT | NT | 48.3 | 35.0 | NT | NT | NT |

TABLE I-continued

Detection results for enzymatic and cell activities

| | Enzymatic experiment | | | Cytological experiment | | | | |
| | | | | CS1-1R | | | | |
| Example No. | CSF-1R $IC_{50}$ (nM) | KIT $IC_{50}$ (nM) | PDGFRA $IC_{50}$ (nM) | CSF-1R $IC_{50}$ (nM) | Absolute $IC_{50}$ (nM) | KIT $IC_{50}$ (nM) | FLT3 $IC_{50}$ (nM) | PDGERA $IC_{50}$ (nM) |
|---|---|---|---|---|---|---|---|---|
| 40 | 7.54 | NT | NT | 31.4 | 27.6 | NT | NT | NT |
| 41 | 444.60 | NT | NT | >2000.0 | >2000.0 | >18000.0 | >18000.0 | >18000.0 |
| 42 | 2280.00 | NT | NT | >2000.0 | >2000.0 | NT | NT | NT |

Notes
1, "NT" is an abbreviation of "Not Tested", and means that an object has not been detected yet.
2, The data marked with "*" at its upper right corner is the average value of results from multiple tests for the compounds of the embodiments of the present invention.

It can be concluded from the enzymatic activity data of the compounds in the specific embodiments that the compounds of the present invention have strong inhibitory effects on the kinase activity. It can be concluded from the cell activity data of the compounds in the specific embodiments that the compounds of the present invention have strong inhibitory effects on the proliferation activity of M-NFS-60 mouse myeloid leukemia lymphocytes that depends on CSF-1R signaling for proliferation. In addition, given the above experimental results, the compounds of the present invention have strong selectivity for KIT, FLT3, and PDGFRA, and are expected to be developed as the new generation of CSF-1R inhibitors with high selectivity, so as to meet clinical use requirements.

All documents mentioned in the present invention are incorporated by reference, just as each document is cited separately as a reference. In addition, it should be understood that various modifications or changes may be made by those skilled in the art after reading the above teachings of the present invention, and these equivalent forms also fall within the scope defined by the claims appended hereto.

We claim:

1. A compound of formula (I), a stereoisomer or pharmaceutically acceptable salt thereof:

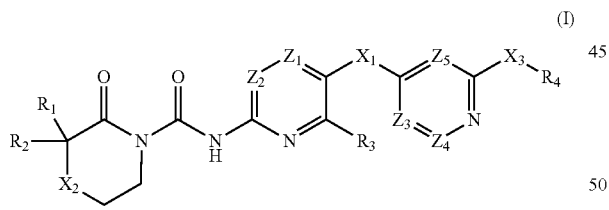

(I)

wherein, $X_1$, $X_2$ and $X_3$ are each independently bond, —O—, —S—, —($CR_5R_6$)m—, —N($R_7$)—, —N($R_8$)—C(O)— or —C(O)—N($R_8$)—;

$Z_1$, $Z_2$, $Z_3$, $Z_4$ and $Z_5$ are each independently C($R_9$) or N;

$R_1$ and $R_2$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=N$R_{10}$)$R_{11}$, —$C_{0-8}$—B(O$R_{12}$)$_2$, —$C_{0-8}$—P(O)($R_{13}$)$_2$, —$C_{0-8}$—S(O)$_r$$R_{11}$, —$C_{0-8}$—O—$R_{12}$, —$C_{0-8}$—C(O)O$R_{12}$, —$C_{0-8}$—C(O)$R_{13}$, —$C_{0-8}$—O—C(O)$R_{13}$, —$C_{0-8}$—N$R_{14}$$R_{15}$, —$C_{0-8}$—C(O)N$R_{14}$$R_{15}$ and —$C_{0-8}$—N($R_{14}$)—C(O)$R_{13}$, or, $R_1$ and $R_2$, together with the carbon atom directly attached thereto, form carbonyl, $C_{3-10}$ cycloalkyl or 3-10 membered heterocyclyl, wherein $R_1$ and $R_2$ are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{11}$, —$C_{0-8}$—O—$R_{12}$, —$C_{0-8}$—C(O)O$R_{12}$, —$C_{0-8}$—C(O)$R_{13}$, —$C_{0-8}$—O—C(O)$R_{13}$, —$C_{0-8}$—N$R_{14}$$R_{15}$, —$C_{0-8}$—C(O)N$R_{14}$$R_{15}$ and —$C_{0-8}$—N($R_{14}$)—C(O)$R_{13}$;

$R_3$ and $R_9$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=N$R_{10}$)$R_{11}$, —$C_{0-8}$—B(O$R_{12}$)$_2$, —$C_{0-8}$—P(O)($R_{13}$)$_2$, —$C_{0-8}$—S(O)$_r$$R_{11}$, —$C_{0-8}$—O—$R_{12}$, —$C_{0-8}$—C(O)O$R_{12}$, —$C_{0-8}$—C(O)$R_{13}$, —$C_{0-8}$—O—C(O)$R_{13}$, —$C_{0-8}$—N$R_{14}$$R_{15}$, —$C_{0-8}$—C(O)N$R_{14}$$R_{15}$ and —$C_{0-8}$—N($R_{14}$)—C(O)$R_{13}$, wherein $R_3$ and $R_9$ are optionally further substituted by one or more substituents selected from the group consisting of deuterium, halogen, cyan, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{11}$, —$C_{0-8}$—O—$R_{12}$, —$C_{0-8}$—C(O)O$R_{12}$, —$C_{0-8}$—C(O)$R_{13}$, —$C_{0-8}$—O—C(O)$R_{13}$, —$C_{0-8}$—N$R_{14}$$R_{15}$, —$C_{0-8}$—C(O)N$R_{14}$$R_{15}$ and —$C_{0-8}$—N($R_{14}$)—C(O)$R_{13}$;

$R_4$ is selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$$R_{11}$, —$C_{0-8}$—O—$R_{12}$, —$C_{0-8}$—C(O)O$R_{12}$, —$C_{0-8}$—C(O)$R_{13}$, —$C_{0-8}$—O—C(O)$R_{13}$, —$C_{0-8}$—N$R_{14}$$R_{15}$, —$C_{0-8}$—C(O)N$R_{14}$$R_{15}$ and —$C_{0-8}$—N($R_{14}$)—C(O)$R_{13}$, wherein $R_4$ is optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$$R_{11}$, —$C_{0-8}$—O—$R_{12}$, —$C_{0-8}$—C(O)O$R_{12}$, —$C_{0-8}$—C(O)$R_{13}$, —$C_{0-8}$—O—C(O)$R_{13}$, —$C_{0-8}$—N$R_{14}$$R_{15}$, —$C_{0-8}$—C(O)N$R_{14}$$R_{15}$ and —$C_{0-8}$—N($R_{14}$)—C(O)$R_{13}$;

wherein the above-mentioned substituents of $R_4$ are optionally more further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$, wherein, cycloalkyl, heterocyclyl, aryl, and heteroaryl are optionally more further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$;

$R_5$ and $R_6$ are each independently selected from the group consisting of hydrogen, deuterium, halogen, cyano, nitro, azido, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)(=NR$_{10}$)R$_{11}$, —$C_{0-8}$—B(OR$_{12}$)$_2$, —$C_{0-8}$—P(O)(R$_{13}$)$_2$, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$, or $R_5$ and $R_6$, together with the carbon atom directly attached thereto, form carbonyl, $C_{3-10}$ cycloalkyl or 3-10 membered heterocyclyl, wherein $R_5$ and $R_6$ are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$;

$R_7$ and $R_8$ are each independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$, wherein $R_7$ and $R_8$ are optionally further substituted by one or more substituents selected from the group consisting of deuterium, halogen, cyano, nitro, azido, $C_{1-8}$ alkyl, $C_{2-8}$ alkenyl, $C_{2-8}$ alkynyl, $C_{1-8}$ haloalkyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$;

each $R_{10}$ is independently selected from the group consisting of hydrogen, deuterium, $C_{1-8}$ alkyl, $C_{3-10}$ cycloalkylC$_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, —$C_{0-8}$—S(O)$_r$R$_{11}$, —$C_{0-8}$—O—R$_{12}$, —$C_{0-8}$—C(O)OR$_{12}$, —$C_{0-8}$—C(O)R$_{13}$, —$C_{0-8}$—O—C(O)R$_{13}$, —$C_{0-8}$—NR$_{14}$R$_{15}$, —$C_{0-8}$—C(O)NR$_{14}$R$_{15}$ and —$C_{0-8}$—N(R$_{14}$)—C(O)R$_{13}$;

each $R_{11}$ is independently selected from the group consisting of hydrogen, deuterium, hydroxy, $C_{1-8}$ alkyl, $C_{1-8}$ alkoxy, $C_{2-8}$ alkenyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$, wherein $R_{11}$ is optionally further substituted by one or more substituents selected from the group consisting of deuterium, halogen, hydroxy, carbonyl, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$;

each $R_{12}$ is independently selected from the group consisting of hydrogen, deuterium, $C_{1-8}$ alkyl, $C_{2-8}$ alkenyl, $C_{3-10}$ cycloalkyl, 3-10 membered heterocyclyl, $C_{5-10}$ aryl and 5-10 membered heteroaryl, wherein $R_{12}$ is optionally further substituted by one or more substituents selected from the group consisting of deuterium, halogen, hydroxy, carbonyl, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$;

each $R_{13}$ is independently selected from the group consisting of hydrogen, deuterium, hydroxy, $C_{1-8}$ alkyl, $C_{1-8}$ alkoxy, $C_{2-8}$ alkenyl, $C_{2-8}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$, wherein $R_{13}$ is optionally further substituted by one or more substituents selected from the group consisting of deuterium, halogen, hydroxy, cyano, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and —NR$_{14}$R$_{15}$;

each of $R_{14}$ and $R_{15}$ is independently selected from the group consisting of hydrogen, deuterium, hydroxy, $C_{1-8}$ alkyl, $C_{2-8}$ alkenyl, $C_{2-8}$ alkynyl, $C_{3-10}$ cycloalkyl, 3-10 membered heterocyclyl, $C_{5-10}$ aryl, 5-10 membered heteroaryl, sulfonyl, methanesulfonyl, isopropylsulfonyl, cyclopropylsulfonyl, p-toluenesulfonyl, amino, monoalkylamino, dialkylamino and $C_{1-8}$ alkanoyl, wherein $R_{14}$ and $R_{15}$ are optionally further substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

or $R_{14}$ and $R_{15}$, together with nitrogen atom directly attached thereto, form 5-10 membered heterocyclyl, which is optionally further substituted by one or more substituents selected from the group consisting of deuterium, halogen, hydroxy, $C_{1-8}$ alkyl, $C_{1-8}$ alkoxy, $C_{3-10}$ cycloalkyl, $C_{3-10}$ cycloalkyloxy, 3-10 membered heterocyclyl, 3-10 membered heterocyclyloxy; $C_{5-10}$ aryl, $C_{5-10}$ aryloxy, 5-10 membered heteroaryl, 5-10 membered heteroaryloxy, amino, monoalkylamino, dialkylamino and $C_{1-8}$ alkanoyl;

m is 0, 1, 2, 3, 4 or 5;

and r is 0, 1 or 2.

2. The compound of formula (I), the stereoisomer or pharmaceutically acceptable salt thereof according to claim 1, wherein $R_3$ is selected from the group consisting of hydrogen, deuterium, fluorine, chlorine, cyano, nitro, azido, $C_{1-4}$ alkyl, $C_{2-4}$ alkenyl; $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)(=$NR_{10}$)$R_{11}$, —$C_{0-4}$—B(O$R_{12}$)$_2$, —$C_{0-4}$—P(O)($R_{13}$)$_2$, —$C_{0-4}$—S(O)$_r$$R_{11}$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$, wherein $R_3$ is optionally further substituted by one or more substituents selected from the group consisting of deuterium, halogen, cyano, nitro, azido, $C_{1-4}$ alkyl; $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{11}$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$;

wherein, $R_{10}$, $R_{11}$, $R_{12}$, $R_{13}$, $R_{14}$, $R_{15}$, and r are defined as in claim 1.

3. The compound of formula (I), the stereoisomer or pharmaceutically acceptable salt thereof according to claim 2, wherein $R_3$ is selected from the group consisting of hydrogen, deuterium, fluorine, chlorine, cyano, nitro, azido, methyl, ethyl, isopropyl, allyl, ethynyl, cyclopropyl, cyclopropylmethyl, oxa-cyclobutyl, aza-cyclopentyl, aza-cyclohexyl, phenyl, diazole, triazole, methanesulfonyl, isopropylsulfonyl, aminosulfonyl, methoxy, ethoxy, isopropoxy, methoxyethyl, ethoxyethyl, hydroxymethyl, hydroxyethyl, cyanomethyl, trifluoromethyl, trideuteriomethyl, difluoromethyl, dideuteriomethyl, methoxycarbonyl, ethoxycarbonyl, acetyl, acetoxy, acetoxymethyl, amino, dimethylamino, aminomethyl, aminocarbonyl, dimethylaminocarbonyl and acetylamino.

4. The compound of formula (I), the stereoisomer or pharmaceutically acceptable salt thereof according to claim 1, wherein $R_1$ and $R_2$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, —$C_{0-4}$—S(O)(=$NR_{10}$)$R_{11}$, —$C_{0-4}$—B(O$R_{12}$)$_2$, —$C_{0-4}$—P(O)($R_{13}$)$_2$, —$C_{0-4}$—S(O)$_r$$R_{11}$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$, or, $R_1$ and $R_2$, together with the carbon atom directly attached thereto, form carbonyl, $C_{3-8}$ cycloalkyl or 3-8 membered heterocyclyl, wherein $R_1$ and $R_2$ are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$$R_{11}$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$;

wherein, $R_{10}$, $R_{11}$, $R_{12}$, $R_{13}$, $R_{14}$, $R_{15}$, and r are defined as in claim 1.

5. The compound of formula (I), the stereoisomer or pharmaceutically acceptable salt thereof according to claim 4, wherein $R_1$ and $R_2$ are each independently selected from the group consisting of hydrogen, deuterium, hydroxy, methyl, ethyl, propyl, isopropyl, allyl, ethynyl, cyclopropyl, cyclopropylmethyl, oxa-cyclobutyl, aza-cyclopentyl, aza-cyclohexyl, phenyl, diazole, triazole, methoxy, ethoxy, isopropoxy, phenylmethoxy, methoxyethyl, ethoxyethyl, hydroxymethyl, hydroxyethyl, cyanomethyl, trifluoromethyl, trideuteriomethyl, difluoromethyl, dideuteriomethyl, methoxycarbonyl, ethoxycarbonyl, acetyl, acetoxy, acetoxymethyl, amino, dimethylamino, aminomethyl, aminocarbonyl, dimethylaminocarbonyl and acetylamino, or, $R_1$ and $R_2$, together with the carbon atom directly attached thereto, form carbonyl, $C_{3-6}$ cycloalkyl or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, isopropyl, allyl, ethynyl, cyclopropyl, cyclopropylmethyl, oxa-cyclobutyl, aza-cyclopentyl, aza-cyclohexyl, phenyl, diazole, triazole, methoxy, ethoxy, isopropoxy, methoxyethyl, ethoxyethyl, hydroxymethyl, hydroxyethyl, cyanomethyl, trifluoromethyl, difluoromethyl, methoxycarbonyl, ethoxycarbonyl, acetyl, acetoxy, acetoxymethyl, amino, dimethylamino, aminomethyl, aminocarbonyl, dimethylaminocarbonyl and acetylamino.

6. The compound of formula (I), the stereoisomer or pharmaceutically acceptable salt thereof according to claim 4, wherein $R_1$ and $R_2$ are each independently selected from the group consisting of hydrogen, deuterium, hydroxy, methyl, ethyl, propyl, cyclopropyl, cyclopropylmethyl, methoxy, ethoxy, phenylmethoxy, methoxyethyl, hydroxymethyl, cyanomethyl, trifluoromethyl, trideuteriomethyl, difluoromethyl, dideuteriomethyl and aminomethyl, or, $R_1$ and $R_2$, together with the carbon atom directly attached thereto, form carbonyl, $C_{3-6}$ cycloalkyl or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, cyclopropyl, cyclopropylmethyl, methoxy, ethoxy, methoxyethyl, hydroxymethyl, cyanomethyl, trifluoromethyl, difluoromethyl and aminomethyl.

7. The compound of formula (I), the stereoisomer or pharmaceutically acceptable salt thereof according to claim 1, wherein the compound of formula (I) is a compound having formula (IIa):

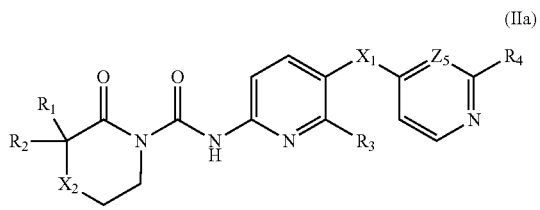

wherein, $X_1$ is —O— or —(C$R_5R_6$)—;

$X_2$ is bond, —O—, —(C$R_5R_6$)— or —N($R_7$)—;

$R_1$ and $R_2$ are each independently selected from the group consisting of hydrogen, deuterium, hydroxy, methyl, ethyl, propyl, cyclopropyl, cyclopropylmethyl, methoxy, ethoxy, phenylmethoxy, methoxyethyl, hydroxymethyl, cyanomethyl, trifluoromethyl, trideuteriomethyl, difluoromethyl, dideuteriomethyl and aminomethyl, or, $R_1$ and $R_2$, together with the carbon atom directly attached thereto, form carbonyl, $C_{3-6}$ cycloalkyl or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, cyclopropyl, cyclopropylmethyl, methoxy, ethoxy, methoxyethyl, hydroxymethyl, cyanomethyl, trifluoromethyl, difluoromethyl and aminomethyl;

$R_3$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_4$ is selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, $-C_{0-4}-S(O)_rR_{11}$, $-C_{0-4}-O-R_{12}$, $-C_{0-4}-C(O)OR_{12}$, $-C_{0-4}-C(O)R_{13}$, $-C_{0-4}-O-C(O)R_{13}$ and $-C_{0-4}-NR_{14}R_{15}$, wherein $R_4$ is optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, $-C_{0-4}-S(O)_rR_{11}$, $-C_{0-4}-O-R_{12}$, $-C_{0-4}-C(O)OR_{12}$, $-C_{0-4}-C(O)R_{13}$, $-C_{0-4}-O-C(O)R_{13}$, $-C_{0-4}-NR_{14}R_{15}$, $-C_{0-4}-C(O)NR_{14}R_{15}$ and $-C_{0-4}-N(R_{14})-C(O)R_{13}$, wherein the above-mentioned substituents of $R_4$ are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, $-C_{0-4}-S(O)_rR_{11}$, $-C_{0-4}-O-R_{12}$, $-C_{0-4}-C(O)OR_{12}$, $-C_{0-4}-C(O)R_{13}$, $-C_{0-4}-O-C(O)R_{13}$, $-C_{0-4}-NR_{14}R_{15}$, $-C_{0-4}-C(O)NR_{14}R_{15}$ and $-C_{0-4}-N(R_{14})-C(O)R_{13}$, wherein cycloalkyl, heterocyclyl, aryl, and heteroaryl are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, $-C_{0-4}-S(O)_rR_{11}$, $-C_{0-4}-O-R_{12}$, $-C_{0-4}-C(O)OR_{12}$, $-C_{0-4}-C(O)R_{13}$, $-C_{0-4}-O-C(O)R_{13}$, $-C_{0-4}-NR_{14}R_{15}$, $-C_{0-4}-C(O)NR_{14}R_{15}$ and $-C_{0-4}-N(R_{14})-C(O)R_{13}$;

$R_5$ and $R_6$ are each independently selected from the group consisting of hydrogen, deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, $-C_{0-4}-S(O)(=NR_{10})R_{11}$, $-C_{0-4}-B(OR_{12})_2$, $-C_{0-4}-P(O)(R_{13})_2$, $-C_{0-4}-S(O)_rR_{11}$, $-C_{0-4}-O-R_{12}$, $-C_{0-4}-C(O)OR_{12}$, $-C_{0-4}-C(O)R_{13}$, $-C_{0-4}-O-C(O)R_{13}$, $-C_{0-4}-NR_{14}R_{15}$, $-C_{0-4}-C(O)NR_{14}R_{15}$ and $-C_{0-4}-N(R_{14})-C(O)R_{13}$, or, $R_5$ and $R_6$, together with the carbon atom directly attached thereto, form carbonyl, $C_{3-8}$ cycloalkyl or 3-8 membered heterocyclyl, wherein $R_5$ and $R_6$ are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, haloalkyl, $C_{3-8}$ cycloalkyl, 3-8 membered heterocyclyl, $C_{5-8}$ aryl, 5-8 membered heteroaryl, $-C_{0-4}-S(O)_rR_{11}$, $-C_{0-4}-O-R_{12}$, $-C_{0-4}-C(O)OR_{12}$, $-C_{0-4}-C(O)R_{13}$, $-C_{0-4}-O-C(O)R_{13}$, $-C_{0-4}-NR_{14}R_{15}$, $-C_{0-4}-C(O)NR_{14}R_{15}$ and $-C_{0-4}-N(R_{14})-C(O)R_{13}$;

$R_7$ is selected from the group consisting of hydrogen, deuterium, $C_{1-4}$ alkyl, $C_{3-8}$ cycloalkyl, 3-8 membered heterocyclyl, $C_{5-8}$ aryl, and 5-8 membered heteroaryl, wherein $R_7$ is optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, $-C_{0-4}-S(O)_rR_{11}$, $-C_{0-4}-O-R_{12}$, $-C_{0-4}-C(O)OR_{12}$, $-C_{0-4}-C(O)R_{13}$, $-C_{0-4}-O-C(O)R_{13}$, $-C_{0-4}-NR_{14}R_{15}$, $-C_{0-4}-C(O)NR_{14}R_{15}$ and $-C_{0-4}-N(R_{14})-C(O)R_{13}$;

wherein, $Z_5$, $R_{10}$, $R_{11}$, $R_{12}$, $R_{13}$, $R_{14}$, $R_{15}$, and r are defined as in claim 1.

8. The compound of formula (I), the stereoisomer or pharmaceutically acceptable salt thereof according to claim 7, wherein $X_1$ is $-O-$ or $-(CR_5R_6)-$; $X_2$ is bond, $-O-$, $-CH_2-$ or $-N(R_7)-$;

$R_1$ and $R_2$ are each independently selected from the group consisting of hydrogen, deuterium, hydroxy, methyl, ethyl, propyl, cyclopropyl, cyclopropylmethyl, methoxy, ethoxy, phenylmethoxy, methoxyethyl, hydroxymethyl, cyanomethyl, trifluoromethyl, trideuteriomethyl, difluoromethyl, dideuteriomethyl and aminomethyl, or, $R_1$ and $R_2$, together with the carbon atom directly attached thereto, form carbonyl, $C_{3-6}$ cycloalkyl or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, cyclopropyl, cyclopropylmethyl, methoxy, ethoxy, methoxyethyl, hydroxymethyl, cyanomethyl, trifluoromethyl, difluoromethyl and aminomethyl;

$R_3$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_4$ is selected from $C_{5-8}$ aryl, 5-8 membered heteroaryl or $-NR_{14}R_{15}$, wherein $R_4$ is optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, $-C_{0-4}-S(O)_rR_{11}$, $-C_{0-4}-O-R_{12}$, $-C_{0-4}-C(O)OR_{12}$, $-C_{0-4}-C_{0-4}-O-(O)R_{13}$, $-C_{0-4}-NR_{14}R_{15}$, $-C_{0-4}-C(O)NR_{14}R_{15}$ and $-C_{0-4}-N(R_{14})-C(O)R_{13}$, wherein the above-mentioned substituents of $R_4$ are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, $-_{0-4}-S(O)_rR_{11}$, $-C_{0-4}-O-R_{12}$, $-C_{0-4}-C(O)OR_{12}$, $-C_{0-4}-C(O)R_{13}$, $-C_{0-4}-O-C(O)R_{13}$, $-C_{0-4}-NR_{14}R_{15}$, $-C_{0-4}-C(O)NR_{14}R_{15}$ and $-C_{0-4}-N(R_{14})-C(O)R_{13}$, wherein, the cycloalkyl, heterocyclyl, aryl, and heteroaryl are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$;

$R_5$ and $R_6$ are each independently selected from the group consisting of hydrogen, deuterium, fluorine, chlorine, methyl, trifluoromethyl, trideuteriomethyl, ethyl, isopropyl, cyclopropyl, cyclopropylmethyl, methoxy and methoxyethyl, or, $R_5$ and $R_6$, together with the carbon atom directly attached thereto, form carbonyl, cyclopropyl, cyclobutyl or oxa-cyclobutyl;

$R_7$ is selected from the group consisting of hydrogen, deuterium, methyl, ethyl, cyclopropyl, cyclopropylmethyl, trifluoromethyl and trideuteriomethyl;

$R_9$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

wherein, $R_{11}$, $R_{12}$, $R_{13}$, $R_{14}$, $R_{15}$, and r are defined as in claim 7.

9. The compound of formula (I), the stereoisomer or pharmaceutically acceptable salt thereof according to claim 8, wherein $X_1$ is —O— or —CH$_2$—; $X_2$—; $X_2$ is bond, —O— or —CH$_2$—;

$R_1$ and $R_2$ are each independently selected from the group consisting of hydrogen, deuterium, hydroxy, methyl, ethyl, propyl, cyclopropyl, cyclopropylmethyl, methoxy, ethoxy, phenylmethoxy, methoxyethyl, hydroxymethyl, cyanomethyl, trifluoromethyl, trideuteriomethyl, difluoromethyl, dideuteriomethyl and aminomethyl, or, $R_1$ and $R_2$, together with the carbon atom directly attached thereto, form $C_{3-6}$ cycloalkyl;

$R_3$ is selected from the group consisting of hydrogen, deuterium, methyl, ethyl, cyclopropyl, cyclopropylmethyl, trifluoromethyl, trideuteriomethyl, difluoromethyl and dideuteriomethyl;

$R_9$ is selected from the group consisting of hydrogen, deuterium, fluorine, chlorine, cyano, cyclopropyl and cyclopropylmethyl.

10. The compound of formula (I), the stereoisomer or pharmaceutically acceptable salt thereof according to claim 8, wherein $R_4$ is selected from $C_{5-8}$ aryl, 5-8 membered heteroaryl or —NR$_{14}$R$_{15}$, wherein said $C_{5-8}$ aryl and 5-8 membered heteroaryl are selected from the following structures:

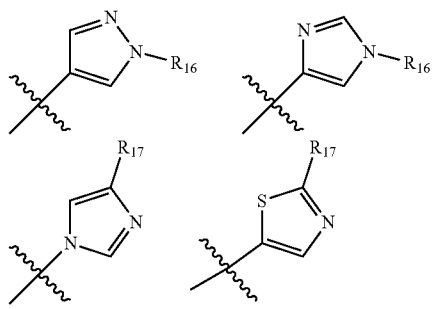

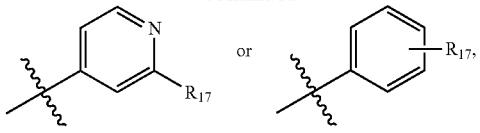

wherein, each $R_{16}$ is independently selected from the group consisting of hydrogen, deuterium, $C_{1-4}$ alkyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—C(O)OR$_{12}$ and —$C_{0-4}$—C(O)R$_{13}$, wherein $R_{16}$ is optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$, wherein the cycloalkyl, heterocyclyl, aryl, and heteroaryl are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$;

each $R_{17}$ is independently selected from the group consisting of hydrogen, deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$, wherein $R_{17}$ is optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$, wherein the cycloalkyl, heterocyclyl, aryl, and heteroaryl are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$;

wherein, $R_{11}$, $R_{12}$, $R_{13}$, $R_{14}$, $R_{15}$, and r are defined as in claim 8.

11. The compound of formula (I), the stereoisomer or pharmaceutically acceptable salt thereof according to claim 10, wherein each $R_{16}$ is independently selected from the group consisting of hydrogen, deuterium, $C_{1-4}$ alkyl, $C_{3-6}$ cycloalkyl, 3-6 membered heterocyclyl, phenyl and 5-6 membered heteroaryl, wherein $R_{16}$ is optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r$R$_{11}$, —$C_{0-4}$—O—R$_{12}$, —$C_{0-4}$—C(O)OR$_{12}$, —$C_{0-4}$—C(O)R$_{13}$, —$C_{0-4}$—O—C(O)R$_{13}$, —$C_{0-4}$—NR$_{14}$R$_{15}$, —$C_{0-4}$—C(O)NR$_{14}$R$_{15}$ and —$C_{0-4}$—N(R$_{14}$)—C(O)R$_{13}$;

each $R_{17}$ is independently selected from the group consisting of hydrogen, deuterium, fluorine, chlorine, cyano, nitro, azido, methyl, ethyl, isopropyl, allyl, ethynyl, cyclopropyl, cyclopropylmethyl, oxa-cyclobutyl, aza-cyclopentyl, aza-cyclohexyl, phenyl, diazole, triazole, methanesulfonyl, isopropylsulfonyl, aminosulfonyl, methoxy, ethoxy, isopropoxy, methoxyethyl, ethoxyethyl, hydroxymethyl, hydroxyethyl, cyanomethyl, trifluoromethyl, trideuteriomethyl, difluoromethyl, dideuteriomethyl, methoxycarbonyl, ethoxycarbonyl, acetyl, acetoxy, acetoxymethyl, amino, dimethylamino, aminomethyl, aminocarbonyl, dimethylaminocarbonyl and acetylamino;

wherein, $R_{11}$, $R_{12}$, $R_{13}$, $R_{14}$, $R_{15}$, and r are defined as in claim 10.

12. The compound of formula (I), the stereoisomer or pharmaceutically acceptable salt thereof according to claim 1, wherein the compound is selected from the following compounds:

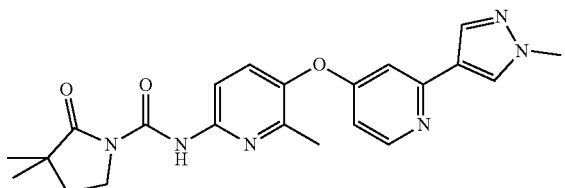

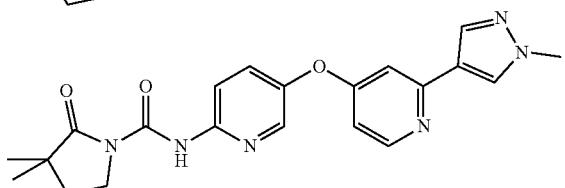

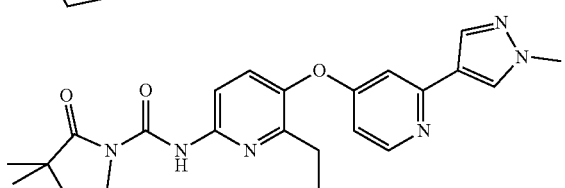

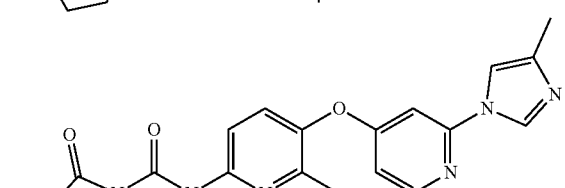

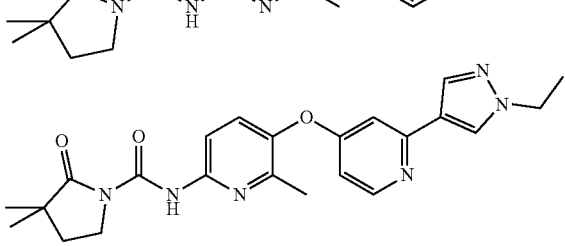

-continued

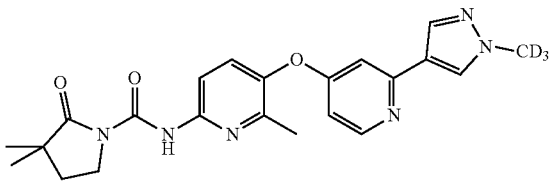

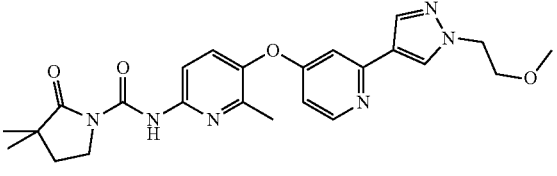

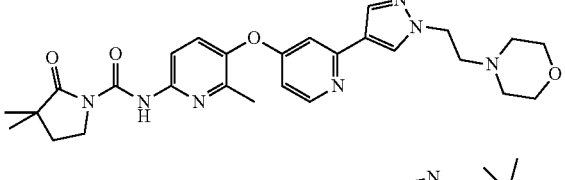

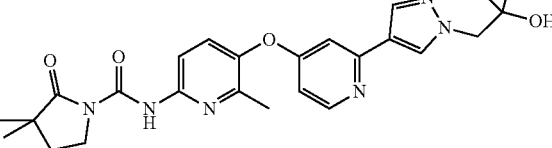

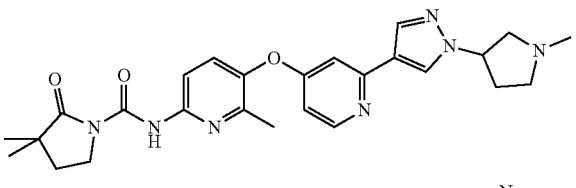

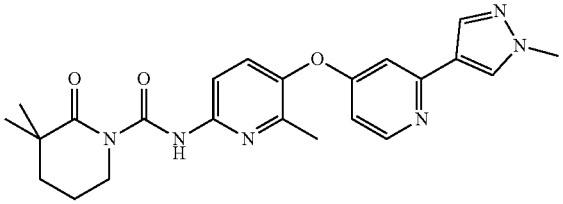

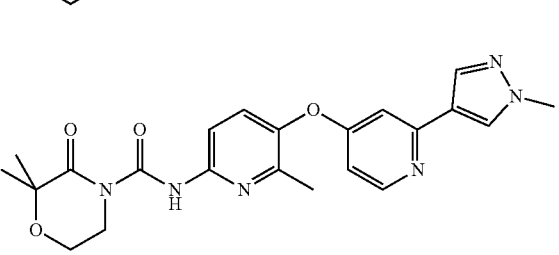

-continued
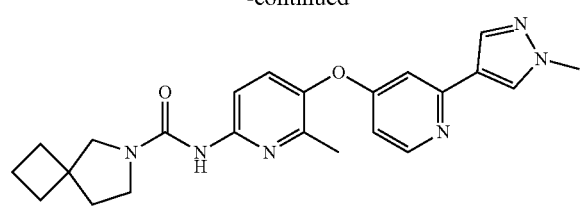
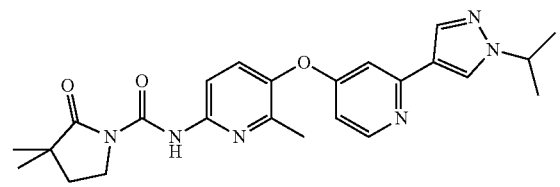
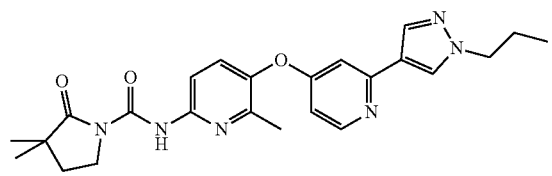
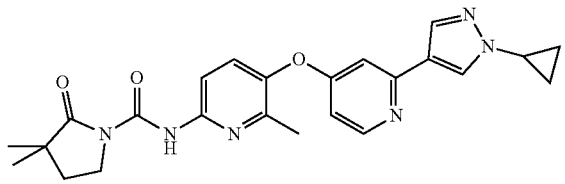
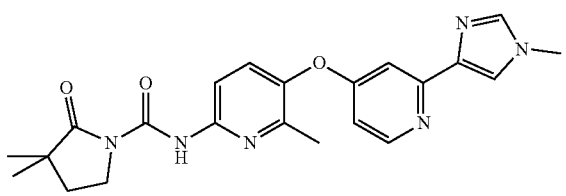
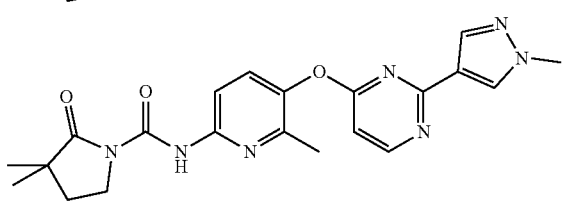
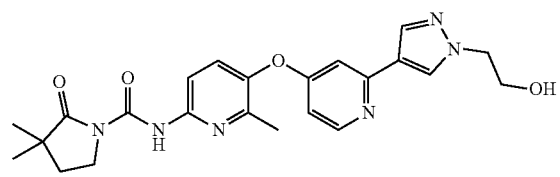
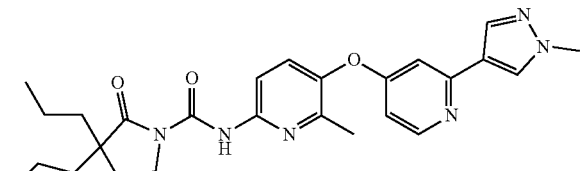
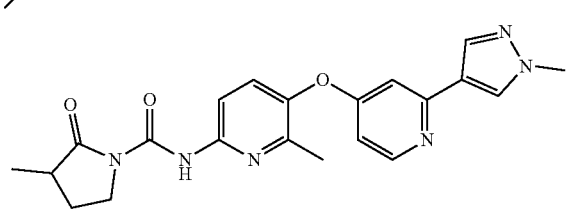
-continued
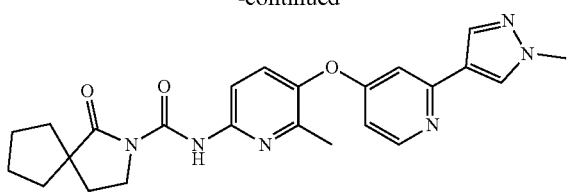
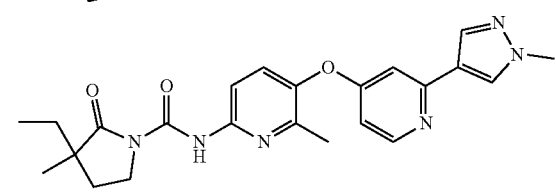
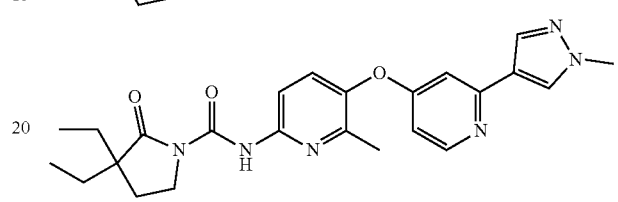
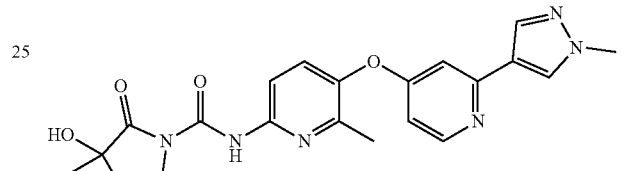
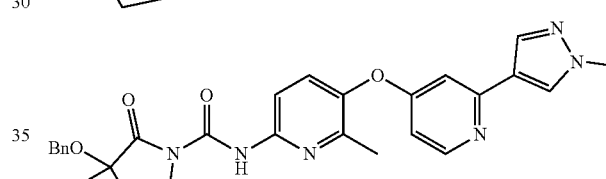
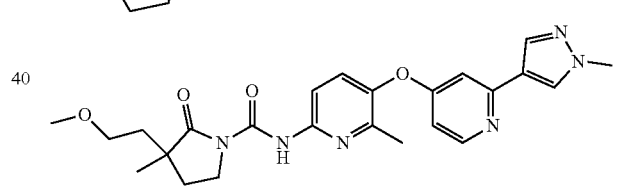
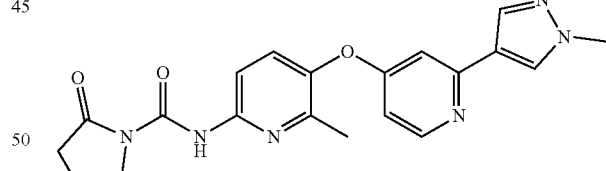
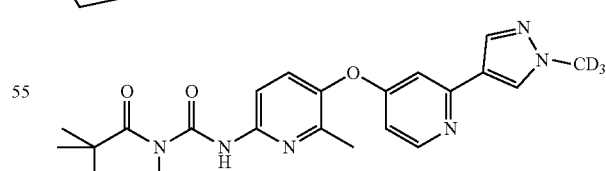
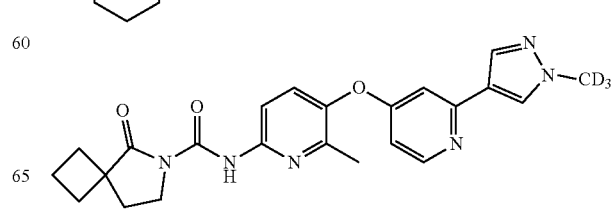

-continued

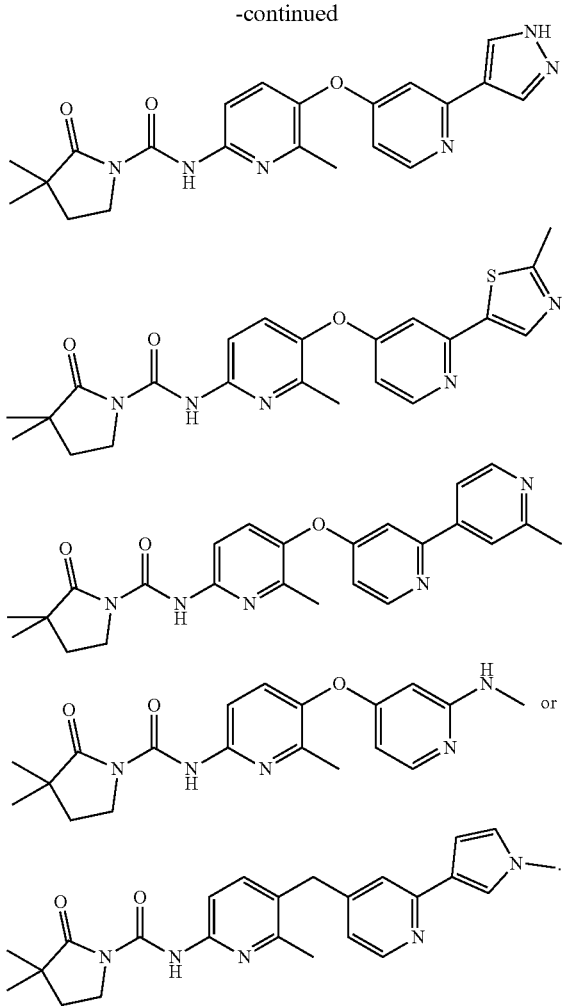

13. The compound of formula (I), the stereoisomer or pharmaceutically acceptable salt thereof according to claim 1, wherein the compound of formula (I) is a compound having formula (IIb):

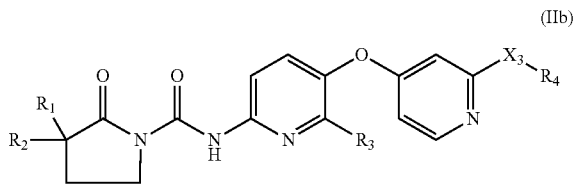

(IIb)

wherein,
$X_3$ is —C(O)—N($R_8$)— or —N($R_8$)—C(O)—;
$R_1$ and $R_2$ are each independently selected from the group consisting of hydrogen, deuterium, hydroxy, methyl, ethyl, propyl, cyclopropyl, cyclopropylmethyl, methoxy, ethoxy, methoxyethyl, hydroxymethyl, cyanomethyl, trifluoromethyl, trideuteriomethyl, difluoromethyl, dideuteriomethyl and aminomethyl,
or, $R_1$ and $R_2$, together with the carbon atom directly attached thereto, form carbonyl, $C_{3-6}$ cycloalkyl or 3-6 membered heterocyclyl, wherein the heteroatom is oxygen or nitrogen, and the cycloalkyl and heterocyclyl are optionally further substituted by one or more substituents selected from the group consisting of deuterium, hydroxy, methyl, ethyl, propyl, cyclopropyl, cyclopropylmethyl, methoxy, ethoxy, methoxyethyl, hydroxymethyl, cyanomethyl, trifluoromethyl, difluoromethyl and aminomethyl;

$R_3$ is selected from the group consisting of hydrogen, deuterium, fluorine, chlorine, cyano, methyl, ethyl, cyclopropyl, cyclopropylmethyl, methoxy, ethoxy, trifluoromethyl, trideuteriomethyl, difluoromethyl, dideuteriomethyl, amino and dimethylamino;

$R_4$ is selected from the group consisting of hydrogen, deuterium, $C_{1-4}$ alkyl, $C_{3-8}$ cycloalkyl, 3-8 membered heterocyclyl, $C_{5-8}$ aryl, 5-8 membered heteroaryl, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$ and —$C_{0-4}$—N$R_{14}R_{15}$, wherein $R_4$ is optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{3-8}$ cycloalkyl, 3-8 membered heterocyclyl, $C_{5-8}$ aryl, 5-8 membered heteroaryl, —$C_{0-4}$—S(O)$_r R_{11}$, —$C_{0-4}$—O—$R_{12}$, —$C_{0-4}$—C(O)O$R_{12}$, —$C_{0-4}$—C(O)$R_{13}$, —$C_{0-4}$—O—C(O)$R_{13}$, —$C_{0-4}$—N$R_{14}R_{15}$, —$C_{0-4}$—C(O)N$R_{14}R_{15}$ and —$C_{0-4}$—N($R_{14}$)—C(O)$R_{13}$;

$R_8$ is selected from the group consisting of hydrogen, deuterium, methyl, trifluoromethyl, trideuteriomethyl, cyclopropyl and cyclopropylmethyl;

wherein, $R_{11}$, $R_{12}$, $R_{13}$, $R_{14}$, $R_{15}$, and r are defined as in claim 1.

14. The compound of formula (I), the stereoisomer or pharmaceutically acceptable salt thereof according to claim 13, wherein, $R_1$ and $R_2$ are each independently selected from the group consisting of hydrogen, deuterium, hydroxy, methyl, ethyl, propyl, cyclopropyl, cyclopropylmethyl, hydroxymethyl, cyanomethyl, trifluoromethyl, trideuteriomethyl, difluoromethyl and dideuteriomethyl;

$R_3$ is selected from the group consisting of hydrogen, deuterium, methyl, ethyl, cyclopropyl, cyclopropylmethyl, trifluoromethyl, trideuteriomethyl, difluoromethyl and dideuteriomethyl;

$R_4$ is selected from $C_{1-4}$ alkyl, $C_{3-8}$ cycloalkyl or 3-8 membered heterocyclyl, wherein $R_4$ is optionally further substituted by one or more substituents selected from the group consisting of deuterium, $C_{1-4}$ alkyl, $C_{1-4}$ haloalkyl, $C_{3-8}$ cycloalkyl, 3-8 membered heterocyclyl, $C_{5-8}$ aryl and 5-8 membered heteroaryl;

$R_8$ is selected from the group consisting of hydrogen, deuterium, methyl, cyclopropyl and cyclopropylmethyl.

15. The compound of the formula (I), the stereoisomer or pharmaceutically acceptable salt thereof according to claim 13, wherein the compound is selected from the following compounds:

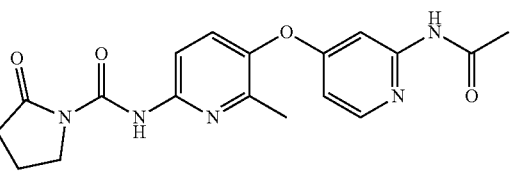

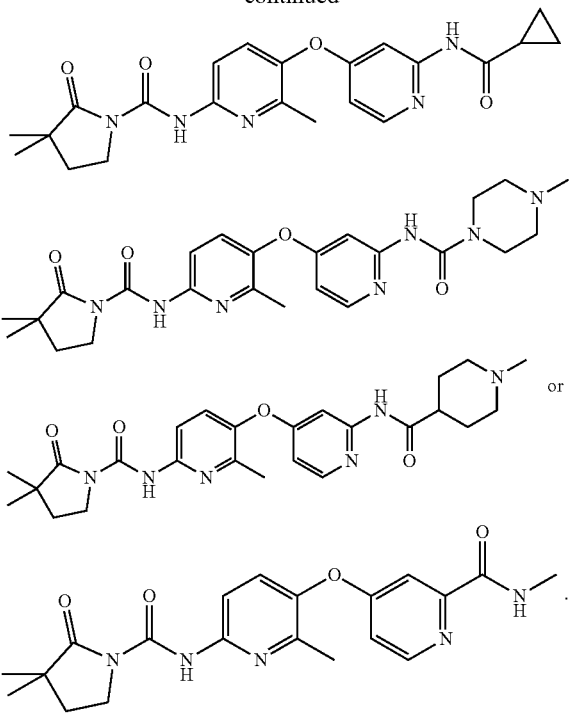

16. A process for preparing the compound of formula (I), the stereoisomer or pharmaceutically acceptable salt thereof according to claim 1, comprising the following steps: synthesizing the compound of formula (I) through a condensation reaction of the compound of formula (Ia) or an acidic salt thereof and the compound of formula (Ib), wherein the reaction is as follows:

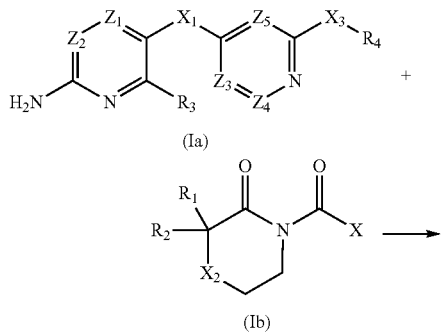

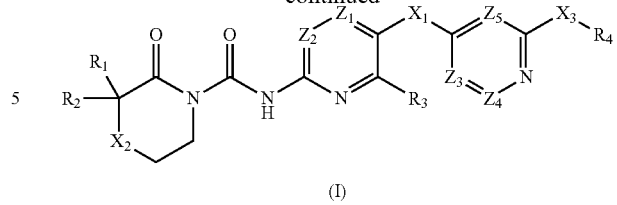

(I)

wherein, X is hydroxy, chlorine or bromine;
$X_1$, $X_2$, $X_3$, $Z_1$, $Z_2$, $Z_3$, $Z_5$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, m, and r are defined as in claim 1.

17. A pharmaceutical composition, comprising the compound of formula (I), the stereoisomer or pharmaceutically acceptable salt thereof of claim 1, and a pharmaceutically acceptable carrier.

18. A method for treating cancer, tumor, autoimmune disease, metabolic disease or metastatic disease, wherein the method comprises administering the pharmaceutical composition of claim 17 to a patient.

19. A method for treating ovarian cancer, pancreatic cancer, prostate cancer, lung cancer, breast cancer, renal carcinoma, liver cancer, cervical cancer, osseous metastasis cancer, papillary thyroid cancer, non-small cell lung cancer, colon cancer, gastrointestinal stromal tumor, solid tumor, melanoma, mesothelioma, glioblastoma, osteosarcoma, multiple myeloma, hyperproliferative disease, metabolic disease, neurodegenerative disease, primary tumor site metastasis, myeloproliferative disease, leukemia, rheumatic arthritis, rheumatoid arthritis, osteoarthritis, multiple sclerosis, autoimmune nephritis, lupus, Crohn's disease, asthma, chronic obstructive pulmonary disease, osteoporosis, hypereosinophilic syndrome, mastocytosis or mast cell leukemia, the method comprising administering the pharmaceutical composition of claim 17 to a patient.

20. The compound of formula (I), the stereoisomer or pharmaceutically acceptable salt thereof according to claim 2, wherein $R_3$ is selected from the group consisting of hydrogen, deuterium, fluorine, chlorine, cyano, methyl, ethyl, isopropyl, cyclopropyl, cyclopropylmethyl, oxa-cyclobutyl, methoxy, ethoxy, isopropoxy, methoxyethyl, ethoxyethyl, hydroxymethyl, hydroxyethyl, cyanomethyl, trifluoromethyl, trideuteromethyl, difluoromethyl, dideuteromethyl, amino and dimethylamino.

21. The compound of formula (I), the stereoisomer or pharmaceutically acceptable salt thereof according to claim 2, wherein $R_3$ is selected from the group consisting of hydrogen, deuterium, fluorine, chlorine, cyano, methyl, ethyl, cyclopropyl, cyclopropylmethyl, methoxy, ethoxy, trifluoromethyl, trideuteromethyl, difluoromethyl, dideuteromethyl, amino and dimethylamino.

\* \* \* \* \*